(12) United States Patent
Giedwoyn et al.

(10) Patent No.: US 11,918,854 B2
(45) Date of Patent: Mar. 5, 2024

(54) SYSTEM AND METHOD FOR ANALYZING ATHLETIC ACTIVITY

(71) Applicant: NIKE, Inc., Beaverton, OR (US)

(72) Inventors: Anna Antonia Giedwoyn, Portland, OR (US); Lee Peyton, Tigard, OR (US); Christopher L. Andon, Portland, OR (US)

(73) Assignee: NIKE, Inc., Beaverton, OR (US)

( * ) Notice: Subject to any disclaimer, the term of this patent is extended or adjusted under 35 U.S.C. 154(b) by 482 days.

(21) Appl. No.: 17/142,784

(22) Filed: Jan. 6, 2021

(65) Prior Publication Data
US 2021/0197021 A1    Jul. 1, 2021

Related U.S. Application Data

(63) Continuation of application No. 14/717,627, filed on May 20, 2015, now Pat. No. 10,926,133, which is a
(Continued)

(51) Int. Cl.
*A43B 3/00*      (2022.01)
*A43B 3/34*      (2022.01)
(Continued)

(52) U.S. Cl.
CPC ............ *A63B 24/0021* (2013.01); *A43B 3/34* (2022.01); *A63B 24/0062* (2013.01);
(Continued)

(58) Field of Classification Search
CPC ............ A63B 24/0021; A63B 24/0062; A63B 2024/0065; G16H 20/30; G16H 40/67; A43B 3/34
See application file for complete search history.

(56) References Cited

U.S. PATENT DOCUMENTS 3,094,606 A    6/1963    Ferris
3,270,564 A    9/1966    Evans
(Continued)

FOREIGN PATENT DOCUMENTS

CA    2668946 A1    5/2008
CN    2057062 U     5/1990
(Continued)

OTHER PUBLICATIONS

Suzanna Logan, Ian Hunter, J. Ty Hopkins, J. T., J. Brent Feland and Allen C. Parcell, "Ground reaction force differences between runnmg shoes, racing flats, and distance spikes in runners" 2010, Journal of Sports Science and Medicine, vol. 9, 147-153. (Year: 2010).*
(Continued)

*Primary Examiner* — John E Breene
*Assistant Examiner* — Christine Y Liao
(74) *Attorney, Agent, or Firm* — Banner & Witcoff, Ltd.

(57) ABSTRACT

A system for transitioning from a first footwear type to a second footwear type is usable with an article of footwear including a sensor system with a plurality of force sensors engaged with an article of footwear and configured to sense force exerted by a foot of a user and an electronic module configured to collect data based on force input from the sensors and to wirelessly transmit data generated by the sensor system. An electronic device includes a processor that receives the data from the electronic module, compares the data to a footstrike template corresponding to a desired footstrike pattern of a footwear transitional program, determines whether a deviation from the footstrike template exists, and generates an indication to the user when the deviation from the desired footstrike pattern is determined to exist. The desired footstrike pattern corresponds to a preferred footstrike of the second type of footwear.

20 Claims, 26 Drawing Sheets

Related U.S. Application Data continuation-in-part of application No. 13/757,417, filed on Feb. 1, 2013, now Pat. No. 11,006,690.

(51) Int. Cl.
*A63B 24/00* (2006.01)
*G16H 20/30* (2018.01)
*G16H 40/67* (2018.01)

(52) U.S. Cl.
CPC ............ *G16H 20/30* (2018.01); *G16H 40/67* (2018.01); *A63B 2024/0065* (2013.01)

(56) References Cited

U.S. PATENT DOCUMENTS

| | | | |
|---|---|---|---|
| 4,372,558 A | 2/1983 | Shimamoto et al. | |
| 4,373,651 A | 2/1983 | Fanslow | |
| 4,518,267 A | 5/1985 | Hepp | |
| 4,578,769 A | 3/1986 | Frederick | |
| 4,578,969 A | 4/1986 | Larson | |
| 4,647,918 A | 3/1987 | Goforth | |
| 4,703,445 A | 10/1987 | Dassler | |
| 4,745,930 A | 5/1988 | Confer | |
| 4,771,555 A | 9/1988 | Ohashi | |
| 4,814,661 A | 3/1989 | Ratzlaff et al. | |
| 4,862,743 A | 9/1989 | Seitz | |
| 4,866,412 A | 9/1989 | Rzepczynski | |
| 4,991,317 A | 2/1991 | Lakic | |
| 5,010,774 A | 4/1991 | Kikuo et al. | |
| 5,033,291 A | 7/1991 | Podoloff et al. | |
| 5,047,952 A | 9/1991 | Kramer et al. | |
| 5,050,962 A | 9/1991 | Monnier et al. | |
| 5,150,536 A | 9/1992 | Strong | |
| 5,154,960 A | 10/1992 | Mucci et al. | |
| 5,249,967 A | 10/1993 | O'Leary et al. | |
| 5,253,656 A | 10/1993 | Rincoe et al. | |
| 5,303,131 A | 4/1994 | Wu | |
| 5,323,650 A | 6/1994 | Fullen et al. | |
| 5,357,696 A | 10/1994 | Gray et al. | |
| 5,373,651 A | 12/1994 | Wood | |
| 5,374,821 A | 12/1994 | Muhs et al. | |
| 5,393,651 A | 2/1995 | Hoshi | |
| 5,408,873 A | 4/1995 | Schmidt et al. | |
| 5,419,562 A | 5/1995 | Cromarty | |
| 5,422,521 A | 6/1995 | Neer et al. | |
| 5,444,462 A | 8/1995 | Wambach | |
| 5,471,405 A | 11/1995 | Marsh | |
| 5,500,635 A | 3/1996 | Mott | |
| 5,588,227 A | 12/1996 | Goldston et al. | |
| 5,636,146 A | 6/1997 | Flentov et al. | |
| 5,636,378 A | 6/1997 | Griffith | |
| 5,638,300 A | 6/1997 | Johnson | |
| 5,644,858 A | 7/1997 | Bemis | |
| 5,655,316 A | 8/1997 | Huang | |
| 5,678,448 A | 10/1997 | Fullen et al. | |
| 5,697,791 A | 12/1997 | Nashner et al. | |
| 5,702,323 A | 12/1997 | Poulton | |
| 5,714,706 A | 2/1998 | Nakada et al. | |
| 5,720,200 A | 2/1998 | Anderson et al. | |
| 5,724,265 A | 3/1998 | Hutchings | |
| 5,764,786 A | 6/1998 | Kuwashima et al. | |
| 5,785,666 A | 7/1998 | Costello et al. | |
| 5,812,142 A | 9/1998 | Small et al. | |
| 5,813,142 A | 9/1998 | Demon | |
| 5,813,406 A | 9/1998 | Kramer et al. | |
| 5,815,954 A | 10/1998 | Huang | |
| 5,844,861 A | 12/1998 | Maurer | |
| 5,855,080 A | 1/1999 | Van Staden | |
| 5,889,464 A | 3/1999 | Huang | |
| 5,903,454 A | 5/1999 | Hoffberg et al. | |
| 5,907,819 A | 5/1999 | Johnson | |
| 5,913,727 A | 6/1999 | Ahdoot | |
| 5,929,332 A | 7/1999 | Brown | |
| 5,957,642 A | 9/1999 | Pratt | |
| 5,960,380 A | 9/1999 | Flentov et al. | |
| 5,963,891 A | 10/1999 | Walker et al. | |
| 5,983,433 A | 11/1999 | Chapman | |
| 6,017,128 A | 1/2000 | Goldston et al. | |
| 6,018,705 A | 1/2000 | Gaudet et al. | |
| 6,050,962 A | 4/2000 | Kramer et al. | |
| 6,066,075 A | 5/2000 | Poulton | |
| 6,081,750 A | 6/2000 | Hoffberg et al. | |
| 6,122,340 A | 9/2000 | Darley et al. | |
| 6,122,846 A | 9/2000 | Gray et al. | |
| 6,148,280 A | 11/2000 | Kramer | |
| 6,155,120 A | 12/2000 | Taylor | |
| 6,174,294 B1 | 1/2001 | Crabb et al. | |
| 6,195,921 B1 | 3/2001 | Truong | |
| 6,198,394 B1 | 3/2001 | Jacobsen et al. | |
| 6,226,577 B1 | 5/2001 | Yeo | |
| 6,266,623 B1 | 7/2001 | Vock et al. | |
| 6,287,200 B1 | 9/2001 | Sharma | |
| 6,298,314 B1 | 10/2001 | Blackadar et al. | |
| 6,305,100 B1 | 10/2001 | Komarnycky et al. | |
| 6,330,757 B1 | 12/2001 | Russell | |
| 6,336,365 B1 | 1/2002 | Blackadar et al. | |
| 6,356,856 B1 | 3/2002 | Damen et al. | |
| 6,357,147 B1 | 3/2002 | Darley et al. | |
| 6,360,597 B1 | 3/2002 | Hubbard, Jr. | |
| 6,426,490 B1 | 7/2002 | Storz | |
| 6,428,490 B1 | 8/2002 | Kramer et al. | |
| 6,430,843 B1 | 8/2002 | Potter et al. | |
| 6,493,652 B1 | 12/2002 | Ohlenbusch et al. | |
| 6,496,787 B1 | 12/2002 | Flentov et al. | |
| 6,496,952 B1 | 12/2002 | Osada et al. | |
| 6,498,994 B2 | 12/2002 | Vock et al. | |
| 6,515,284 B1 | 2/2003 | Walle et al. | |
| 6,516,284 B2 | 2/2003 | Flentov et al. | |
| 6,536,139 B2 | 3/2003 | Darley et al. | |
| 6,539,336 B1 | 3/2003 | Vock et al. | |
| 6,544,858 B1 | 4/2003 | Beekman et al. | |
| 6,560,903 B1 | 5/2003 | Darley | |
| 6,578,291 B2 | 6/2003 | Hirsch et al. | |
| 6,611,789 B1 | 8/2003 | Darley | |
| 6,640,144 B1 | 10/2003 | Huang et al. | |
| 6,656,042 B2 | 12/2003 | Reiss et al. | |
| 6,718,200 B2 | 4/2004 | Marmaropoulos et al. | |
| 6,739,200 B1 | 5/2004 | Norton | |
| 6,748,462 B2 | 6/2004 | Dubil et al. | |
| 6,778,973 B2 | 8/2004 | Harlan | |
| 6,785,579 B2 | 8/2004 | Huang et al. | |
| 6,785,805 B1 | 8/2004 | House et al. | |
| 6,808,462 B2 | 10/2004 | Snyder et al. | |
| 6,829,512 B2 | 12/2004 | Huang et al. | |
| 6,836,744 B1 * | 12/2004 | Asphahani | A43D 1/02 702/141 |
| 6,876,947 B1 | 4/2005 | Darley et al. | |
| 6,882,897 B1 | 4/2005 | Fernandez | |
| 6,885,971 B2 | 4/2005 | Vock et al. | |
| 6,889,282 B2 | 5/2005 | Schollenberger | |
| 6,892,216 B2 | 5/2005 | Coburn, II et al. | |
| 6,909,420 B1 | 6/2005 | Nicolas et al. | |
| 6,922,664 B1 | 7/2005 | Fernandez et al. | |
| 6,932,698 B2 | 8/2005 | Sprogis | |
| 6,959,259 B2 | 10/2005 | Vock et al. | |
| 6,963,818 B2 | 11/2005 | Flentov et al. | |
| 6,978,320 B2 | 12/2005 | Nonaka | |
| 7,030,861 B1 | 4/2006 | Westerman et al. | |
| 7,045,151 B2 | 5/2006 | Trant | |
| 7,046,151 B2 | 5/2006 | Dundon | |
| 7,054,784 B2 | 5/2006 | Flentov et al. | |
| 7,057,551 B1 | 6/2006 | Vogt | |
| 7,070,571 B2 | 7/2006 | Kramer et al. | |
| 7,072,789 B2 | 7/2006 | Vock et al. | |
| 7,092,846 B2 | 8/2006 | Vock et al. | |
| 7,152,343 B2 | 12/2006 | Whatley | |
| 7,162,392 B2 | 1/2007 | Vock et al. | |
| 7,171,331 B2 | 1/2007 | Vock et al. | |
| 7,200,517 B2 | 4/2007 | Darley et al. | |
| 7,219,449 B1 | 5/2007 | Hoffberg et al. | |
| 7,245,898 B2 | 7/2007 | Van Bosch et al. | |
| 7,277,021 B2 | 10/2007 | Beebe et al. | |
| 7,283,647 B2 | 10/2007 | McNitt | |
| 7,304,580 B2 | 12/2007 | Sullivan et al. | |

(56) References Cited

U.S. PATENT DOCUMENTS

| | | |
|---|---|---|
| 7,310,895 B2 | 12/2007 | Whittlesey et al. |
| 7,383,728 B2 | 6/2008 | Noble et al. |
| RE40,474 E | 9/2008 | Quellais et al. |
| 7,426,873 B1 | 9/2008 | Kholwadwala et al. |
| 7,428,471 B2 | 9/2008 | Darley et al. |
| 7,433,805 B2 | 10/2008 | Vock et al. |
| 7,457,724 B2 | 11/2008 | Vock et al. |
| 7,497,037 B2 | 3/2009 | Vick et al. |
| 7,498,856 B2 | 3/2009 | Lin et al. |
| 7,498,956 B2 | 3/2009 | Baier et al. |
| 7,522,970 B2 | 4/2009 | Fernandez |
| 7,552,549 B2 | 6/2009 | Whittlesey et al. |
| 7,579,946 B2 | 8/2009 | Case, Jr. |
| 7,596,891 B2 | 10/2009 | Carnes et al. |
| 7,602,301 B1 | 10/2009 | Stirling et al. |
| 7,607,243 B2 | 10/2009 | Berner, Jr. et al. |
| 7,617,068 B2 | 11/2009 | Tadin et al. |
| 7,623,987 B2 | 11/2009 | Vock et al. |
| 7,625,314 B2 | 12/2009 | Ungari et al. |
| 7,651,442 B2 | 1/2010 | Carlson |
| 7,658,694 B2 | 2/2010 | Ungari |
| 7,670,263 B2 | 3/2010 | Ellis et al. |
| 7,726,206 B2 | 6/2010 | Terrafranca, Jr. et al. |
| 7,726,994 B1 | 6/2010 | Willey |
| 7,739,076 B1 | 6/2010 | Vock et al. |
| 7,758,523 B2 | 7/2010 | Collings et al. |
| 7,771,320 B2 | 8/2010 | Riley et al. |
| 7,805,150 B2 | 9/2010 | Graham et al. |
| 7,816,632 B2 | 10/2010 | Bourke, III et al. |
| 7,840,378 B2 | 11/2010 | Vock et al. |
| 7,901,325 B2 | 3/2011 | Henderson |
| 7,905,815 B2 | 3/2011 | Ellis et al. |
| 7,909,737 B2 | 3/2011 | Ellis et al. |
| 7,921,716 B2 | 4/2011 | Morris Bamberg et al. |
| 7,934,983 B1 | 5/2011 | Eisner |
| 7,997,007 B2 | 8/2011 | Sanabria-Hernandez |
| 8,056,268 B2 | 11/2011 | DiBenedetto et al. |
| 8,061,061 B1 | 11/2011 | Rivas |
| 8,099,258 B2 | 1/2012 | Alten et al. |
| 8,131,498 B1 | 3/2012 | McCauley |
| 8,142,267 B2 | 3/2012 | Adams |
| 8,172,722 B2 | 5/2012 | Molyneux et al. |
| 8,212,158 B2 | 7/2012 | Wiest |
| 8,216,081 B2 | 7/2012 | Snyder et al. |
| 8,230,619 B2 | 7/2012 | Salvatelli et al. |
| 8,251,930 B2 | 8/2012 | Ido |
| 8,253,586 B1 | 8/2012 | Matak |
| 8,291,618 B2 | 10/2012 | Ellis |
| 8,333,643 B2 | 12/2012 | Eisner |
| 8,467,979 B2 | 6/2013 | Sobolewski |
| 8,474,153 B2 | 7/2013 | Brie et al. |
| 8,479,416 B2 | 7/2013 | Auger et al. |
| 8,484,654 B2 | 7/2013 | Graham et al. |
| 8,676,541 B2 | 3/2014 | Schrock et al. |
| 8,739,639 B2 | 6/2014 | Owings et al. |
| 8,870,795 B2 | 10/2014 | Kim et al. |
| 9,002,680 B2 | 4/2015 | Nurse et al. |
| 9,089,182 B2 | 7/2015 | Schrock et al. |
| 9,445,646 B2 | 9/2016 | Cook et al. |
| 9,462,844 B2 | 10/2016 | Schrock et al. |
| 9,642,415 B2 | 5/2017 | Pease et al. |
| 10,314,361 B2 | 6/2019 | Amos et al. |
| 2001/0003665 A1 | 6/2001 | Kim |
| 2001/0054043 A1 | 12/2001 | Harlan |
| 2002/0035184 A1 | 3/2002 | Plaver et al. |
| 2002/0133069 A1 | 9/2002 | Roberts |
| 2002/0134153 A1 | 9/2002 | Grenlund |
| 2003/0009308 A1 | 1/2003 | Kirtley |
| 2003/0054327 A1 | 3/2003 | Evensen |
| 2003/0097878 A1 | 5/2003 | Farringdon et al. |
| 2003/0163287 A1 | 8/2003 | Vock et al. |
| 2003/0207718 A1 | 11/2003 | Perlmutter |
| 2004/0078091 A1 | 4/2004 | Elkins |
| 2004/0148799 A1 | 8/2004 | Lussier et al. |
| 2004/0154190 A1 | 8/2004 | Munster |
| 2004/0162702 A1 | 8/2004 | Pandipati et al. |
| 2004/0215413 A1 | 10/2004 | Weldum et al. |
| 2004/0218317 A1 | 11/2004 | Kawazu et al. |
| 2004/0225467 A1 | 11/2004 | Vock et al. |
| 2004/0226192 A1 | 11/2004 | Geer et al. |
| 2005/0011085 A1 | 1/2005 | Swigart et al. |
| 2005/0032582 A1 | 2/2005 | Mahajan et al. |
| 2005/0046576 A1 | 3/2005 | Julian et al. |
| 2005/0106977 A1 | 5/2005 | Coulston |
| 2005/0183292 A1 | 8/2005 | DiBenedetto et al. |
| 2005/0184848 A1 | 8/2005 | Yoshida et al. |
| 2005/0184878 A1 * | 8/2005 | Grold ............... A43B 3/34 482/79 |
| 2005/0188566 A1 | 9/2005 | Whittlesey et al. |
| 2005/0221403 A1 | 10/2005 | Gazenko |
| 2005/0261609 A1 | 11/2005 | Collings et al. |
| 2005/0282633 A1 | 12/2005 | Nicolas et al. |
| 2006/0000420 A1 | 1/2006 | Martin Davies |
| 2006/0010174 A1 | 1/2006 | Nguyen et al. |
| 2006/0017692 A1 | 1/2006 | Wehrenberg et al. |
| 2006/0025229 A1 | 2/2006 | Mahajan et al. |
| 2006/0026120 A1 | 2/2006 | Carolan et al. |
| 2006/0053656 A1 | 3/2006 | Kumle |
| 2006/0082977 A1 | 4/2006 | Kim |
| 2006/0091715 A1 | 5/2006 | Schmitz et al. |
| 2006/0143645 A1 | 6/2006 | Vock et al. |
| 2006/0144152 A1 | 7/2006 | Cabuz et al. |
| 2006/0217231 A1 | 9/2006 | Parks et al. |
| 2006/0226843 A1 | 10/2006 | Al-Anbuky et al. |
| 2006/0248749 A1 | 11/2006 | Ellis |
| 2006/0262120 A1 | 11/2006 | Rosenberg |
| 2006/0270951 A1 | 11/2006 | Ikeuchi |
| 2006/0282017 A1 | 12/2006 | Avni et al. |
| 2006/0283050 A1 | 12/2006 | Carnes et al. |
| 2007/0000154 A1 | 1/2007 | DiBenedetto et al. |
| 2007/0006489 A1 | 1/2007 | Case et al. |
| 2007/0016091 A1 | 1/2007 | Butt et al. |
| 2007/0026421 A1 | 2/2007 | Sundberg et al. |
| 2007/0032748 A1 | 2/2007 | McNeil et al. |
| 2007/0033838 A1 | 2/2007 | Luce et al. |
| 2007/0039289 A1 | 2/2007 | LeCompte |
| 2007/0060408 A1 | 3/2007 | Schultz et al. |
| 2007/0063849 A1 | 3/2007 | Rosella et al. |
| 2007/0063850 A1 | 3/2007 | Devaul et al. |
| 2007/0067885 A1 | 3/2007 | Fernandez |
| 2007/0068244 A1 | 3/2007 | Billing et al. |
| 2007/0072158 A1 | 3/2007 | Unuma et al. |
| 2007/0073178 A1 | 3/2007 | Browning et al. |
| 2007/0078324 A1 | 4/2007 | Wijisiriwardana |
| 2007/0082389 A1 | 4/2007 | Clark et al. |
| 2007/0094890 A1 | 5/2007 | Cho et al. |
| 2007/0118328 A1 | 5/2007 | Vock et al. |
| 2007/0130287 A1 | 6/2007 | Kumar et al. |
| 2007/0143452 A1 | 6/2007 | Suenbuel et al. |
| 2007/0152812 A1 | 7/2007 | Wong et al. |
| 2007/0157488 A1 | 7/2007 | Guzman |
| 2007/0173705 A1 | 7/2007 | Teller et al. |
| 2007/0186446 A1 | 8/2007 | Lafortune |
| 2007/0204687 A1 | 9/2007 | Haselhurst et al. |
| 2007/0208544 A1 | 9/2007 | Kulach et al. |
| 2007/0232455 A1 | 10/2007 | Hanoun |
| 2007/0250286 A1 | 10/2007 | Duncan et al. |
| 2007/0260421 A1 | 11/2007 | Berner et al. |
| 2007/0261271 A1 | 11/2007 | Krouse |
| 2007/0283599 A1 * | 12/2007 | Talbott ............. A43B 13/145 36/31 |
| 2008/0027679 A1 | 1/2008 | Shklarski |
| 2008/0028783 A1 | 2/2008 | Immel et al. |
| 2008/0039203 A1 | 2/2008 | Ackley et al. |
| 2008/0048616 A1 | 2/2008 | Paul et al. |
| 2008/0056508 A1 | 3/2008 | Pierce et al. |
| 2008/0058126 A1 | 3/2008 | House |
| 2008/0060220 A1 | 3/2008 | Lyden |
| 2008/0060224 A1 | 3/2008 | Whittlesey et al. |
| 2008/0061023 A1 | 3/2008 | Moor |
| 2008/0066343 A1 | 3/2008 | Sanabria-Hernandez |
| 2008/0066560 A1 | 3/2008 | Yu et al. |
| 2008/0127527 A1 | 6/2008 | Chen |
| 2008/0134583 A1 | 6/2008 | Polus |

(56) References Cited

U.S. PATENT DOCUMENTS

| | | |
|---|---|---|
| 2008/0165140 A1 | 7/2008 | Christie et al. |
| 2008/0172498 A1 | 7/2008 | Boucard |
| 2008/0177507 A1 | 7/2008 | Mian et al. |
| 2008/0188353 A1 | 8/2008 | Vitolo et al. |
| 2008/0200312 A1 | 8/2008 | Tagliabue |
| 2008/0203144 A1 | 8/2008 | Kim |
| 2008/0218310 A1 | 9/2008 | Alten et al. |
| 2008/0221403 A1 | 9/2008 | Fernandez |
| 2008/0246629 A1 | 10/2008 | Tsui et al. |
| 2008/0255794 A1 | 10/2008 | Levine |
| 2008/0258921 A1* | 10/2008 | Woo .............. A63B 24/0062 482/8 |
| 2008/0259028 A1 | 10/2008 | Teepell et al. |
| 2008/0269644 A1 | 10/2008 | Ray |
| 2008/0287832 A1 | 11/2008 | Collins et al. |
| 2008/0289217 A1 | 11/2008 | Horvath |
| 2008/0293023 A1 | 11/2008 | Diehl et al. |
| 2008/0297832 A1 | 12/2008 | Otsuka |
| 2008/0306410 A1 | 12/2008 | Kalpaxis et al. |
| 2008/0307899 A1 | 12/2008 | Von Lilienfeld-Toal et al. |
| 2008/0318679 A1 | 12/2008 | Tran et al. |
| 2009/0018691 A1 | 1/2009 | Fernandez |
| 2009/0027917 A1 | 1/2009 | Chen et al. |
| 2009/0048538 A1 | 2/2009 | Levine et al. |
| 2009/0061837 A1 | 3/2009 | Chaudhri et al. |
| 2009/0075347 A1 | 3/2009 | Cervin et al. |
| 2009/0075781 A1 | 3/2009 | Schwarzberg et al. |
| 2009/0076341 A1 | 3/2009 | James et al. |
| 2009/0105047 A1 | 4/2009 | Guidi et al. |
| 2009/0107009 A1 | 4/2009 | Bishop et al. |
| 2009/0109659 A1 | 4/2009 | Harris |
| 2009/0135001 A1 | 5/2009 | Yuk |
| 2009/0137933 A1 | 5/2009 | Lieberman et al. |
| 2009/0149299 A1 | 6/2009 | Tchao et al. |
| 2009/0150178 A1 | 6/2009 | Sutton et al. |
| 2009/0152456 A1 | 6/2009 | Waid et al. |
| 2009/0153369 A1 | 6/2009 | Baier et al. |
| 2009/0153477 A1 | 6/2009 | Saenz |
| 2009/0163287 A1 | 6/2009 | Vald'Via et al. |
| 2009/0163322 A1 | 6/2009 | Andren et al. |
| 2009/0167677 A1 | 7/2009 | Kruse et al. |
| 2009/0171614 A1 | 7/2009 | Damen |
| 2009/0259566 A1 | 10/2009 | White et al. |
| 2009/0262088 A1 | 10/2009 | Moll-Carrillo et al. |
| 2009/0293319 A1 | 12/2009 | Avni |
| 2009/0297832 A1 | 12/2009 | Hatta et al. |
| 2010/0000121 A1 | 1/2010 | Brodie et al. |
| 2010/0004566 A1 | 1/2010 | Son et al. |
| 2010/0009810 A1 | 1/2010 | Trzecieski |
| 2010/0023231 A1 | 1/2010 | Allgaier et al. |
| 2010/0023531 A1 | 1/2010 | Brisebois et al. |
| 2010/0035688 A1 | 2/2010 | Picunko |
| 2010/0053867 A1 | 3/2010 | Ellis et al. |
| 2010/0056340 A1 | 3/2010 | Ellis et al. |
| 2010/0057951 A1 | 3/2010 | Ellis et al. |
| 2010/0059561 A1 | 3/2010 | Ellis et al. |
| 2010/0062740 A1 | 3/2010 | Ellis et al. |
| 2010/0063778 A1 | 3/2010 | Schrock et al. |
| 2010/0063779 A1 | 3/2010 | Schrock et al. |
| 2010/0065836 A1 | 3/2010 | Lee |
| 2010/0072948 A1 | 3/2010 | Sun et al. |
| 2010/0082735 A1 | 4/2010 | Petersen et al. |
| 2010/0088023 A1 | 4/2010 | Werner |
| 2010/0094147 A1 | 4/2010 | Inan et al. |
| 2010/0111705 A1 | 5/2010 | Sato et al. |
| 2010/0113160 A1 | 5/2010 | Belz et al. |
| 2010/0129780 A1 | 5/2010 | Homsi et al. |
| 2010/0152619 A1 | 6/2010 | Kalpaxis et al. |
| 2010/0152630 A1 | 6/2010 | Matsuoka et al. |
| 2010/0170117 A1 | 7/2010 | Kim |
| 2010/0184563 A1 | 7/2010 | Molyneux et al. |
| 2010/0184564 A1 | 7/2010 | Molyneux et al. |
| 2010/0191490 A1 | 7/2010 | Martens et al. |
| 2010/0199518 A1 | 8/2010 | Buttigieg |
| 2010/0201500 A1 | 8/2010 | Stirling et al. |
| 2010/0201512 A1 | 8/2010 | Stirling et al. |
| 2010/0204616 A1 | 8/2010 | Shears et al. |
| 2010/0225763 A1 | 9/2010 | Vock et al. |
| 2010/0231580 A1 | 9/2010 | Miyasaka |
| 2010/0285929 A1 | 11/2010 | Bayerlein et al. |
| 2010/0286601 A1 | 11/2010 | Yodfat et al. |
| 2010/0292599 A1 | 11/2010 | Oleson et al. |
| 2010/0298659 A1 | 11/2010 | McCombie et al. |
| 2010/0312083 A1 | 12/2010 | Southerland |
| 2010/0332188 A1 | 12/2010 | Vock et al. |
| 2011/0003665 A1 | 1/2011 | Burton et al. |
| 2011/0021280 A1 | 1/2011 | Boroda et al. |
| 2011/0054359 A1 | 3/2011 | Sazonov et al. |
| 2011/0054809 A1 | 3/2011 | Templeman |
| 2011/0087445 A1 | 4/2011 | Sobolewski |
| 2011/0107369 A1 | 5/2011 | O'Brien et al. |
| 2011/0119027 A1 | 5/2011 | Zhu et al. |
| 2011/0119058 A1 | 5/2011 | Berard et al. |
| 2011/0136627 A1 | 6/2011 | Williams |
| 2011/0152695 A1 | 6/2011 | Granqvist et al. |
| 2011/0167678 A1 | 7/2011 | Peikert |
| 2011/0203390 A1 | 8/2011 | Tao et al. |
| 2011/0208444 A1 | 8/2011 | Solinsky |
| 2011/0214501 A1 | 9/2011 | Ross et al. |
| 2012/0035509 A1 | 2/2012 | Wilson et al. |
| 2012/0041767 A1 | 2/2012 | Hoffman et al. |
| 2012/0050351 A1 | 3/2012 | Dobler et al. |
| 2012/0050529 A1 | 3/2012 | Bentley |
| 2012/0059432 A1 | 3/2012 | Emborg et al. |
| 2012/0089330 A1 | 4/2012 | Hesch et al. |
| 2012/0166091 A1 | 6/2012 | Kim et al. |
| 2012/0234111 A1 | 9/2012 | Molyneux et al. |
| 2012/0291563 A1 | 11/2012 | Schrock et al. |
| 2012/0291564 A1 | 11/2012 | Amos et al. |
| 2013/0002533 A1 | 1/2013 | Burroughs et al. |
| 2013/0019694 A1 | 1/2013 | Molyneux et al. |
| 2013/0061494 A1 | 3/2013 | Linth |
| 2013/0079907 A1 | 3/2013 | Homsi et al. |
| 2013/0110264 A1 | 5/2013 | Weast et al. |
| 2013/0165820 A1 | 6/2013 | Lin et al. |
| 2013/0171599 A1* | 7/2013 | Bleich .............. G16H 20/30 434/247 |
| 2013/0190903 A1 | 7/2013 | Balakrishnan et al. |
| 2013/0213145 A1 | 8/2013 | Owings et al. |
| 2013/0213146 A1 | 8/2013 | Amos et al. |
| 2013/0213147 A1 | 8/2013 | Rice et al. |
| 2013/0225309 A1 | 8/2013 | Bentley et al. |
| 2014/0033572 A1 | 2/2014 | Steier et al. |
| 2014/0174205 A1 | 6/2014 | Clarke et al. |
| 2014/0222173 A1 | 8/2014 | Giedwoyn et al. |
| 2014/0259779 A1 | 9/2014 | Hashish et al. |
| 2014/0277631 A1 | 9/2014 | Rice et al. |
| 2014/0350435 A1 | 11/2014 | Lam |
| 2015/0177081 A1 | 6/2015 | Steier |
| 2015/0257475 A1 | 9/2015 | Langvin et al. |
| 2016/0242500 A1 | 8/2016 | Langvin et al. |
| 2016/0345663 A1 | 12/2016 | Walker et al. |
| 2017/0079374 A1 | 3/2017 | Farris et al. |
| 2017/0284875 A1 | 10/2017 | Walker |
| 2017/0306539 A1 | 10/2017 | Gladish et al. |

FOREIGN PATENT DOCUMENTS

| | | |
|---|---|---|
| CN | 1101757A A | 4/1995 |
| CN | 1213520 A | 4/1999 |
| CN | 1839724 A | 10/2006 |
| CN | 200977748Y Y | 11/2007 |
| CN | 200994779 Y | 12/2007 |
| CN | 101111743 A | 1/2008 |
| CN | 101116561 A | 2/2008 |
| CN | 101240461 A | 8/2008 |
| CN | 101242880 A | 8/2008 |
| CN | 101367012 A | 2/2009 |
| CN | 101479572 A | 7/2009 |
| CN | 101516223 A | 8/2009 |
| CN | 101524196 A | 9/2009 |
| CN | 201303173 Y | 9/2009 |
| CN | 100584234 C | 1/2010 |
| CN | 101784230 A | 7/2010 |

(56) References Cited

FOREIGN PATENT DOCUMENTS

| | | |
|---|---|---|
| CN | 101890215 A | 11/2010 |
| CN | 101894206 A | 11/2010 |
| CN | 102143695 A | 8/2011 |
| CN | 201948063 U | 8/2011 |
| CN | 102266140 A | 12/2011 |
| DE | 370480 C | 3/1923 |
| DE | 10201134 A1 | 7/2003 |
| EP | 0160880 A1 | 11/1985 |
| EP | 239220 A1 | 9/1987 |
| EP | 0662600 A1 | 7/1995 |
| EP | 1524922 A1 | 4/2005 |
| EP | 1707065 A1 | 10/2006 |
| EP | 2189191 A2 | 5/2010 |
| FR | 2929827 A1 | 10/2009 |
| GB | 251054 A | 4/1926 |
| GB | 2280995 A | 2/1995 |
| GB | 2421416 A | 6/2006 |
| JP | S5499184 A | 8/1979 |
| JP | S54146039 A | 11/1979 |
| JP | S55072354 U | 5/1980 |
| JP | S5616302 U | 2/1981 |
| JP | 5664301 | 5/1981 |
| JP | S56174468 U | 12/1981 |
| JP | S60234603 A | 11/1985 |
| JP | S61176429 U | 11/1986 |
| JP | H023020 A | 1/1990 |
| JP | H0355077 A | 3/1991 |
| JP | H03114209 U | 11/1991 |
| JP | 0561724 | 6/1993 |
| JP | H06014803 A | 1/1994 |
| JP | H0641505 U | 6/1994 |
| JP | H06336967 A | 12/1994 |
| JP | H08089482 A | 4/1996 |
| JP | H10241648 A | 9/1998 |
| JP | 3036281 B2 | 4/2000 |
| JP | 2000516509 A | 12/2000 |
| JP | 2001028260 A | 1/2001 |
| JP | 2001351591 A | 12/2001 |
| JP | 2002131155 A | 5/2002 |
| JP | 2002163404 A | 6/2002 |
| JP | 2003061779 A | 3/2003 |
| JP | 2003236002 A | 8/2003 |
| JP | 2004028674 A | 1/2004 |
| JP | 2004158242 A | 6/2004 |
| JP | 2004267784 A | 9/2004 |
| JP | 2005019305 A | 1/2005 |
| JP | 2005079019 A | 3/2005 |
| JP | 2005507678 A | 3/2005 |
| JP | 2005156531 A | 6/2005 |
| JP | 2005270640 A | 10/2005 |
| JP | 2005532138 A | 10/2005 |
| JP | 2006086072 A | 3/2006 |
| JP | 2006521879 A | 9/2006 |
| JP | 2006280955 A | 10/2006 |
| JP | 2007134473 A | 5/2007 |
| JP | 200715117 | 6/2007 |
| JP | 2008166066 A | 7/2008 |
| JP | 20083752 A | 10/2008 |
| JP | 2009148338 A | 7/2009 |
| JP | 2009158401 A | 7/2009 |
| JP | 2009535157 A | 10/2009 |
| JP | 2010088886 A | 4/2010 |
| JP | 2010517725 A | 5/2010 |
| JP | 2011105138 A | 6/2011 |
| JP | 2011112938 A | 6/2011 |
| JP | 2011120740 A | 6/2011 |
| JP | 2011524207 A | 9/2011 |
| JP | 2011196931 A | 10/2011 |
| JP | 2012065942 A | 4/2012 |
| JP | 2012115709 A | 6/2012 |
| JP | 2012524638 A | 10/2012 |
| JP | 2013106773 A | 6/2013 |
| JP | 2013528102 A | 7/2013 |
| JP | 2013528103 A | 7/2013 |
| JP | 2013537436 A | 10/2013 |
| JP | 2014505577 A | 3/2014 |
| JP | 2015512674 A | 4/2015 |
| KR | 20010035162 A | 5/2001 |
| KR | 20010079094 A | 8/2001 |
| KR | 100386788 B1 | 6/2003 |
| KR | 20050032119 | 4/2005 |
| KR | 20060021632 | 3/2006 |
| KR | 20060034353 A | 4/2006 |
| KR | 20090052762 A | 5/2009 |
| KR | 20090102550 | 9/2009 |
| KR | 20100012845 U | 12/2010 |
| KR | 20100127148 A | 12/2010 |
| KR | 20100130860 A | 12/2010 |
| KR | 20110071728 A | 6/2011 |
| KR | 20110124964 A | 11/2011 |
| KR | 20120130306 A | 11/2012 |
| KR | 20130130051 | 11/2013 |
| KR | 20140004206 A | 1/2014 |
| KR | 20167008215 | 3/2016 |
| NO | 03045239 A1 | 6/2003 |
| NO | 2009027917 A1 | 3/2009 |
| WO | 9010204 A1 | 9/1990 |
| WO | 98007341 A2 | 2/1998 |
| WO | 200033031 A1 | 6/2000 |
| WO | 2002035184 A2 | 5/2002 |
| WO | 03000355 A1 | 1/2003 |
| WO | 2006035469 A2 | 4/2006 |
| WO | 2006065679 A2 | 6/2006 |
| WO | 2006067434 A1 | 6/2006 |
| WO | 2006091715 A1 | 8/2006 |
| WO | 2007064735 A2 | 6/2007 |
| WO | 2007082389 A1 | 7/2007 |
| WO | 2007128049 A1 | 11/2007 |
| WO | 2007130287 A2 | 11/2007 |
| WO | 2008061023 A2 | 5/2008 |
| WO | 2008101085 A2 | 8/2008 |
| WO | 2008134583 A1 | 11/2008 |
| WO | 2009126818 A2 | 10/2009 |
| WO | 2009152456 A2 | 12/2009 |
| WO | 2010065836 A2 | 6/2010 |
| WO | 2010065886 A1 | 6/2010 |
| WO | 2010111705 A2 | 9/2010 |
| WO | 2011157607 A1 | 12/2011 |
| WO | 2012021507 A2 | 2/2012 |
| WO | 2012061804 A1 | 5/2012 |
| WO | 2012109244 A1 | 8/2012 |
| WO | 2012112930 A1 | 8/2012 |
| WO | 2012112931 A2 | 8/2012 |
| WO | 2012112934 A2 | 8/2012 |
| WO | 2012112938 A2 | 8/2012 |
| WO | 2012143274 A2 | 10/2012 |
| WO | 2013010171 A1 | 1/2013 |

OTHER PUBLICATIONS

Jul. 21, 2022 (EP)—Extended European Search Report—App. No. 22161306.0.
Nov. 14, 2022—(EP) EESR—App. No. 22188345.7.
Razak et al., "Foot Plantar Pressure Measurement System: a Review," Sensors 2012, vol. 12, No. 12, Jul. 23, 2012, whole document.
Kliskey, "Recreation terrain suitability mapping: a spatially explicit methodology for determining recreation potential for resource use assessment," Landscape and Urban Planning, vol. 52, No. 1, Nov. 15, 2000, pp. 33-43.
Aug. 7, 2013—(WO) ISR and WO—App. No. PCT/US2013/027397.
Aug. 21, 2012—(WO) ISR & WO—App. No. PCT/US2012/025717.
Jul. 11, 2012—(WO) ISR & WO App No. PCT/US2012/025709.
Aug. 21, 2013—(WO) International Preliminary Report on Patentability App No. PCT/US2012/025713.
Dec. 11, 2009—(WO) ISR and WO App No. PCT/2009/047246.
Morris, Stacy J., A Shoe-Integrated Sensor System for Wireless Gait Analysis and Real-Time Therapeutic Feedback, dissertation, 2004, pp. 1-314, Massachusetts Institute of Technology, MA.
May 28, 2013—(WO) ISR & WO App No. PCT/US2013/027421.

(56) References Cited

OTHER PUBLICATIONS

Fleming et al., Athlete and Coach Perceptions of Technology Needs for Evaluating Running Performance, article, Aug. 14, 2010, 18 pages, 13:1-18, UK.
Salpavaara, et al. Wireless Insole Sensor System for Plantar Force Measurements during Sports Events, article, Sep. 6-11, 2009, XIX IMEKO World Congress, Fundamental and Applied Metrology, 6 pages, Lisbon, Portugal.
Mar. 7, 2012—(WO) ISR and WO—App. PCT/US2011/060187.
Jul. 15, 2013—(WO) Search Report and Written Opinion—App. No. PCT/US2013/022219.
Lovell, "A system for real-time gesture recognition and classification of coordinated motion," Massachusetts Institute of Technology, Dept. of Electrical Engineering and Computer Science, 2005, <http://dspace.mit.edu/handle/1721.1/33290> (2 pages).
Chee et al., "A low cost wearable wireless sensing system for upper limb home rehabilitation," Robotics Automation and Mechatronics (RAM) 2010 IEEE Conference on Jun. 28-30, 2010; Abstract printout (1 page).
Guraliuc et al., "Channel model for on the body communication along and around the human torso at 2.4Ghz and 5.8Ghz," Antenna Technology (IWAT), 2010 International Workshop on Mar. 1-3, 2010; Abstract printout (1 page).
Jun. 21, 2012—(WO) ISR—App No. PCT/US2012/025701.
Frazier, Karen, "How Many Calories to 1 Carb?" published Nov. 12, 2010, Livestrong.com, 3 pages.
Oct. 1, 2013—(WO) ISR and WO—App No. PCT/US2013/048157.
Llosa et al., "Design of a Motion Detector to Monitor Rowing Performance Based on Wireless Sensor Networks," Intelligent Networking and Collaborative Systems, 2009, http://ieeexplore.ieee.org/xpl/freeabs_all.jsp?arnumber=5369324 (1 page).
Choquette et al., "Accelerometer-based wireless body area network to estimate intensity of therapy in post-acute rehabilitation," Journal of NeuroEngineering and Rehabilitation 2008, http://www.jneuroengrehab.com/content/5/1/20/abstract (1 page).
Morris, "A shoe-integrated sensor system for wireless gait analysis and real-time therapeutic feedback," Harvard-MIT Division of Health Sciences and Technology, 2004,http://dspace.mitedu/handle/1721.1/28601 (3 pages).
Lapinski, "A wearable, wireless sensor system for sports medicine," Massachusetts Institute of Technology, School of Architecture and Planning, Program in Media Arts and Sciences, 2008, http://dspace.mit.edulhandle/1721.1/46581(3 pages).
Aylward, "Sensemble : a wireless inertial sensor system for the interactive dance and collective motion analysis," Massachusetts Institute of Technology, School of Architecture and Planning, Program in Media Arts and Sciences, 2006, http://dspace.mitedu/handle/1721.1/37391 (3 pages).
Danko; How to Work a Nike Sensor; Dec. 26, 2010; eHow website; 4 pages.
Coyne; Stout's Shoes on Mass Ave Oldest Shoe Store in the USA; Jun. 18, 2013; FunCityFinder website; 5 pages.
Oct. 15, 2015—(EP) Office Action—App 14718257.0.
Davis, The Re-emergence of the Minimal Running Shoe, Clinical Commentary, Journal of Orthopaedic & Sports Physical Therapy, vol. 44, No. 10, pp. 775-784, Oct. 2014.
Lim, Joo-Tack, STO Ltd., Final Report on IT development cooperative project, "Development of IT running shoes that an transmit athletic information of the shoes when running and development of receiver technology," Ministry of Knowledge Economy (Institute for Information Technology Advancement (ITA)) (Jun. 30, 2009).
Aug. 9, 2016—(EP) Extended Search Report—App. No. 16170589.2.
Sep. 1, 2016—(EP) Extended Search Report—App. No. 16167470.0.
Sep. 25, 2012—(WO) ISR & WO, App. No. PCT/US12/025713.
Mar. 15, 2017—(EP) ESR—App. No. 16199665.7.
May 8, 2017—(EP) ESR)—App. No. 160201640.
Sep. 25, 2009—(WO) Partial ISR—App. No. PCT/US09/047246.
Dec. 11, 2009—(WO) ISR—App. No. PCT/US09/047246.
May 28, 2013—(WO) Partial ISR—App. No. PCT/US13/027397.
Aug. 7, 2013—(WO) ISR—App. No. PCT/US13/027397.
Jul. 16, 2014—(WO) ISR—App. No. PCT/US14/026225.
Mar. 5, 2013—(WO) ISR & WO—App. No. PCT/US12/025710.
Apr. 3, 2017—(EP) ESR—App. No. 16201636.4.
Sep. 6, 2019—(EP) ESR—App. No. 18209688.3.
Hanlon et al., Real-time gait even detection using wearable sensors, 2009, Gait & Posture, pp. 523-527 (Year: 2009).
Feb. 25, 2020—(EP) ESR—App. No. 19208716.1.

* cited by examiner

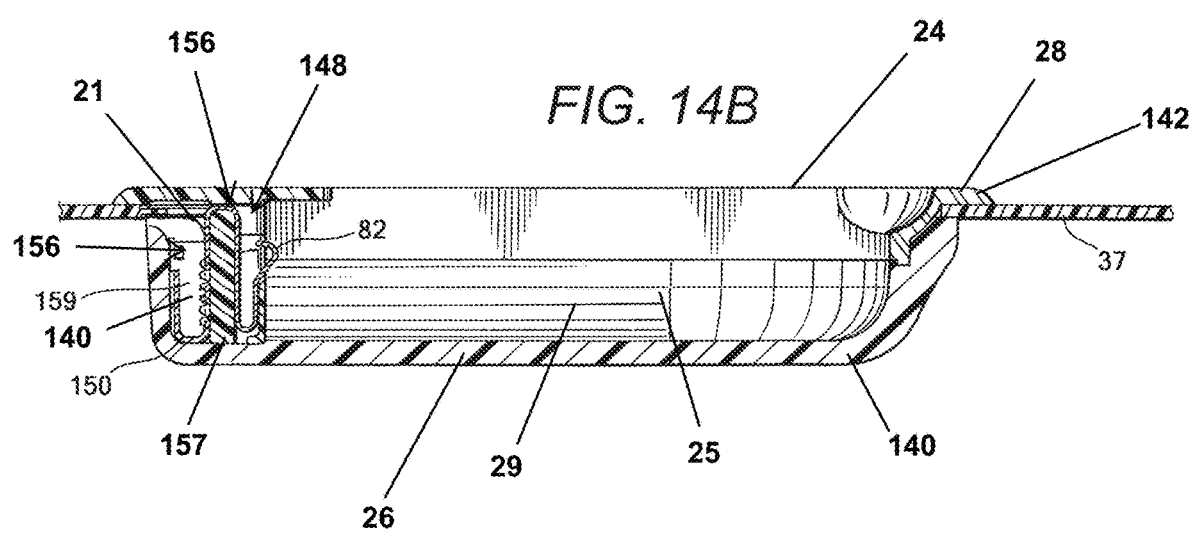

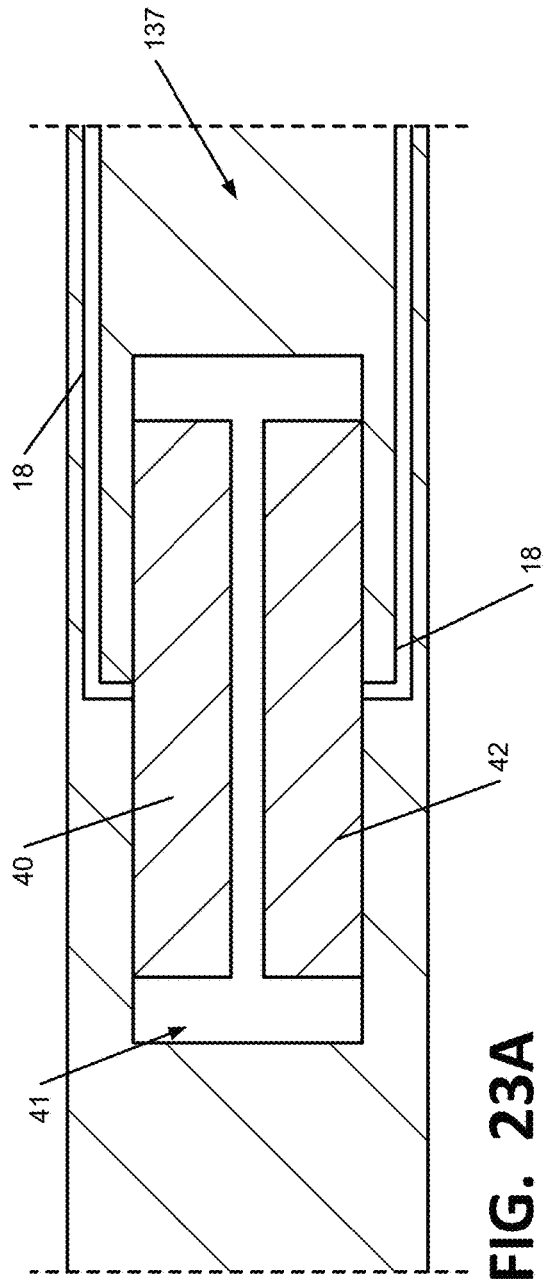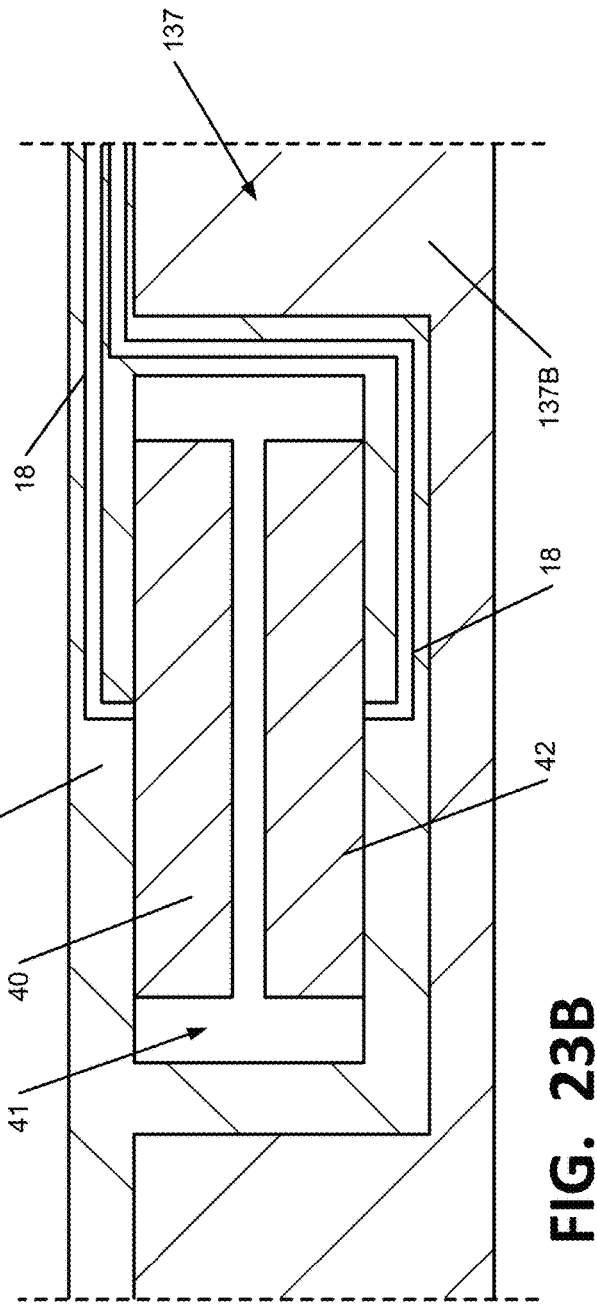

SYSTEM AND METHOD FOR ANALYZING ATHLETIC ACTIVITY

CROSS-REFERENCE TO RELATED APPLICATION

This application is a continuation of U.S. patent application Ser. No. 14/717,627, filed May 20, 2015, which is a continuation-in-part of U.S. patent application Ser. No. 13/757,417, filed Feb. 1, 2013. This application claims priority to and the benefit of such applications, which are incorporated by reference herein in their entirety

TECHNICAL FIELD

The present invention generally relates to systems, apparatuses, and methods for analyzing athletic activity and, more particularly, to systems, apparatuses, and methods for providing coaching feedback to a user based on analysis of athletic activity, e.g., when transitioning to a new footwear type, which may utilize data input from a sensor system incorporated into an article of footwear or other article of apparel.

BACKGROUND

Systems for analysis of athletic activity that utilize data collected from athletic activity are known. Such data can be analyzed and presented to a user in a number of different forms and formats, including by indication of performance metrics. However, uses for such athletic activity data and metrics can be unnecessarily limited. As one example, such data and performance metrics are often limited in providing active, real-time feedback and/or forward-looking feedback to the user. Accordingly, while certain systems for analyzing athletic activity provide a number of advantageous features, they nevertheless have certain limitations. The systems, apparatuses, and methods disclosed herein seek to overcome certain of these limitations and other drawbacks of the prior art, and to provide new features not heretofore available.

Recent trends and changes in footwear have created a need for systems for transitioning a wearer to a new footwear type. For example, minimal footwear is designed to mimic barefoot running by implementing less cushioning and stability than traditional running shoes, and often with no drop between the heel and forefoot, no arch support, no midsole, and either no heel counter or a flexible heel counter. Minimal footwear has gained popularity by promoting a natural motion of the foot that results in fewer injuries. However, transitioning from traditional footwear to minimal footwear may take time and proper instruction for the avoidance of injuries and other problems. Runners who incorporate minimal footwear into their running programs without any alteration in running volume or any preparation of their foot and ankle musculature have been found to be more prone to injuries. This is likely because most traditional shoe wearers have a more posterior strike pattern (e.g., a heel footstrike pattern), a higher vertical impact peak, greater dorsiflexion of the foot and less knee flexion at foot strike compared with preferred minimal footstrike pattern. Studies have found that wearers transitioning from traditional to minimal footwear often did not sufficiently alter their leg and foot biomechanics to properly adapt to the minimal footwear conditions. Injuries are considered likely due to poor transitioning as opposed to the minimal footwear itself. Accordingly, switching between traditional and minimal running shoes requires proper transitioning for the avoidance of injuries.

BRIEF SUMMARY

The present invention relates generally to a system for transitioning from a first footwear type to a second footwear type that is used with an article of footwear of the second footwear type including a sensor system with a plurality of force sensors engaged with the article of footwear and configured to sense force exerted by a user's foot, an electronic module configured for collecting data based on force input from the sensors and for wirelessly transmitting the data generated by the sensor system. The system also includes an electronic device in communication with the electronic module. The electronic device includes a processor that is configured to receive the data from the electronic module, compare the data to a footstrike template corresponding to a desired footstrike pattern of a footwear transitional program to determine whether a deviation from the footstrike template exists, and generate an indication to the user when the deviation from the desired footstrike pattern is determined to exist. The desired footstrike pattern corresponds to a preferred footstrike of the second footwear type. According to an aspect, the second footwear type is a minimal footwear and the desired footstrike pattern is a midfoot or forefoot strike pattern. The indication may further include a degree of deviation from the footstrike template. The indication may be visual, audible, tactile, and/or other type of indication.

According to one aspect, the electronic device is further configured for recording a plurality of data points for the user during an athletic activity session and providing feedback to the user based on data recorded during the athletic activity session. The feedback provided to the user may include a suggested activity report for a subsequent athletic activity and/or a suggested stretching activity.

According to another aspect, the electronic device is further configured for recording a plurality of athletic activity sessions for a user and modifying a duration of the transitional program based on at least one of an amount or number of recorded deviations, a total time of recorded data, and a total distance of recorded data. The electronic device may further be configured for receiving a user input corresponding to a perceived discomfort during an athletic activity.

According to another aspect, the footwear transitional program is customizable by a user type and may be based on at least one of age, weight, gender, excursion distance and speed. The footwear transitional program may include a plurality of desired footstrike patterns varying throughout the footwear transitional program, with a final desired footstrike pattern corresponding to a most preferred footstrike for the second footwear type and the electronic device may vary the desired footstrike pattern after a designated amount of usage. The deviation may be determined to exist if the degree of deviation is determined to exceed a predetermined threshold.

According to another aspect, generating the indication includes transmitting a signal to a second electronic device, where the signal is configured to cause the second electronic device to generate the indication.

According to a further aspect, comparing the data to the footstrike template includes detecting a footstrike pattern based on analysis of the data and comparing the footstrike pattern to the footstrike template. In one embodiment, the plurality of sensors are located in different locations on the article of footwear, and the footstrike pattern is detected based on the sequence of the forces sensed by the sensors and/or the level of the forces sensed by the sensors. In another embodiment, the plurality of sensors are further configured to measure a pressure distribution under the foot and the electronic device is further configured for comparing pressure distribution data to a foot pressure template.

According to yet another aspect, the system further includes a GPS module configured for detecting the user's position, where the GPS module is in communication with the electronic device. The GPS module may be located within the electronic device, within the electronic module, or elsewhere. The electronic device is further configured for generating an indication of the user's position to the user based on communication with the GPS module. In one embodiment, where the GPS module is located within the electronic module, the electronic device is further configured for receiving position information regarding the user's position from the electronic module and generating the indication of the user's position to the user based on the position information. In another embodiment, the electronic device may be further configured for receiving environmental information related to the user's position, which may be obtained by communication with an external server or other device, and for communicating the environmental information to the user, such as by video and/or audio display. Such environmental information may be used for presenting a suggested travel route to the user based on the environmental information. In a further embodiment, the electronic device may further be configured for receiving terrain information related to the user's position and altering the footstrike template based on the terrain information. Such terrain information may also be obtained by communication with an external server or other device.

According to a further aspect, the system further includes a leg sensor system configured to sense force exerted on a leg of a user and operably connected to the electronic device. The electronic device is further configured to compare the sensed force to a biomechanical movement template, the biomechanical movement template corresponding to a desired biomechanical leg movement pattern of the footwear transitional program, to determine whether a deviation from the biomechanical movement template exists and to generate an indication to the user when the deviation from the desired biomechanical leg movement pattern is determined to exist. In some examples, the indication further includes a degree of deviation from the biomechanical movement template.

According to a still further aspect, the electronic device may alter the footstrike template after a designated amount of usage, such as a designated amount of time or a designated running distance.

Additional aspects of the invention relate to a system for analyzing athletic activity that may be used in connection with a sensor system including a plurality of force sensors configured to be engaged with an article of footwear and configured to sense force exerted by a user's foot and an electronic device in communication with the sensor system. The electronic device is configured to receive data generated by the sensor system, analyze the data to determine whether a deviation from a desired footstrike pattern exists, and generate an indication to the user when the deviation from the desired footstrike pattern is determined to exist, wherein the indication comprises at least one of a visual indication, an audible indication, and a tactile indication. Any of the various aspects described above may be used in connection with this system.

Further aspects of the invention relate to a computer-assisted method for transitioning from a first footwear type to a second footwear type. The method may include receiving data, at a processor of an electronic device, from a sensor system configured for sensing biomechanical movement of a foot of a user during an athletic activity session, the sensor system includes an electronic module configured for wireless transmission of data generated by the sensor system, and wherein the data is received from the electronic module. The method may further include analyzing the data to determine whether a deviation from a desired footstrike pattern corresponding to the second footwear type exists, and generating an indication to the user upon completion of the athletic activity session, wherein the indication comprises at least one of a number and degree of deviations during the athletic activity, a suggested stretching activity, and a suggested activity report for a subsequent athletic activity.

Additional aspects of the invention relate to a non-transitory computer-readable medium including computer-executable instructions configured to cause an electronic device to receive data from a sensor system configured for sensing biomechanical movement of a foot of a user, the sensor system including an electronic module configured for wireless transmission of data generated by the sensor system, and wherein the data is received from the electronic module. The non-transitory computer-readable medium may further include instructions that, when executed, cause the electronic device to detect a footstrike pattern based on analysis of the data, compare the footstrike pattern to a desired footstrike pattern corresponding to a footwear type to determine whether a deviation from the desired footstrike pattern exists, and generate an indication to the user when the deviation from the desired footstrike pattern is determined to exist In some examples, the indication may include a degree of deviation from the desired footstrike pattern.

Further aspects of the invention relate to a system for transitioning from a first footwear type to a second footwear type including a sensor system configured to sense a biomechanical movement of a foot of a user and an electronic module configured for wireless transmission of data generated by the sensor system. The system may also include an electronic device in communication with the electronic module. The electronic device is configured for selecting a footwear transition program, each footwear transition program comprising a plurality of desired footstrike patterns corresponding to a preferred footstrike for the second footwear type, receiving data from the electronic module, comparing the data to a footstrike template to determine whether a deviation from the footstrike template exists, wherein the deviation is determined to exist if a degree of deviation from the footstrike template is determined to exceed a predetermined threshold, and generating an indication to the user when a deviation from the desired footstrike pattern is determined to exist. The footstrike template may include a midfoot-strike template or a forefoot-strike template, and the plurality of desired footstrike patterns may transition from a heel-strike pattern to a midfoot-strike pattern or a forefoot-strike pattern. Additionally, the indication may include an indication of the degree of deviation and the indication may include at least one of a visual indication, an audible indication, and a tactile indication. The footstrike templates may vary based on collected user information, and/or may vary after a predetermined amount of usage. The electronic device may further be configured for recording the data and providing a summary of recorded data to the user and/or generating an alert to the user when a number of recorded deviations exceeds a predetermined deviation count threshold. Any of the various aspects described above may be used in connection with this system, and it is understood that the system may be modified for use with different sensor systems and different articles of apparel.

Still further aspects of the invention relate to a system for analyzing athletic activity that may be used in connection with an article of apparel including a sensor system with a plurality of sensors engaged with the article of apparel and configured to sense a biomechanical parameter of a user while the user is in biomechanical movement. The system may further include a GPS module configured for detecting the user's position, and an electronic device in communication with the sensor system, where the GPS module is in communication with the electronic device. The electronic device is configured for receiving data generated by the sensor system, comparing the data to a biomechanical movement template corresponding to the desired biomechanical movement pattern to determine whether a deviation from the biomechanical movement template exists, and generating an indication to the user when the deviation from the desired biomechanical movement pattern is determined to exist. The electronic device is also configured for receiving the user's position from the GPS module and receiving terrain information related to the user's position and altering the biomechanical movement template based on the terrain information.

Other aspects of the invention relate to a method that involves performing some or all of the functions of the system as described above, including functions performed by the electronic device, the electronic module, or other apparatuses described above. Such a method may be computer-assisted. Aspects of the invention may similarly relate to a tangible and/or non-transitory computer-readable medium containing computer-executable instructions configured to cause an electronic device (or a processor of such a device) to perform some or all of the functions of the system as described above.

Still other features and advantages of the invention will be apparent from the following specification taken in conjunction with the following drawings.

BRIEF DESCRIPTION OF THE DRAWINGS

To allow for a more full understanding of the present invention, it will now be described by way of example, with reference to the accompanying drawings in which:

FIG. 14B is a cross-section view of the port and housing of FIG. 14A;

FIG. 23A is a magnified cross-sectional view of a sensor of the sensor system of FIG. 22, taken along lines 23-23 of FIG. 22;

FIG. 23B is a magnified cross-sectional view of a sensor of another embodiment of a sensor system connected to a sockliner for an article of footwear;

DETAILED DESCRIPTION

Figure 1:
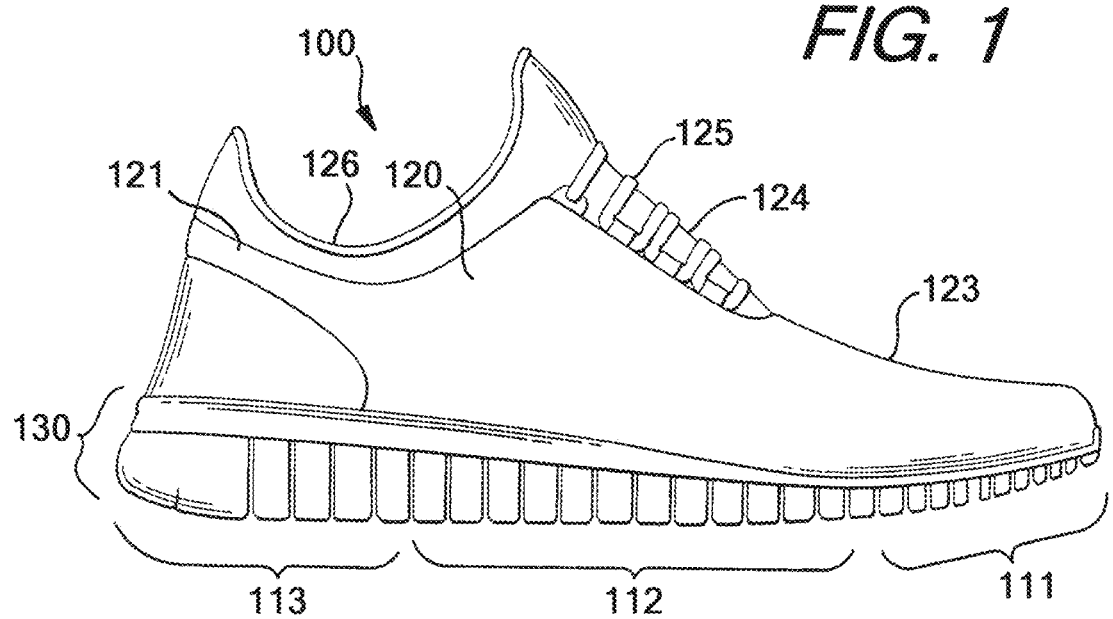
FIG. 1 is a side view of a shoe.

While this invention is susceptible of embodiment in many different forms, there are shown in the drawings, and will herein be described in detail, preferred embodiments of the invention with the understanding that the present disclosure is to be considered as an exemplification of the principles of the invention and is not intended to limit the broad aspects of the invention to the embodiments illustrated and described.

In general, a system and method are provided for analyzing athletic activity and biomechanical movement in such athletic activity, which may be used in connection with a sensor system for sensing at least one biomechanical parameter. The system and method can also provide coaching feedback to a user based on such analysis. The feedback provided to the user can include an indication that the user's biomechanical movement is deviating from a desired biomechanical movement pattern, and the system and method may utilize biomechanical movement templates for comparison with biomechanical parameters sensed by the sensor system in order to determine such deviation. A variety of embodiments and features of such a system and method are described below.

In one embodiment, the system may be used to provide coaching and/or other feedback to a user to assist the user in developing a specific footstrike pattern while running, walking, or otherwise moving by foot. Such a system may be used in connection with an article of footwear, such as a shoe, which is shown as an example in FIGS. 1-2 and generally designated with the reference numeral 100. The footwear 100 can take many different forms, including, for example, various types of athletic footwear. In one exemplary embodiment, the shoe 100 generally includes a force and/or pressure sensor system 12 operably connected to a universal communication port 14. As described in greater detail below, the sensor system 12 collects performance data relating to a wearer of the shoe 100. Through connection to the universal communication port 14, multiple different users can access the performance data for a variety of different uses as described in greater detail below.

Figure 2:
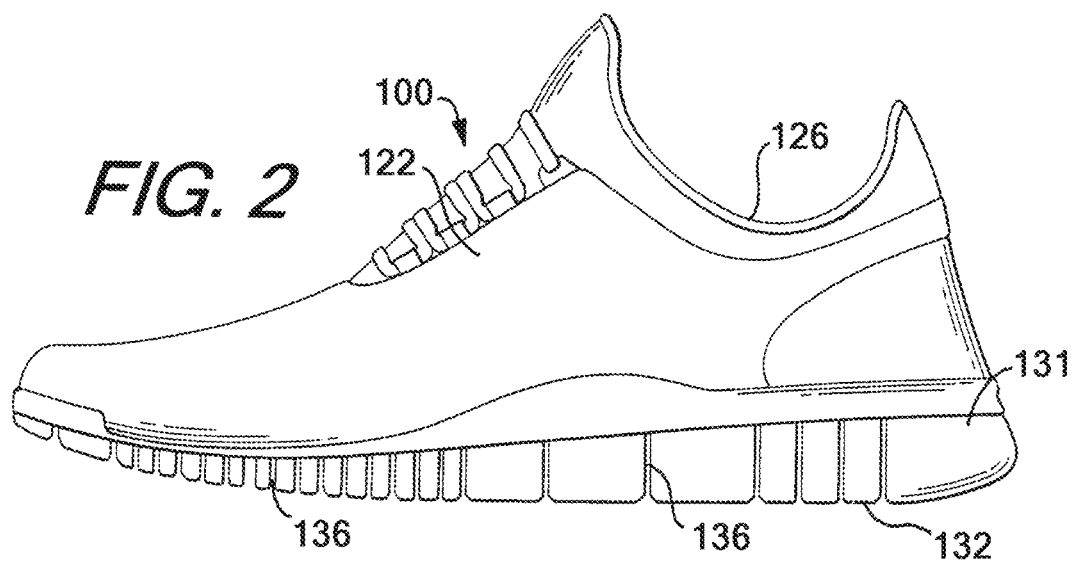
FIG. 2 is an opposed side view of the shoe of FIG. 1.

An article of footwear 100 is depicted in FIGS. 1-2 as including an upper 120 and a sole structure 130. For purposes of reference in the following description, footwear 100 may be divided into three general regions: a forefoot region 111, a midfoot region 112, and a heel region 113, as illustrated in FIG. 1. Regions 111-113 are not intended to demarcate precise areas of footwear 100. Rather, regions 111-113 are intended to represent general areas of footwear 100 that provide a frame of reference during the following discussion. Although regions 111-113 apply generally to footwear 100, references to regions 111-113 also may apply specifically to upper 120, sole structure 130, or individual components included within and/or formed as part of either upper 120 or sole structure 130.

As further shown in FIGS. 1 and 2, the upper 120 is secured to sole structure 130 and defines a void or chamber for receiving a foot. For purposes of reference, upper 120 includes a lateral side 121, an opposite medial side 122, and a vamp or instep area 123. Lateral side 121 is positioned to extend along a lateral side of the foot (i.e., the outside) and generally passes through each of regions 111-113. Similarly, medial side 122 is positioned to extend along an opposite medial side of the foot (i.e., the inside) and generally passes through each of regions 111-113. Vamp area 123 is positioned between lateral side 121 and medial side 122 to correspond with an upper surface or instep area of the foot. Vamp area 123, in this illustrated example, includes a throat 124 having a lace 125 or other desired closure mechanism that is utilized in a conventional manner to modify the dimensions of upper 120 relative the foot, thereby adjusting the fit of footwear 100. Upper 120 also includes an ankle opening 126 that provides the foot with access to the void within upper 120. A variety of materials may be used for constructing upper 120, including materials that are conventionally utilized in footwear uppers. Accordingly, upper 120 may be formed from one or more portions of leather, synthetic leather, natural or synthetic textiles, polymer sheets, polymer foams, mesh textiles, felts, non-woven polymers, or rubber materials, for example. The upper 120 may be formed from one or more of these materials wherein the materials or portions thereof are stitched or adhesively bonded together, e.g., in manners that are conventionally known and used in the art.

Upper 120 may also include a heel element (not shown) and a toe element (not shown). The heel element, when present, may extend upward and along the interior surface of upper 120 in the heel region 113 to enhance the comfort of footwear 100. The toe element, when present, may be located in forefoot region 111 and on an exterior surface of upper 120 to provide wear-resistance, protect the wearer's toes, and assist with positioning of the foot. In some embodiments, one or both of the heel element and the toe element may be absent, or the heel element may be positioned on an exterior surface of the upper 120, for example. Although the configuration of upper 120 discussed above is suitable for footwear 100, upper 120 may exhibit the configuration of any desired conventional or non-conventional upper structure without departing from this invention.

Figure 3:
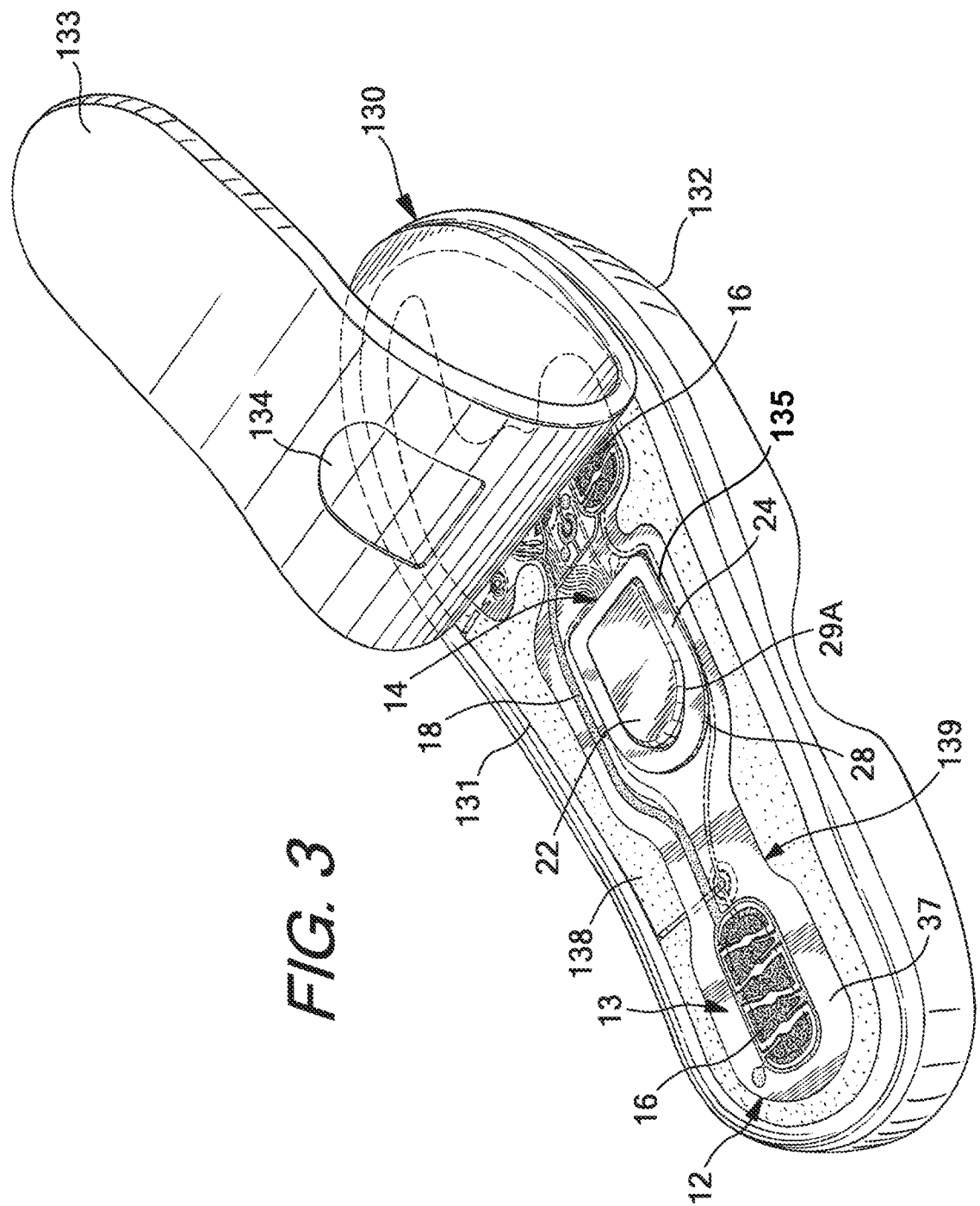
FIG. 3 is a top perspective view of a sole of a shoe (having a shoe upper removed and a foot contacting member folded aside) incorporating one embodiment of a sensor system that is configured for use in connection with aspects of the present invention.

As shown in FIG. 3, the sole structure 130 is secured to a lower surface of upper 120 and may have a generally conventional shape. The sole structure 130 may have a multipiece structure, e.g., one that includes a midsole 131, an outsole 132, and a foot contacting member 133. The foot contacting member 133 is typically a thin, compressible member that may be located within the void in upper 120 and adjacent to a lower surface of the foot (or between the upper 120 and midsole 131) to enhance the comfort of footwear 100. In various embodiments, the foot contacting member 133 may be a sockliner, a strobel, an insole member, a bootie element, a sock, etc. In the embodiment shown in FIGS. 3-4, the foot contacting member 133 is an insole member or a sockliner. The term "foot contacting member," as used herein does not necessarily imply direct contact with the user's foot, as another element may interfere with direct contact. Rather, the foot contacting member forms a portion of the inner surface of the foot-receiving chamber of an article of footwear. For example, the user may be wearing a sock that interferes with direct contact. As another example, the sensor system 12 may be incorporated into an article of footwear that is designed to slip over a shoe or other article of footwear, such as an external bootie element or shoe cover. In such an article, the upper portion of the sole structure may be considered a foot contacting member, even though it does not directly contact the foot of the user. In some arrangements, an insole or sockliner may be absent, and in other embodiments, the footwear 100 may have a foot contacting member positioned on top of an insole or sockliner.

Midsole member 131 may be or include an impact attenuating member, and may include multiple members or elements in some embodiments. For example, the midsole member 131 may be formed of polymer foam material, such as polyurethane, ethylvinylacetate, or other materials (such as phylon, phylite, etc.) that compress to attenuate ground or other contact surface reaction forces during walking, running, jumping, or other activities. In some example structures according to this invention, the polymer foam material may encapsulate or include various elements, such as a fluid-filled bladder or moderator, that enhance the comfort, motion-control, stability, and/or ground or other contact surface reaction force attenuation properties of footwear 100. In still other example structures, the midsole 131 may include additional elements that compress to attenuate ground or other contact surface reaction forces. For instance, the midsole 131 may include column type elements to aid in cushioning and absorption of forces.

Outsole 132 is secured to a lower surface of midsole 131 in this illustrated example footwear structure 100 and is formed of a wear-resistant material, such as rubber or a flexible synthetic material, such as polyurethane, that contacts the ground or other surface during ambulatory or other activities. The material forming outsole 132 may be manufactured of suitable materials and/or textured to impart enhanced traction and slip resistance. The outsole 132 shown in FIGS. 1 and 2 is shown to include a plurality of incisions or sipes 136 in either or both sides of the outsole 132, although many other types of outsoles 132 with various types of treads, contours, and other structures may be used in connection with the present invention. It is understood that embodiments of the present invention may be used in connection with other types and configurations of shoes, as well as other types of footwear and sole structures.

FIGS. 1-4 illustrate exemplary embodiments of the footwear 100 incorporating a sensor system 12 in accordance with the present invention, and FIGS. 3-8 illustrate exemplary embodiments of the sensor system 12. The sensor system 12 may include any of the features or embodiments of the sensor system described in U.S. patent application Ser. No. 13/401,918, which application is incorporated by reference herein in its entirety and made part hereof. The sensor system 12 includes an insert member 37 having a force and/or pressure sensor assembly 13 connected thereto. It is understood that the use of the insert member 37 is one embodiment, and that an article of footwear including a different type of sensor system 12 may be utilized in connection with the athletic analysis system 400 and method 500 described herein. It is also understood that insert 37 may have any number of different configurations, shapes, and structures, and including a different number and/or configuration of sensors 16, and a different insert structure or peripheral shape.

The insert member 37 is configured to be positioned in contact with the sole structure 130 of the footwear 100, and in one embodiment, the insert member 37 is configured to be positioned underneath the foot contacting member 133 and over the top of the midsole member 131 and in general confronting relation. The sensor assembly 13 includes a plurality of sensors 16, and a communication or output port 14 in communication with the sensor assembly 13 (e.g., electrically connected via conductors). The port 14 is configured for communicating data received from the sensors 16, such as to an electronic module (also referred to as an electronic control unit) 22 as described below. The port 14 and/or the module 22 may be configured to communicate with an external device, as also described below. In the embodiment illustrated in FIGS. 3-8, the system 12 has four sensors 16: a first sensor 16a at the big toe (first phalange or hallux) area of the shoe, two sensors 16b-c at the forefoot area of the shoe, including a second sensor 16b at the first metatarsal head region and a third sensor 16c at the fifth metatarsal head region, and a fourth sensor 16d at the heel. These areas of the foot typically experience the greatest degree of pressure during movement. Each sensor 16 is configured for detecting a pressure exerted by a user's foot on the sensor 16. The sensors communicate with the port 14 through sensor leads 18, which may be wire leads and/or another electrical conductor or suitable communication medium. For example, in the embodiment of FIGS. 3-8, the sensor leads 18 may be an electrically conductive medium that is printed on the insert member 37, such as a silver-based ink or other metallic ink, such as an ink based on copper and/or tin. The leads 18 may alternately be provided as thin wires in one embodiment. In other embodiments, the leads 18 may be connected to the foot contacting member 133, the midsole member 131, or another member of the sole structure 130.

Other embodiments of the sensor system 12 may contain a different number or configuration of sensors 16, and generally include at least one sensor 16. For example, in one embodiment, the system 12 includes a much larger number of sensors, and in another embodiment, the system 12 includes two sensors, one in the heel and one in the forefoot of the shoe 100. As another example, the system 12 may include one or more sensors in other locations on the shoe 100, such as connected to the upper in one embodiment (not shown), such as to measure cutting/shear force, kick force, etc. In addition, the sensors 16 may communicate with the port 14 in a different manner, including any known type of wired or wireless communication, including Bluetooth and near-field communication. A pair of shoes may be provided with sensor systems 12 in each shoe of the pair, and it is understood that the paired sensor systems may operate synergistically or may operate independently of each other, and that the sensor systems in each shoe may or may not communicate with each other. The communication of the sensor systems 12 is described in greater detail below. It is understood that the sensor system 12 may be provided with computer programs/algorithms to control collection and storage of data (e.g., pressure data from interaction of a user's foot with the ground or other contact surface), and that these programs/algorithms may be stored in and/or executed by the sensors 16, the module 22, and/or the external device 110.

Figure 4:
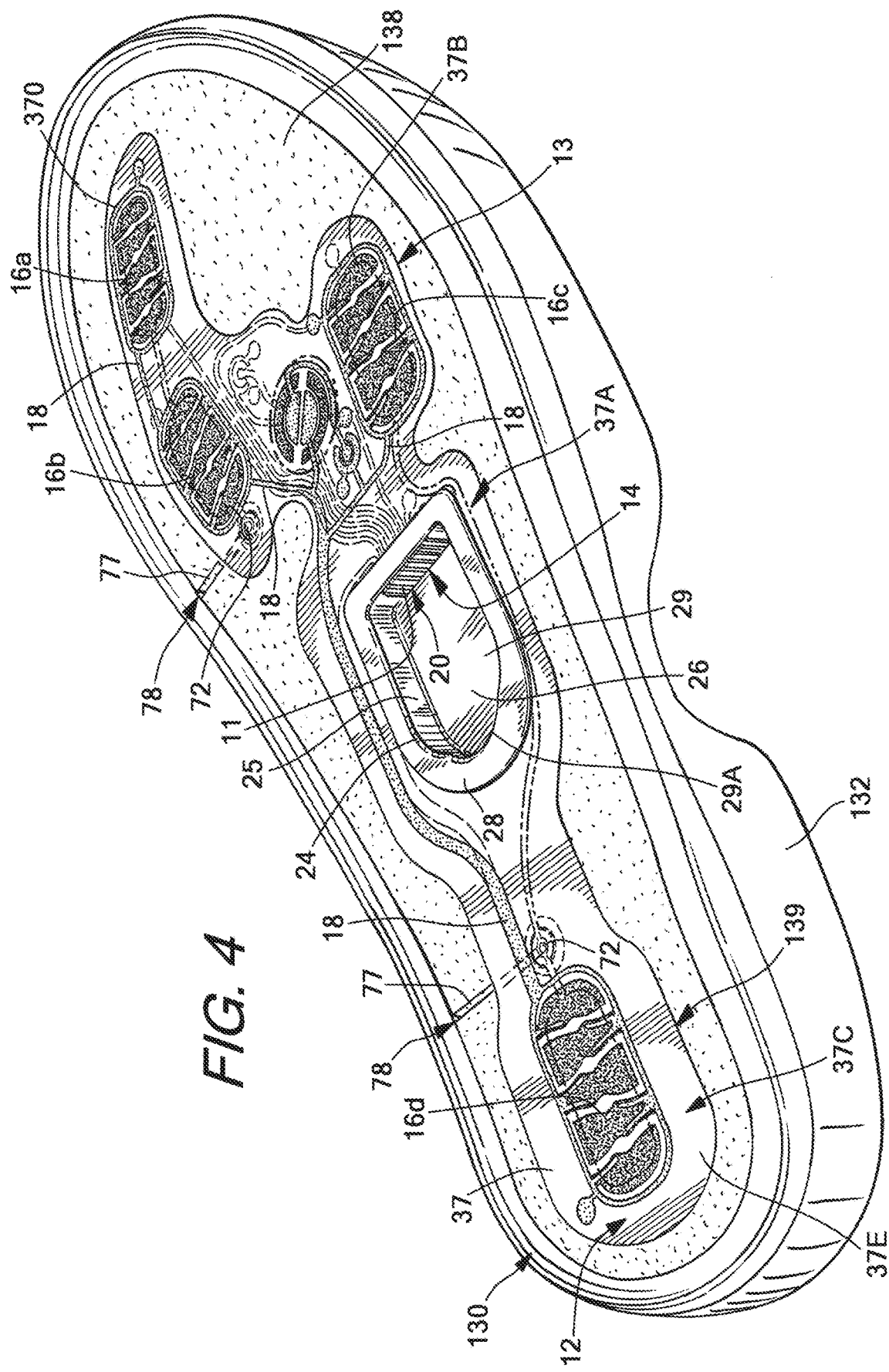
FIG. 4 is a top perspective view of the sole and the sensor system of FIG. 3, with a foot contacting member of the shoe removed and an electronic module removed.

The sensor system 12 can be positioned in several configurations in the sole 130 of the shoe 100. In the examples shown in FIGS. 3-4, the port 14, the sensors 16, and the leads 18 can be positioned between the midsole 131 and the foot contacting member 133, such as by positioning the insert member 37 between the midsole 131 and the foot contacting member 133. The insert member 37 may be connected to one or both of the midsole and the foot contacting member 133 in one embodiment. A cavity or well 135 can be located in the midsole 131 and/or in the foot contacting member 133 for receiving the electronic module 22, as described below, and the port 14 may be accessible from within the well 135 in one embodiment. The well 135 may further contain a housing 24 for the module 22, and the housing 24 may be configured for connection to the port 14, such as by providing physical space for the port 14 and/or by providing hardware for interconnection between the port 14 and the module 22. In the embodiment shown in FIGS. 3-4, the well 135 is formed by a cavity in the upper major surface of the midsole 131. As shown in FIGS. 3-4, the sole structure 130 may include a compressible sole member 138 that has a hole formed therein to receive the housing 24, which provides access to the well 135 and/or may be considered a portion of the well 135. The insert 37 can be placed on top of the compressible sole member 138 to place the housing 24 in the well 135. The compressible sole member 138 may confront the midsole 131 in one embodiment, and may be in direct contact with the midsole 131. It is understood that the compressible sole member 138 may confront the midsole 131 with one or more additional structures positioned between the compressible sole member 138 and the midsole 131, such as a strobel member. In the embodiment of FIGS. 3-4, the compressible sole member 138 is in the form of a foam member 138 (e.g. an EVA member) located between the foot contacting member 133 and the midsole 131, which may be considered a lower insole/sockliner in this embodiment. The foam member 138 may be bonded to a strobel (not shown) of the midsole 131 in one embodiment, such as by use of an adhesive, and may cover any stitching on the strobel, which can prevent abrasion of the insert 37 by the stitching.

In the embodiment shown in FIGS. 3-4, the housing 24 has a plurality of walls, including side walls 25 and a base wall 26, and also includes a flange or lip 28 that extends outward from the tops of the side walls 25 and is configured for connection to the insert 37. In one embodiment, the flange 28 is a separate member that connects to a tub 29 to form the housing 24, via pegs (not shown) that connect through holes 28B (FIG. 6) in the insert 37 located at the front end of the hole 27. The pegs may be connected via ultrasonic welding or other technique, and may be received in receivers in one embodiment. In an alternate embodiment, an article of footwear 100 may be manufactured with the tub 29 formed in the sole structure 130, and the flange 28 may be later connected, such as by a snap connection, optionally after other portions of the port have also been assembled. The housing 24 may include retaining structure to retain the module 22 within the housing 24, and such retaining structure may be complementary with retaining structure on the module 22, such as a tab/flange and slot arrangement, complementary tabs, locking members, friction-fit members, etc. The housing 24 also includes a finger recess 29A located in the flange 28 and/or the tub 29, which provides room for the user's finger to engage the module 22 to remove the module 22 from the housing 24. The flange 28 provides a wide base engaging the top of the insert 37, which spreads out the forces exerted on the insert 37 and/or on the foot contacting member 133 by the flange 28, which creates less likelihood of severe deflection and/or damage of such components. The rounded corners on the flange 28 also assists in avoiding damage to the insert 37 and/or the foot contacting member 133. It is understood that the flange 28 may have a different shape and/or contour in other embodiments, and may provide similar functionality with different shapes and/or contours.

The foot contacting member 133 is configured to be placed on top of the foam member 138 to cover the insert 37, and may contain an indent 134 in its lower major surface to provide space for the housing 24, as shown in FIG. 3. The foot contacting member 133 may be adhered to the foam member 138, and in one embodiment, may be adhered only in the forefoot region to permit the foot contacting member 133 to be pulled up to access the module 22, as shown in FIG. 3. Additionally, the foot contacting member 133 may include a tacky or high-friction material (not shown) located on at least a portion of the underside to resist slippage against the insert 37 and/or the foam member 138, such as a silicone material. For example, in an embodiment where the foot contacting member 133 is adhered in the forefoot region and free in the heel region (e.g. FIG. 3), the foot contacting member 133 may have the tacky material located on the heel region. The tacky material may also provide enhanced sealing to resist penetration of dirt into the sensor system. In another embodiment, the foot contacting member 133 may include a door or hatch (not shown) configured to be located over the port 14 and sized to permit insertion and/or removal of the module 22 through the foot contacting member 133, which door or hatch may be opened in various manners, such as swinging on a hinge or removal of a plug-like element. In one embodiment, the foot contacting member 133 may also have graphic indicia (not shown) thereon, as described below.

In one embodiment, as shown in FIGS. 3-4, the foam member 138 may also include a recess 139 having the same peripheral shape as the insert 37 to receive the insert 37 therein, and the bottom layer 69 (FIG. 8) of the insert member 37 may include adhesive backing to retain the insert 37 within the recess 139. In one embodiment, a relatively strong adhesive, such as a quick bonding acrylic adhesive, may be utilized for this purpose. The insert 37 has a hole or space 27 for receiving and providing room for the housing 24, and the foam member 138 in this embodiment may also allow the housing 24 to pass completely through into and/or through at least a portion of the strobel and/or the midsole 131. In the embodiment shown in FIGS. 3-4, the foot contacting member 133 may have a thickness that is reduced relative to a typical foot contacting member 133 (e.g. sockliner), with the thickness of the foam member 138 being substantially equal to the reduction in thickness of the foot contacting member 133, to provide equivalent cushioning. In one embodiment, the foot contacting member 133 may be a sockliner with a thickness of about 2-3 mm, and the foam member 138 may have a thickness of about 2 mm, with the recess 139 having a depth of about 1 mm. The foam member 138 may be adhesively connected to the insert member 37 prior to connecting the foam member 138 to the article of footwear 100 in one embodiment. This configuration permits the adhesive between the foam member 138 and the insert 37 to set in a flat condition before attaching the foam member to the strobel or other portion of the footwear 100, which is typically bends or curves the foam member 138 and may otherwise cause delamination. The foam member 138 with the insert 37 adhesively attached may be provided in this configuration as a single product for insertion into an article of footwear 100 in one embodiment. The positioning of the port 14 in FIGS. 3-4 not only presents minimal contact, irritation, or other interference with the user's foot, but also provides easy accessibility by simply lifting the foot contacting member 133.

In the embodiment of FIGS. 3-4, the housing 24 extends completely through the insert 37 and the foam member 138, and the well 135 may also extend completely through the strobel and partially into the midsole 131 of the footwear 100 to receive the housing 24. In another embodiment, the well 135 may be differently configured, and may be positioned completely underneath the strobel in one embodiment, with a window through the strobel to permit access to the module 22 in the well 135. The well 135 may be formed using a variety of techniques, including cutting or removing material from the strobel and/or the midsole 131, forming the strobel and/or the midsole 131 with the well contained therein, or other techniques or combinations of such techniques. The housing 24 may fit closely with the walls of the well 135, which can be advantageous, as gaps between the housing 24 and the well 135 may be sources of material failure. The process of removing the piece 135 may be automated using appropriate computer control equipment.

The well 135 may be located elsewhere in the sole structure 130 in further embodiments. For example, the well 135 may be located in the upper major surface of the foot contacting member 133 and the insert 37 can be placed on top of the foot contacting member 133. As another example, the well 135 may be located in the lower major surface of the foot contacting member 133, with the insert 37 located between the foot contacting member 133 and the midsole 131. As a further example, the well 135 may be located in the outsole 132 and may be accessible from outside the shoe 100, such as through an opening in the side, bottom, or heel of the sole 130. In the configurations illustrated in FIGS. 3-4, the port 14 is easily accessible for connection or disconnection of an electronic module 22, as described below. In another embodiment, the foot contacting member 133 may have the insert 37 connected to the bottom surface, and the port 14 and the well 135 may be formed in the sole structure 130. The interface 20 is positioned on the side of the housing 24 as similarly shown with respect to other embodiments, although it is understood that the interface 20 could be positioned elsewhere, such as for engagement through the top of the module 22. The module 22 may be altered to accommodate such a change. Other configurations and arrangements of the housing 24, the insert 37, the module 22, and/or the interface may be utilized in further embodiments.

In other embodiments, the sensor system 12 can be positioned differently. For example, in one embodiment, the insert 37 can be positioned within the outsole 132, midsole 131, or foot contacting member 133. In one exemplary embodiment, insert 37 may be positioned within a foot contacting member 133 positioned above an insole member, such as a sock, sockliner, interior footwear bootie, or other similar article, or may be positioned between the foot contacting member 133 and the insole member. Still other configurations are possible. As discussed, it is understood that the sensor system 12 may be included in each shoe in a pair.

The insert member 37 in the embodiment illustrated in FIGS. 3-8 is formed of multiple layers, including at least a first layer 66 and a second layer 68. The first and second layers 66, 68 may be formed of a flexible film material, such as a Mylar® or other PET (polyethylene terephthalate) film, or another polymer film, such as polyamide. In one embodiment, the first and second layers 66, 68 may each be PET films having thicknesses of 0.05-0.2 mm, such as a thickness of 125 m. Additionally, in one embodiment, each of the first and second layers 66, 68 has a minimum bend radius of equal to or less than 2 mm. The insert 37 may further include a spacer layer 67 positioned between the first and second layers 66, 68 and/or a bottom layer 69 positioned on the bottom of the insert 37 below the second layer 68, which are included in the embodiment illustrated in FIGS. 3-8. The layers 66, 67, 68, 69 of the insert 37 are stacked on top of each other and in confronting relation to each other, and in one embodiment, the layers 66, 67, 68, 69 all have similar or identical peripheral shapes and are superimposed on one another (FIG. 9). In one embodiment, the spacer layer 67 and the bottom layer 69 may each have a thickness of 89-111 m, such as a thickness of 100 m. The entire thickness of the insert member 37 may be about 450 µm in one embodiment, or about 428-472 m in another embodiment, and about 278-622 µm in a further embodiment. The insert 37 may also include additional adhesive that is 100-225 µm thick, and may further include one or more selective reinforcement layers, such as additional PET layers, in other embodiments. Additionally, in one embodiment, the entire four-layer insert as described above has a minimum bend radius of equal to or less than 5 mm. It is understood that the orientations of the first and second layers 66, 68 may be reversed in another embodiment, such as by placing the second layer 68 as the top layer and the first layer 66 below the second layer 68. In the embodiment of FIGS. 3-8, the first and second layers 66, 68 have various circuitry and other components printed thereon, including the sensors 16, the leads 18, resistors 53, 54, a pathway 50, dielectric patches 80, and other components, which are described in greater detail below. The components are printed on the underside of the first layer 66 and on the upper side of the second layer 68 in the embodiment of FIGS. 3-8, however in other embodiments, at least some components may be printed on the opposite sides of the first and second layers 66, 68. It is understood that components located on the first layer 66 and/or the second layer 68 may be moved/transposed to the other layer 66, 68.

The layers 66, 67, 68, 69 can be connected together by an adhesive or other bonding material in one embodiment. The spacer layer 67 may contain adhesive on one or both surfaces in one embodiment to connect to the first and second layers 66, 68. The bottom layer 69 may likewise have adhesive on one or both surfaces, to connect to the second layer 68 as well as to the article of footwear 100. The first or second layers 66, 68 may additionally or alternately have adhesive surfaces for this purpose. A variety of other techniques can be used for connecting the layers 66, 67, 68, 69 in other embodiments, such as heat sealing, spot welding, or other known techniques.

In the embodiment illustrated in FIGS. 3-8, the sensors 16 are force and/or pressure sensors for measuring pressure and/or force on the sole 130. The sensors 16 have a resistance that decreases as pressure on the sensor 16 increases, such that measurement of the resistance through the port 14 can be performed to detect the pressure on the sensor 16. The sensors 16 in the embodiment illustrated in FIGS. 3-8 are elliptical or obround in shape, which enables a single sensor size to be utilized in several different shoe sizes. The sensors 16 in this embodiment each include two contacts 40, 42, including a first contact 40 positioned on the first layer 66 and a second contact 42 positioned on the second layer 68. It is understood that the figures illustrating the first layer 66 herein are top views, and that the electronic structures (including the contacts 40, the leads 18, etc.) are positioned on the bottom side of the first layer 66 and viewed through a transparent or translucent first layer 66 unless specifically noted otherwise. The contacts 40, 42 are positioned opposite each other and are in superimposed relation to each other, so that pressure on the insert member 37, such as by the user's foot, causes increased engagement between the contacts 40, 42. The resistance of the sensor 16 decreases as the engagement between the contacts 40, 42 increases, and the module 22 is configured to detect pressure based on changes in resistance of the sensors 16. In one embodiment, the contacts 40, 42 may be formed by conductive patches that are printed on the first and second layers 66, 68, such as in the embodiment of FIGS. 3-8, and the two contacts 40, 42 may be formed of the same or different materials. Additionally, in one embodiment, the leads 18 are formed of a material that has a higher conductivity and lower resistivity than the material(s) of the sensor contacts 40, 42. For example, the patches may be formed of carbon black or another conductive carbon material. Further, in one embodiment, the two contacts 40, 42 may be formed of the same material or two materials with similar hardnesses, which can reduce abrasion and wear due to differences in hardness of the materials in contact with each other. In this embodiment, the first contacts 40 are printed on the underside of the first layer 66, and the second contacts 42 are printed on the top side of the second layer 68, to permit engagement between the contacts 40, 42. The embodiment illustrated in FIGS. 3-8 includes the spacer layer 67, which has holes 43 positioned at each sensor 16 to permit engagement of the contacts 40, 42 through the spacer layer 67, while insulating other portions of the first and second layers 66, 68 from each other. In one embodiment, each hole 43 is aligned with one of the sensors 16 and permits at least partial engagement between the contacts 40, 42 of the respective sensor 16. In the embodiment illustrated in FIGS. 3-8, the holes 43 are smaller in area than the sensor contacts 40, 42, allowing the central portions of the contacts 40, 42 to engage each other, while insulating outer portions of the contacts 40, 42 and the distribution leads 18A from each other (See, e.g., FIG. 8). In another embodiment, the holes 43 may be sized to permit engagement between the contacts 40, 42 over their entire surfaces. It is understood that the size, dimensions, contours, and structure of the sensors 16 and the contacts 40, 42 may be altered in other embodiments while retaining similar functionality. It is also understood that sensors 16 having the same sizes may be utilized in different sizes of inserts 37 for different shoe sizes, in which case the dimensions of the sensors 16 relative to the overall dimensions of the insert 37 may be different for different insert 37 sizes. In other embodiments, the sensor system 12 may have sensors 16 that are differently configured than the sensors 16 of the embodiment of FIGS. 3-8. In a further example, the sensors 16 may utilize a different configuration that does not include carbon-based or similar contacts 40, 42 and/or may not function as a resistive sensor 16. Examples of such sensors include a capacitive pressure sensor or a strain gauge pressure sensor, among other examples.

Figure 8:
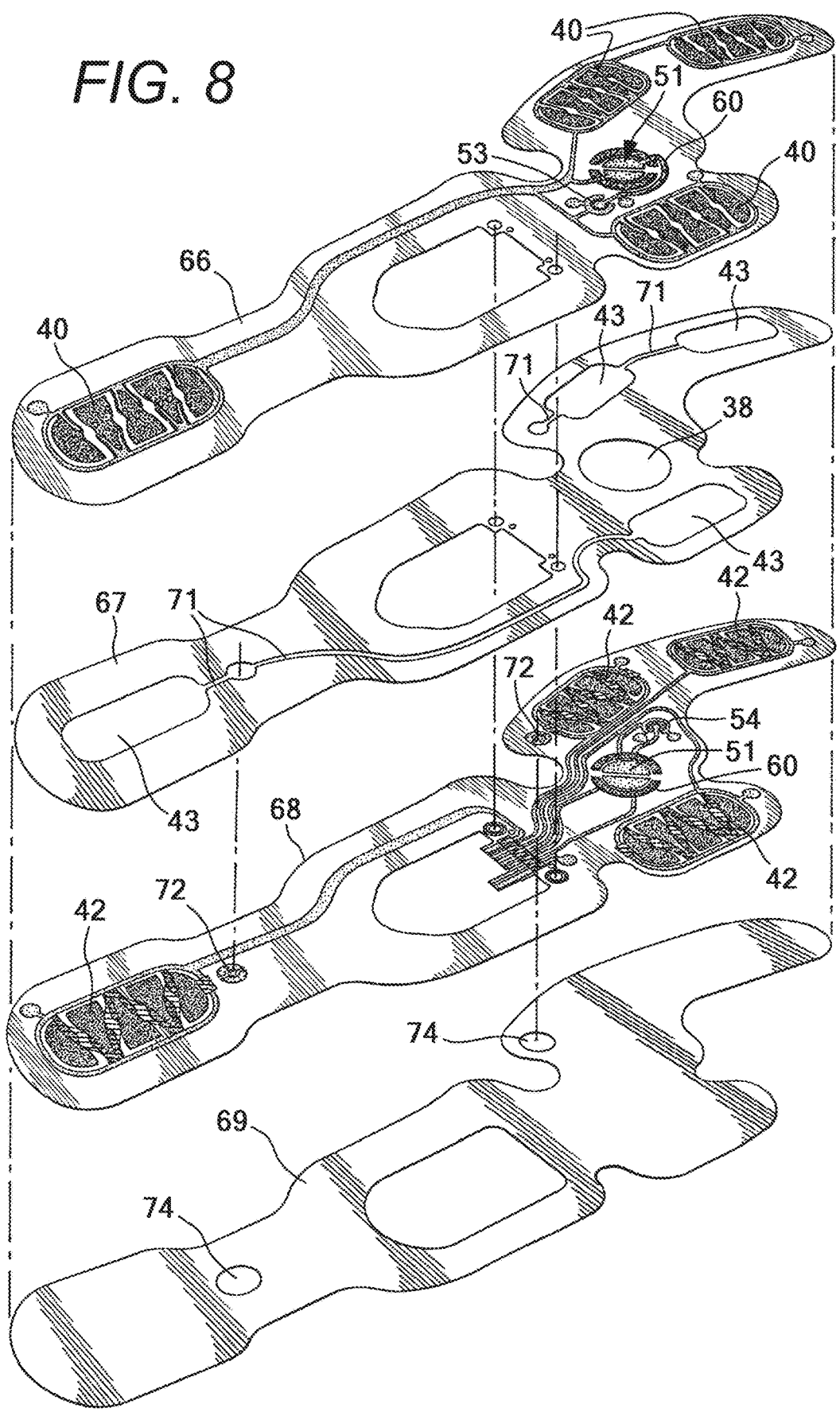
FIG. 8 is an exploded perspective view of the insert of FIG. 6, showing four different layers.
Figure 9:
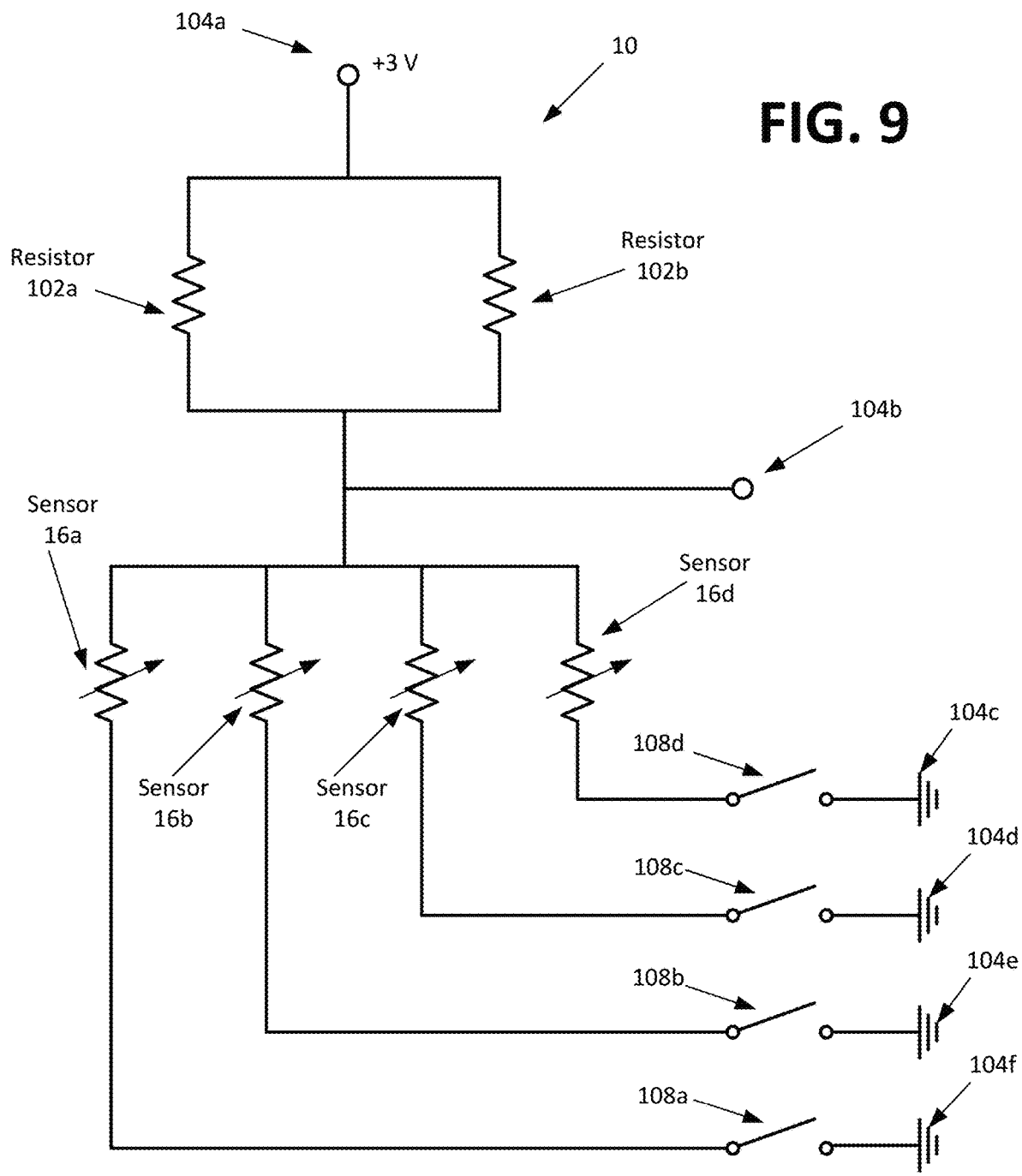
FIG. 9 is a schematic circuit diagram illustrating one embodiment of a circuit formed by the components of the sensor system of FIG. 3.

As further shown in FIGS. 3-8, in one embodiment, the insert 37 may include an internal airflow system 70 configured to allow airflow through the insert 37 during compression and/or flexing of the insert 37. FIG. 8 illustrates the components of the airflow system 70 in greater detail. The airflow system 70 may include one or more air passages or channels 71 that lead from the sensors 16 to one or more vents 72, to allow air to flow from the sensor 16 during compression, between the first and second layers 66, 68 and outward through the vent(s) 72 to the exterior of the insert 37. The airflow system 70 resists excessive pressure buildup during compression of the sensors 16, and also permits consistent separation of the contacts 40, 42 of the sensors 16 at various air pressures and altitudes, leading to more consistent performance. The channels 71 may be formed between the first and second layers 66, 68. As shown in FIG. 8, the spacer layer 67 has the channels 71 formed therein, and the air can flow through these channels 71 between the first and second layers 66, 68, to the appropriate vent(s) 72. The vents 72 may have filters (not shown) covering them in one embodiment. These filters may be configured to permit air, moisture, and debris to pass out of the vents 72 and resist moisture and debris passage into the vents 72. In another embodiment, the insert 37 may not contain a spacer layer, and the channels 71 may be formed by not sealing the layers 66, 68 together in a specific pattern, such as by application of a non-sealable material. Thus, the airflow system 70 may be considered to be integral with or directly defined by the layers 66, 68 in such an embodiment. In other embodiments, the airflow system 70 may contain a different number or configuration of air channels 71, vents 72, and/or other passages.

In the embodiment illustrated in FIGS. 3-8, the airflow system 70 includes two vents 72 and a plurality of air channels 71 connecting each of the four sensors 16 to one of the vents 72. The spacer layer 67 includes holes 43 at each sensor in this embodiment, and the channels 71 are connected to the holes 43 to permit air to flow away from the sensor 16 through the channel 71. Additionally, in this embodiment, two of the sensors 16 are connected to each of the vents 72 through channels 71. For example, as illustrated in FIGS. 4 and 8 the first metatarsal sensor 16*b* has a channel 71 that extends to a vent 72 slightly behind the first metatarsal area of the insert 37, and the first phalangeal sensor 16*a* has a channel 71 that also extends to the same vent 72, via a passageway that includes traveling through the first metatarsal sensor 16*b*. In other words, the first phalangeal sensor 16*a* has a channel 71 that extends from the hole 43 at the first phalangeal sensor 16*a* to the hole 43 at the first metatarsal sensor 16*b*, and another channel 71 extends from the first metatarsal sensor 16*b* to the vent 72. The fifth metatarsal sensor 16*c* and the heel sensor 16*d* also share a common vent 72, located in the heel portion of the insert 37. One channel 71 extends rearward from the hole 43 at the fifth metatarsal sensor 16*c* to the vent 72, and another channel 71 extends forward from the hole 43 at the heel sensor 16*d* to the vent 72. Sharing the vents 72 among multiple sensors can decrease expense, particularly by avoiding the need for additional filters 73. In other embodiments, the airflow system 70 may have a different configuration. For example, each sensor 16 may have its own individual vent 72, or more than two sensors 16 may share the same vent 72, in various embodiments.

Each vent 72 is formed as an opening in a bottom side of the second layer 68 (i.e. opposite the first layer 66), such that the opening permits outward flow of air, moisture, and/or debris from the airflow system 70, as seen in FIG. 9. In another embodiment, the vent 72 may include multiple openings. In a further embodiment, the vent 72 may additionally or alternately be formed by an opening in the first layer 66, causing the air to vent upwards out of the insert 37. In an additional embodiment, the vent 72 may be on the side (thin edge) of the insert 37, such as by extending the channel 71 to the edge, such that the channel 71 opens through the edge to the exterior of the insert 37. The venting of the air downward, as in the embodiment illustrated in FIGS. 3-8, makes it more difficult for debris to enter the vent 72. The bottom layer 69, if present, also includes apertures 74 located below the vents 72, to permit the air flowing out of the vents 72 to pass through the bottom layer 69. The apertures 74 are significantly larger than the vents 72, in order to allow filters to be adhesively attached to the second layer 68 through the bottom layer 69 around the periphery of each vent 72, as described below. Additionally, in this embodiment, each vent 72 has a reinforcement material 75 positioned around the vent 72, to add stability and strength to the material and prevent breaking/tearing. In the embodiment illustrated, the reinforcement material 75 is formed of the same material as the leads 18 (e.g. silver or other metallic ink) to facilitate printing, but may also be formed of the same material as the sensor contacts 40, 42 (e.g. carbon) or the dielectric material discussed herein.

The vents 72 in the embodiment illustrated in FIGS. 3-8 open downward and the air passing through the vents 72 passes downward toward the midsole 131 and toward the foam member 138 if present. In the embodiment illustrated in FIGS. 3-4, the foam member 138 has cavities 76 located directly below the vents 72 and configured such that the air exiting the vents passes into the respective cavity 76. Such cavities 76 may be formed as a slot that extends completely or partially through the foam member 138. This configuration allows air to pass out of the vents 72 without obstruction from the foam member 138. In the embodiment of FIGS. 3-4, each of the cavities 76 has a channel portion 77 extending laterally away from the cavity 76 and beyond the peripheral boundary of the insert 37. In other words, the channel portion 77 of the cavity 76 extends laterally from the vent 72 to a distal end 78 located outside the peripheral boundary of the insert 37. It is understood that if the foam member 138 has a recess 139 to receive the insert member 37, the distal end 78 of the channel portion 77 of the cavity 76 may also be located outside the peripheral boundary of the recess 139, as in the embodiment shown in FIGS. 3-4. This configuration permits air passing into the cavity 76 to exit the sole structure 130 by passing laterally through the channel portion 77 and then upward and/or outward away from the foam member 138. In another embodiment, the distal end 78 may stop at a point within the foam member 138 and still outside the peripheral boundary of the insert 37, which allows the air to vent upward out of the cavity 76 at the distal end 78 and provides the same or similar functionality. As stated above, the components of the airflow system 70 may be configured different in other embodiments.

Additionally, the foot contacting member 133 includes one or more passages 79 extending through the foot contacting member 133 located at the distal end 78 of the cavity 76, in the embodiment of FIGS. 3-8. The passages 79 may be pinhole-type passages 79 that extend vertically through the foot contacting member 133. In another embodiment, a different type of passage 79 may be used, including slits or grooves, and at least one passage 79 may extend laterally to a side of the foot contacting member 133, rather than upward through the thickness of the foot contacting member 133. The passages 79 allow the air exiting through the vent 72 and outward through the cavity 76 to pass through the foot contacting member 133 and out of the sole structure 130. In another embodiment, the foot contacting member 133 may not include any passage(s) 79. The foot contacting member 133 may still provide ventilation in a configuration without any passage(s) 79, such as by using a breathable foam or other breathable material for constructing the foot contacting member 133.

In the embodiment of FIGS. 3-8, as described above, the spacer layer 67 generally insulates conductive members/components on the first and second layers 66, 68 from each other, except in areas where electrical contact is desired, such as at the pathway 50 and between the contacts 40, 42 of the sensors 16. The spacer layer 67 has holes 38, 43 to define areas of desired electrical contact between the layers 66, 68. The components of the airflow system 70, in particular the channels 71 may provide a route for shorting or other undesired electrical contact by one or more conductive members between the first and second layers 66, 68. In one embodiment, the sensor system 12 may include one or more patches of dielectric material 80 to resist or prevent undesired shorting by one or more conductive members across open areas of the spacer layer 67, such as the channels 71. This dielectric material 80 may be in the form of an acrylic ink or other UV-curable ink, or another insulating material suitable for the application. In the embodiment shown in FIGS. 3-8, the insert 37 has several patches of dielectric material 80 extending across the channel 71, to insulate the distribution leads 18A located around the sensor contacts 40, 42 from each other.

In the embodiment of FIGS. 3-8, the port 14, the sensors 16, and the leads 18 form a circuit 10 on the insert member 37. The port 14 has a plurality of terminals 11, with four terminals 11 each dedicated to one of the four sensors 16 individually, one terminal 11 for applying a voltage to the circuit 10, and one terminal 1 for voltage measurement. In this embodiment, the sensor system 12 also includes a pair of resistors 53, 54, each located on one of the layers 66, 68, and a pathway 50 connecting the circuitry on the first layer 66 with the circuitry on the second layer 68. The resistors 53, 54 provide a reference point for the module 22 to measure the resistance of each sensor 16, and permit the module 22 to convert the variable current from the active sensor 16 into a measurable voltage. Additionally, the resistors 53, 54 are arranged in parallel within the circuit 10, which compensates for variations in the circuit 10 and/or variations in the manufacturing processes used to create the resistors 53, 54, such as variations in conductivity of the inks used to print the leads 18 and/or the sensor contacts 40, 42. In one embodiment, the equivalent resistance of the two resistors 53, 54 is 1500+/−500 kΩ. In another embodiment, a single resistor 53, 54 or two resistors 53, 54 in series could be used. In a further embodiment, the resistors 53, 54 may be positioned elsewhere on the insert 37, or may be located within the circuitry of the module 22. A more technical depiction of the circuit 10 of this embodiment is described below and shown in FIG. 9.

FIG. 9 illustrates a circuit 10 that may be used to detect and measure pressure in accordance with an embodiment of the invention. The circuit 10 includes six terminals 104a-104f, including a power terminal 104a for applying a voltage to the circuit 10, a measurement terminal 104b for measuring a voltage as described below, and four sensor terminals 104c-104f, each of which is dedicated to one of the sensors 16a-16d individually, and each of which represents ground in this embodiment. The terminals 104a-104f represent the terminals 11 of the port 14. In the embodiment shown, fixed resistors 102a and 102b, which represent resistors 53 and 54, are connected in parallel. Fixed resistors 102a and 102b may be physically located on separate layers. The equivalent resistance across terminals 104a and 104b is determined by the well-known equation of:

$$R_{eq} = R_{102a} \cdot R_{102b}/(R_{102a} + R_{102b}) \quad \text{(Equation 1)}$$

Where:
$R_{102a}$ = Resistance of fixed resistors 102a
$R_{102b}$ = Resistance of fixed resistors 102b
$R_{eq}$ = Equivalent resistance Electrically connecting fixed resistors 102a and 102b in parallel compensates for variations in the manufacturing processes used to create fixed resistors 102a and 102b. For example, if fixed resistor 102a has a resistance that deviates from a desired resistance, the deviation of the equivalent resistance determined by equation 1 is minimized by the averaging effect of fixed resistor 102b. One skilled in the art will appreciate that two fixed resistors are shown for illustration purposes only. Additional fixed resistors may be connected in parallel and each fixed resistor may be formed on a different layer.

In the embodiment shown in FIG. 9, fixed resistors 102a and 102b are connected to sensors 16a-16d. Sensors 16a-16d may be implemented with variable resistors that change resistance in response to changes in pressure, as described above. Each of sensors 16a-16d may be implemented with multiple variable resistors. In one embodiment, each of sensors 16a-16d is implemented with two variable resistors which are physically located on different layers and electrically connected in parallel. For example, as described above with respect to one embodiment, each sensor 16a-16d may contain two contacts 40, 42 that engage each other to a greater degree as applied pressure increases, and the resistance of the sensor 16a-16d may decrease as the engagement increases. As mentioned above, connecting resistors in parallel creates an equivalent resistance that minimizes deviations created during manufacturing processes. In another embodiment, the contacts 40, 42 may be arranged in series. Sensors 16a-16d may be connected to ground via switches 108a-108d. Switches 108a-108d may be closed one at a time to connect a sensor. In some embodiments, switches 108a-108d are implemented with transistors or integrated circuits.

In operation a voltage level, such as 3 volts, is applied at terminal 104a. Switches 108a-108d are closed one at a time to connect one of sensors 16a-16d to ground. When connected to ground, each of sensors 16a-16d forms a voltage divider with the combination of fixed resistors 102a and 102b. For example, when switch 108a is closed, the voltage between terminal 104a and ground is divided between the combination of fixed resistors 102a and 102b and sensor 16a. The voltage measured at terminal 104b changes as the resistance of sensor 16a changes. As a result, pressure applied to sensor 16a may be measured as a voltage level at terminal 104b. The resistance of the sensor 16a is measured utilizing the voltage applied to the sensor 16a in series with the combined fixed resistors 104a and 104b of known value. Similarly, selectively closing switches 108b-108d will generate voltage levels at terminal 104b that are related to the pressure applied at sensors 16b-16d. It is understood that the connections between the sensors 16a-d and the terminals 104c-f may be different in other embodiments. For example, the sensors 16a-d are connected to different pins of the interface 20 in the left shoe insert 37 as compared to the right shoe insert 37, as shown in FIG. 8. In another embodiment, the voltage level may be applied in the opposite manner, with the ground located at terminal 104a and the voltage applied at terminals 104c-f. In further embodiments, another circuit configuration may be used to achieve a similar result and functionality.

As can be seen in FIG. 8, the two resistors 53, 54 have similar or identical structures in the embodiment illustrated, however it is understood that the resistors may have different structures in other embodiments. Each resistor 53, 54 has two sections 55, 56 spaced from each other and a bridge 57 positioned between and connecting the sections 55, 56. In one embodiment, the bridge 57 may be formed of a more resistive material than the sections 55, 56, and may thus provide the majority of the resistance of each resistor 53, 54. The sections 55, 56 may be at least partially formed of a high-conductivity material, such as a silver material. In the embodiment illustrated—in FIGS. 3-9, the inner and outer sections 55, 56 are formed of the same material as the leads 18, such as a printed silver-based or other metallic-based ink. In this embodiment, the bridge 57 is formed of the same material as the sensor contacts 40, 42, such as carbon black or another conductive carbon material. It is understood that the inner and outer sections 55, 56 and/or the bridge 57 may be formed of different materials in other embodiments.

The pathway 50 generally permits continuous and/or uninterrupted electrical communication and passes electronic signals between the first and second layers 66, 68. In the embodiment of FIGS. 3-8, the port 14 is directly connected to the second layer 68, and the pathway 50 may serve as a vertical path between the port 14 and the sensor contacts 40 on the first layer 66, 68. In this embodiment, the pathway 50 includes conductive portions 51 on the first layer 66 and the second layer 68, such that conductive portions 51 may be in continuous engagement with each other to provide continuous electrical communication between the first and second layers 66, 68. The spacer layer 67 in this embodiment includes a hole 38 that is aligned with the pathway 50 and allows for continuous engagement between the conductive portions 51 through the spacer layer 67. Additionally, in the embodiment of FIGS. 3-5, each of the conductive portions 51 is divided into two sections 52 that are separated by an elongated gap 59. The gap 59 may be oriented to increase the durability of the pathway 50 during flexing of the insert 37, by serving as a flexing point to minimize bending of the conductive portions 51. The conductive portions 51 of the pathway 50 are formed of a conductive material, and in one embodiment, the conductive portions 51 may be formed of the same material as the leads 18, such as a silver-based ink or other metallic ink. In other embodiments, the pathway 50, and the components thereof described herein, may have a different size, shape, form, or location, and may be formed of a different material. Additionally, the pathway 50 may be at least partially surrounded by or bounded by a stiffening structure 60 in one embodiment to provide structural support and/or effects, such as assisting with engagement between the conductive portions 51. As illustrated in FIGS. 3-8, the conductive portions 51 are surrounded by a substantially annular stiffener 60. The stiffener 60 may be formed of any material that has suitable stiffness, and in one embodiment, may be formed of a material with greater stiffness than the material of the conductive portions 51, such as carbon black or other carbon-based material. Further, the hole 38 in the spacer layer 67 permits the conductive portions 51 to engage each other.

The insert 37 may be constructed by depositing the various components on a polymer (e.g. PET) film. In one embodiment, the insert 37 is constructed by first depositing the conductive metallic material on each layer 66, 68, such as by printing in the traced pattern of the leads 18 (including the distribution lead 18A, the conductive portions 51 of the pathway 50, the inner and outer sections 55, 56 of the resistors 53, 54, etc. The additional carbon material can then be deposited on each layer 66, 68, such as by printing, to form the contacts 40, 42, the stiffener 60 of the pathway 50, the bridge 57 of the resistors 53, 54, etc. Any additional components can then be deposited, such as any dielectric portions. The layers 66, 68 may be printed on PET sheets and then cut out to form the outer peripheral shape after printing in one embodiment.

The port 14 is configured for communication of data collected by the sensors 16 to an outside source, in one or more known manners. In one embodiment, the port 14 is a universal communication port, configured for communication of data in a universally readable format. In the embodiments shown in FIGS. 3-8 and 14, the port 14 includes an interface 20 for connection to an electronic module 22, shown in connection with the port 14 in FIG. 3. Additionally, in this embodiment, the port 14 is associated with the housing 24 for insertion of the electronic module 22, located in the well 135 in the middle arch or midfoot region of the midsole 131. As illustrated in FIGS. 3-8, the sensor leads 18 converge together to form a consolidated interface 20 at their terminals 11, in order to connect to the port 14. In one embodiment, the consolidated interface may include individual connection of the sensor leads 18 to the port interface 20, such as through a plurality of electrical contacts. In another embodiment, the sensor leads 18 could be consolidated to form an external interface, such as a plug-type interface or another configuration, and in a further embodiment, the sensor leads 18 may form a non-consolidated interface, with each lead 18 having its own separate terminal 11. As also described below, the module 22 may have an interface 23 for connection to the port interface 20 and/or the sensor leads 18.

In the embodiments shown in FIGS. 3-8 and 14, the interface 20 takes the form of electrical contacts or terminals 11. In one embodiment, the terminals 11 are formed on a tongue or extension 21 that extends from one of the layers 66, 68 into the hole 27 provided for the housing 24. The extension consolidates the ends of the leads 18 to a single area to form the interface 20. In the embodiment of FIGS. 3-8 and 14, the extension 21 extends from the second layer 68 into the hole 27, and is bent downward within the housing 24 to place the terminals 11 within the housing 24 and make the interface 20 accessible within the housing 24. The extension 21 may pass underneath the flange 28 of the housing 24 and through a slot or other space underneath the lip 28 in order to extend into the housing 24. In the configuration illustrated in FIGS. 3-8 and 14, the extension 21 bends downwardly into the well 135 and into the housing 24, as discussed above, to place the terminals 11 within the housing 24 and forming the interface 20 within the housing 24.

Figure 14A:
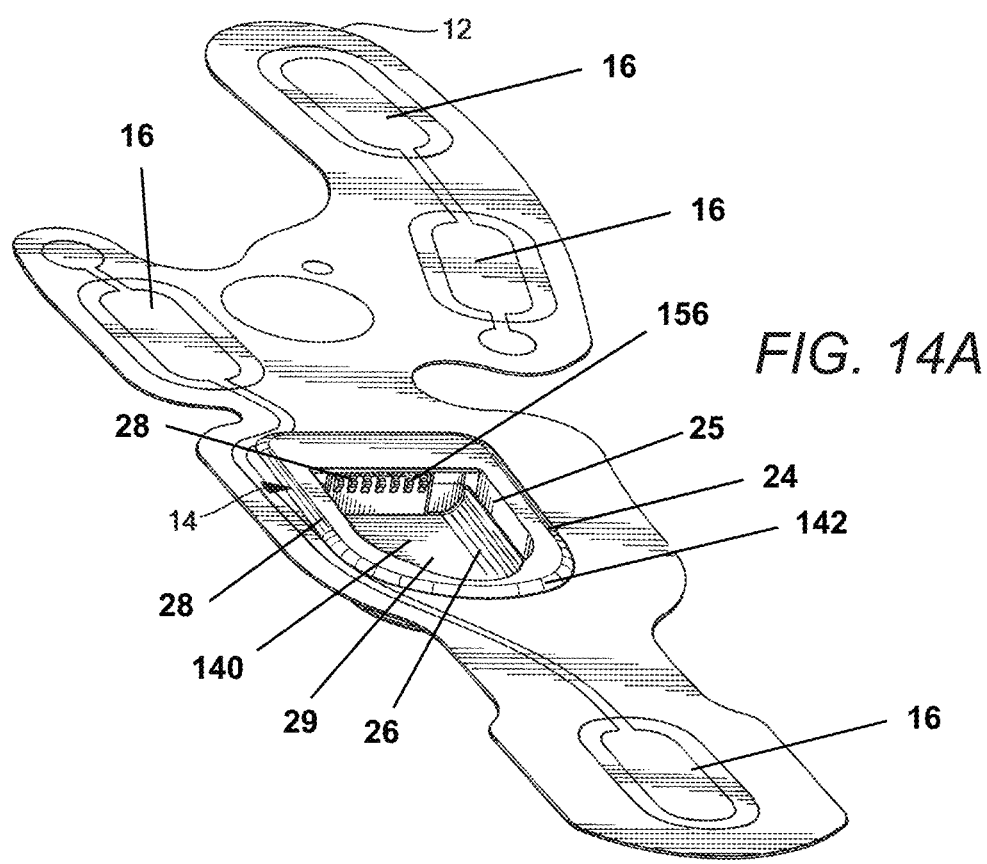
FIG. 14A is a perspective view of one embodiment of a port and a housing for connection to an electronic module, attached to an insert member.

The housing 24 may contain connection structure, such as connector pins or springs for establishing connection between the interface 20 and the module 22, as shown in FIGS. 14A-B. In one embodiment, the port 14 includes an electrical connector 82 forming the interface 20, which may include contacts that individually attach to the terminals 11, as mentioned above. The connector 82 may connect to the extension 21 and the terminals 11 via a crimping connection. The interface 20 in this embodiment includes seven terminals: four terminals 11 each individually connected to one of the sensors 16, one terminal 11 serving as the measurement terminal (104*b* in FIG. 9), and one terminal serving as a power terminal (104*a* in FIG. 9) to apply a voltage to the circuit 10. As discussed above, the power terminal may instead be configured as a ground terminal in another embodiment, with the sensor terminals (104*c-f* in FIG. 9) being configured as power terminals. The seventh terminal may be utilized for powering of accessories, such as a unique identification chip. In one embodiment, the sixth and seventh terminals 11 are extended on a tail 21A that extends from the end of the extension 21. An accessory may be connected across the two terminals 11 on the tail 21A to power the accessory. The accessory may include a small printed circuit board (PCB) with a memory chip that are attached via anisotropic contact formation to the tail 21A. In one embodiment, an accessory chip may include information uniquely identifying the article of footwear 100, such as a serial number, as well as substantive information such as whether the footwear 100 is a left or right shoe, a men's or women's shoe, a specific type of shoe (e.g. running, tennis, basketball, etc.), and other types of information. This information may be read by the module 22 and subsequently used in analysis, presentation, and/or organization of data from the sensors. The accessory may be sealed into the housing 24, such as via epoxy or other material.

The port 14 is adapted for connection to a variety of different electronic modules 22, which may be as simple as a memory component (e.g., a flash drive) or which may contain more complex features. It is understood that the module 22 could be as complex a component as a personal computer, mobile device, server, etc. The port 14 is configured for transmitting data gathered by the sensors 16 to the module 22 for storage, transmission, and/or processing. In some embodiments, the port 14, the sensors 16, and/or other components of the sensor system 12 may be configured for processing the data. The port 14, sensors 16, and/or other components of the sensor system 12 may additionally or alternately be configured for transmission of data directly to an external device 110 or a plurality of modules 22 and/or external devices 110. It is understood that the port 14, the sensors 16, and/or other components of the sensor system 12 may include appropriate hardware, software, etc., for these purposes. Examples of a housing and electronic modules in a footwear article are illustrated in U.S. patent application Ser. No. 11/416,458, published as U.S. Patent Application Publication No. 2007/0260421, which is incorporated by reference herein and made part hereof. Although the port 14 is illustrated with electronic terminals 11 forming an interface 20 for connection to a module 22, in other embodiments, the port 14 may contain one or more additional or alternate communication interfaces. For example, the port 14 may contain or comprise a USB port, a Firewire port, 16-pin port, or other type of physical contact-based connection, or may include a wireless or contactless communication interface, such as an interface for Wi-Fi, Bluetooth, near-field communication, RFID, Bluetooth Low Energy, Zigbee, or other wireless communication technique, or an interface for infrared or other optical communication technique. In another embodiment, the sensor system 12 may include more than one port 14 configured for communication with one or more modules 22 or external devices 110. This configuration may alternately be considered to be a single distributed port 14. For example, each of the sensors 16 may have a separate port 14 for communication with one or more electronic modules 22. The ports 14 in this embodiment are connected to the sensors 16 by leads 18 and may be located between the layers of the insert 37, within a hole in the insert 37, or above or below the insert 37 in various embodiments. It is understood that multiple or distributed port(s) 14 may be used, with combinations of two or more sensors connected to a single port 14. In further embodiments, the sensor system 12 may include one or more ports 14 having different configurations, which may include a combination of two or more configurations described herein.

Figure 20:
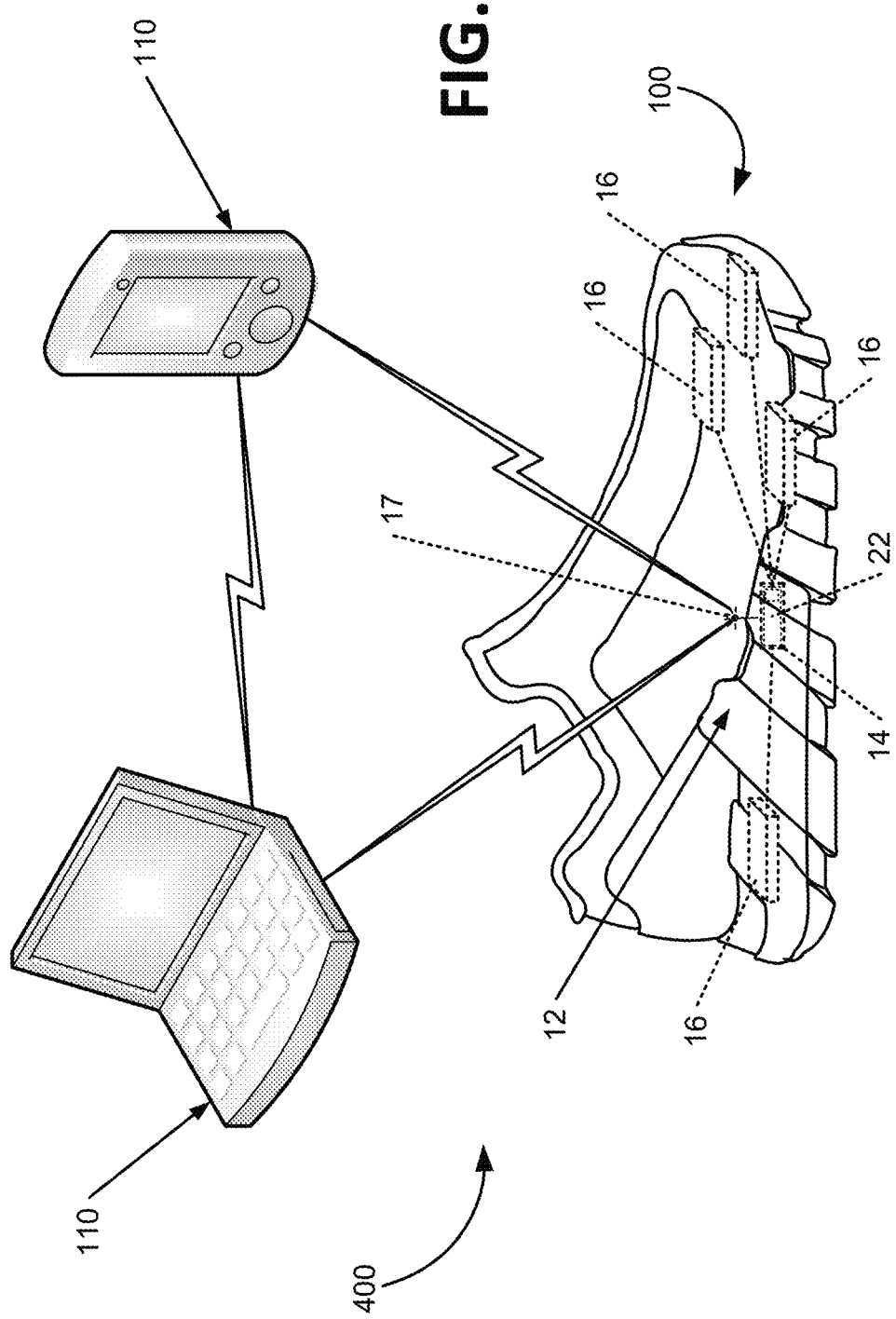
FIG. 20 is a schematic diagram of one embodiment of an article of footwear having a sensor system with an electronic module in communication with external electronic devices.

The module 22 may additionally have one or multiple communication interfaces for connecting to an external device 110 to transmit the data for processing, as described below and shown in FIGS. 5 and 20-21. Such interfaces can include any of the contacted or contactless interfaces described above. In one example, the module 22 includes at least a retractable USB connection for connection to a computer and/or for charging a battery of the module 22. In another example, the module 22 may be configured for contacted or contactless connection to a mobile device, such as a watch, cell phone, portable music player, etc. The module 22 may be configured for wireless communication with the external device 110, which allows the device 22 to remain in the footwear 100. However, in another embodiment, the module 22 may be configured to be removed from the footwear 100 to be directly connected to the external device 110 for data transfer, such as by the retractable USB connection described above. FIG. 20 illustrates one embodiment where the module 22 is configured for wireless communication with one or more external devices 110. Such external devices 110 may also communicate information received from the sensor system 12 with each other, as also shown in FIG. 20.

In a wireless embodiment, the module 22 may be connected to an antenna 17 for wireless communication (see FIG. 20). The antenna 17 may be shaped, sized, and positioned for use with the appropriate transmission frequency for the selected wireless communication method. Additionally, the antenna 17 may be located internally within the module 22 or external to the module. In one example, the sensor system 12 itself (such as the leads 18 and conductive portions of the sensors 16) could be used to form an antenna. The module 22 may further be placed, positioned, and/or configured in order to improve antenna reception, and in one embodiment, may use a portion of the user's body as an antenna. In one embodiment, the module 22 may be permanently mounted within the footwear 100, or alternately may be removable at the option of the user and capable of remaining in the footwear 100 if desired. Additionally, as further explained below, the module 22 may be removed and replaced with another module 22 programmed and/or configured for gathering and/or utilizing data from the sensors 16 in another manner. If the module 22 is permanently mounted within the footwear 100, the sensor system 12 may further contain an external port (not shown) to allow for data transfer and/or battery charging, such as a USB or Firewire port. It is understood that the module 22 may be configured for both contacted and contactless communication.

Figure 21:
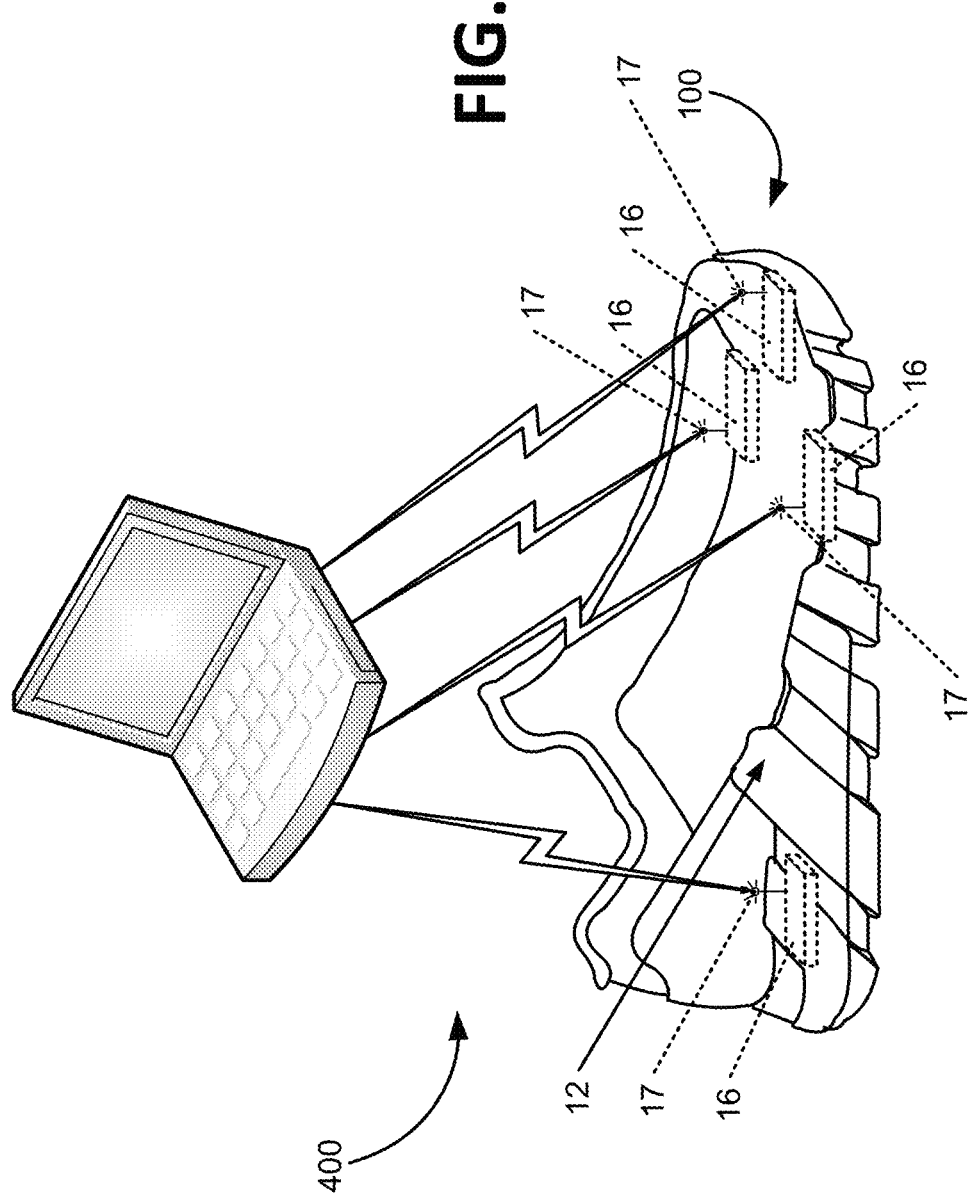
FIG. 21 is a schematic diagram of another embodiment of an article of footwear having a sensor system in communication with an external electronic device.

In another embodiment, illustrated in FIG. 21, the system 12 may include no module 22, and instead, the sensors 16 may be in direct wired or wireless communication with the external device 110. In the embodiment shown in FIG. 21, the sensors 16 each have a separate antenna 17 (and may also include a transmitter or TX/RX 107) that communicates with the external device 110. In another embodiment, multiple sensors 16 may communicate through a single antenna 17 (and/or single transmitter or TX/RX 107). It is understood that a single device 110 is shown in FIG. 21 for simplicity, and that the sensor system 12 may be in direct or indirect communication with several external devices 110.

While the port 14 may be located in a variety of positions without departing from the invention, in one embodiment, the port 14 is provided at a position and orientation and/or is otherwise structured so as to avoid or minimize contact with and/or irritation of the wearer's foot, e.g., as the wearer steps down in and/or otherwise uses the article of footwear 100, such as during an athletic activity. The positioning of the port 14 in FIGS. 3-4 and 14 illustrates one such example. In another embodiment, the port 14 is located proximate the heel or instep regions of the shoe 100. Other features of the footwear structure 100 may help reduce or avoid contact between the wearer's foot and the port 14 (or an element connected to the port 14) and improve the overall comfort of the footwear structure 100. For example, as described above and illustrated in FIGS. 3-4, the foot contacting member 133 may fit over and at least partially cover the port 14, thereby providing a layer of padding between the wearer's foot and the port 14. Additional features for reducing contact between the port 14 and the wearer's foot and modulating any undesired feel of the port 14 at the wearer's foot may be used.

FIGS. 14A-B show further views of one embodiment of the port 14 configured to be utilized with the insert member 37. Similar structures described above will be designated with identical or similar reference numerals. This embodiment and variations of the embodiment are described in detail below. As discussed and disclosed herein, the port 14 defines or supports an interface 20 for an operable connection with the module 22. The module 22 will also be described in greater detail below. Through the operable connection between the port 14 and the module 22, data sensed by the sensor assembly 12 can be acquired, stored and/or processed for further use and analysis.

As further shown in FIGS. 14A-B, the housing 24 in this embodiment includes a base member 140 and a cover member 142. The base member 140 may correspond to the tub 29 as described above that defines the side walls 25 and the base wall 26. The cover member 142 has a central aperture 153 dimensioned to receive the module 22 therethrough. An underside of the cover member 142 has a pair of depending posts (not shown) that cooperate with receivers (not shown) on the base member 140 as will be described. An outer periphery of the cover member 142 defines the lip or flange 28. In an exemplary embodiment, the cover member 142 may have depending walls that cooperatively define the side walls 25 of the housing 24. In such configuration, the base member 140 may define a ledge on the side wall to receive the depending walls on the cover member 142.

FIG. 14B further shows components of the interface assembly 156. The interface assembly 156 has a carrier 157 that supports the electrical connectors 82 such as described schematically in reference to FIG. 32. The electrical connectors 82 each have a distal end defining a contact that is resiliently supported by the carrier 157 that will cooperate with a corresponding contact on the module 22. As shown in FIG. 14, the interface assembly 156 is operably connected to the extension 21 having the leads 11 thereon of the insert member 37. As further shown in FIG. 14B, it is understood that the tail 21A can be further folded over to be positioned adjacent a back side of the extension 21. As further shown in FIG. 14, the carrier 157 is positioned in a first lateral slot 148 of the base member 140 of the housing 24. As can be appreciated from FIG. 14B, a filler material 159 (e.g. a potting compound) may be injected into a second lateral slot 150 behind the carrier 157. This configuration places the connectors 82 of the interface 20 exposed within the tub 29 for connection to the module 22.

Figure 15:
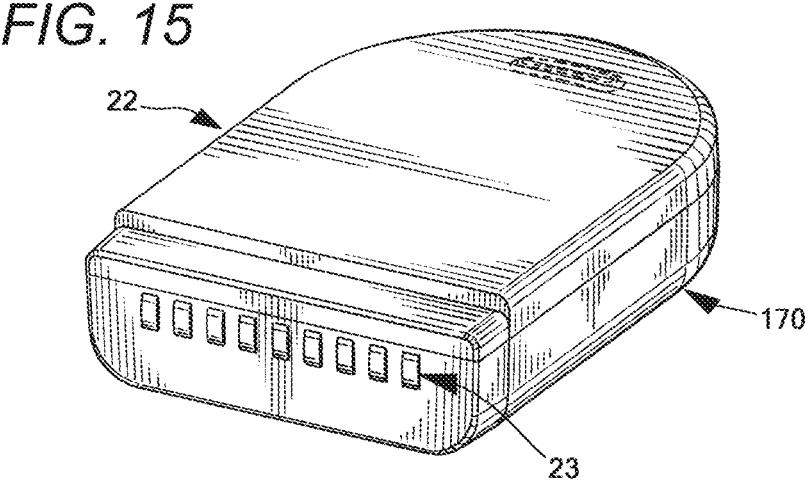
FIG. 15 is a perspective view of a module according to aspects of the present invention.
Figure 16:
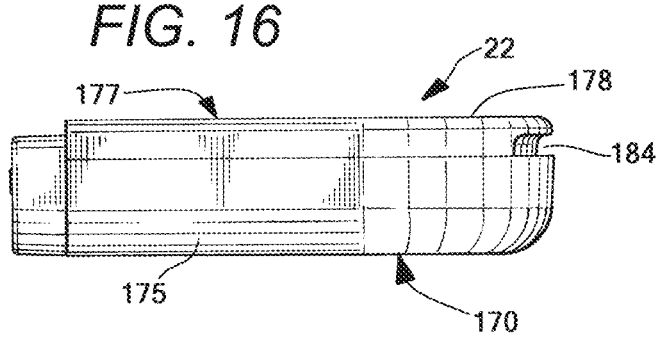
FIG. 16 is a side view of the module of FIG. 15.

FIGS. 15-16 disclose additional views and features of one embodiment of the module 22. As previously discussed, the module 22 is received by and is operably connected to the port 14 to collect, store and/or process data received from the sensor assembly 12. It is understood that the module 22 houses various components for such purposes including but not limited to, printed circuit boards, power supplies, light members, interfaces, and different types of sensors, including multi-axis accelerometer, gyroscopes and/or magnetometers. The module 22 generally includes a housing 170 that supports an interface assembly 171 forming the interface 23, and having electrical connectors that form contacts for cooperation with the interface 20 of the port 14. The interface assembly 171 has a plurality of connectors 172 and a module carrier 173. The connectors 172 each have distal ends that form contacts that collectively define the interface 23 of the module 22. It is understood that the connectors 172 may be insert molded such that material is formed around the connectors 172 to define the module carrier 173. The housing 170 generally has a module base member 175, which may include multiple members (e.g., outer and inner members). The housing 170 further has a module top member 177, which may also include multiple members (e.g., outer and inner top members). The module base member 175, the module top member 177, and interface assembly 171 cooperate to provide a sealed configuration around the connectors 172. The connectors 172 may be considered to have an over-molded configuration in this embodiment. These components also form an inner cavity wherein the housing 170 supports internal components including a printed circuit board 180 that is operably connected to the connectors 172.

It is understood that the module 22 is received in the port 14. A front end of the module 22 is inserted through the central aperture 153 and into the first section 144. The module 22 is dimensioned to generally correspond in size to the tub 29 in an interference fit. In such configuration, the interface 23 on the module 22 is operably engaged with the interface 20 on the port 14 wherein the respective contacts of the interfaces 20, 23 are in surface-to-surface contact. Thus, the construction is such that the interface 23 of the module 22 is forced against the interface 20 of the port 14. The module 22 may have a recess 184 on a rear surface that receives the projection 151 of the housing 24 to assist in retaining the module 22 in the port 14 through a snap connection. A user can easily remove the module 22 from the port by accessing the module 22 with the assistance of a finger recess 29A. Thus, the modules 22 can easily be inserted into the port 14 and removed from the port 14 when necessary such as for charging or transferring data, or when replacing one type of module 22 for one application with a different type of module for a different application, or replacing a power drained module 22 with a freshly charged module 22.

Figure 5:
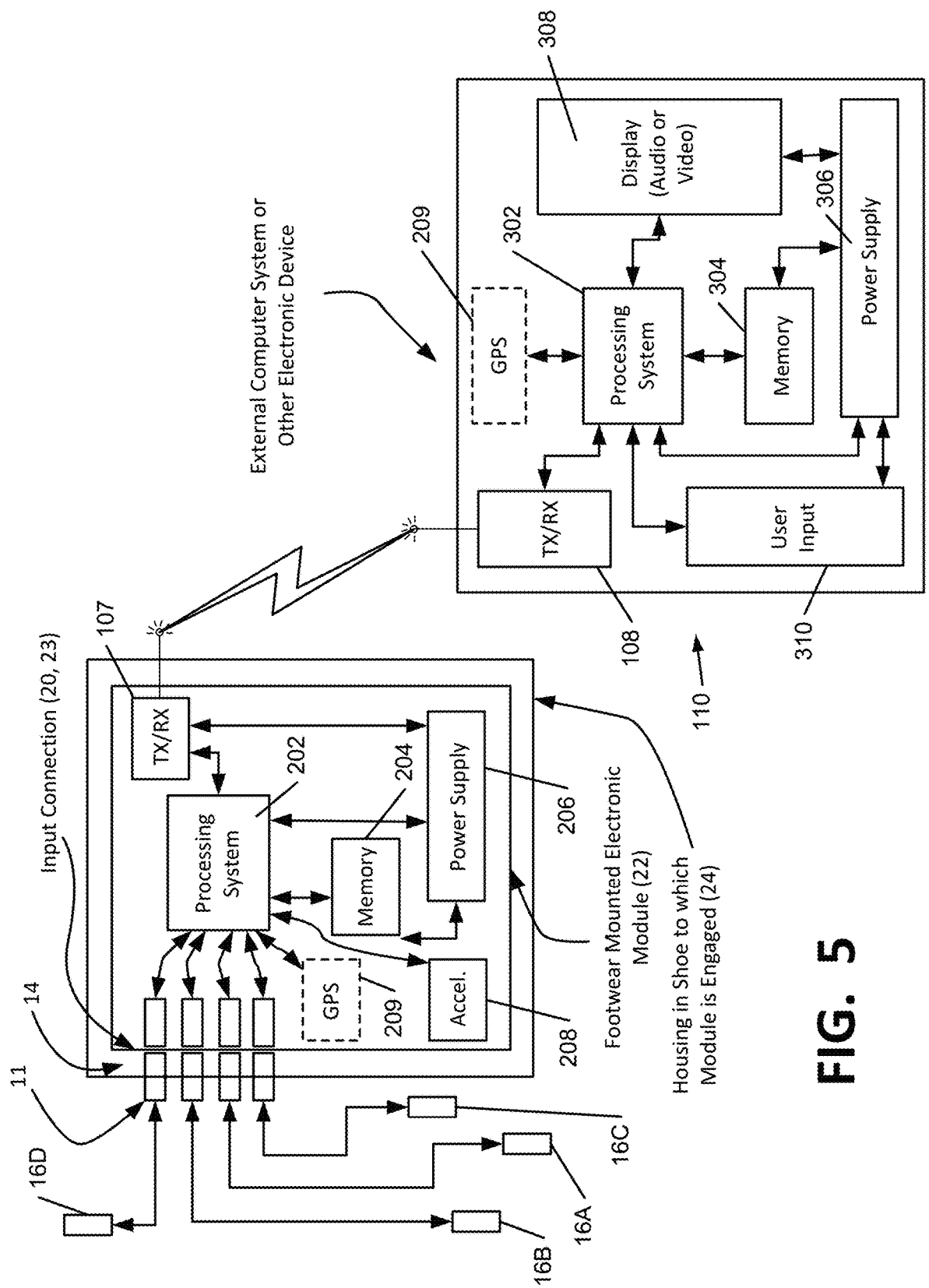
FIG. 5 is a schematic diagram of one embodiment of an electronic module capable of use with a sensor system, in communication with an external electronic device.
Figure 6:
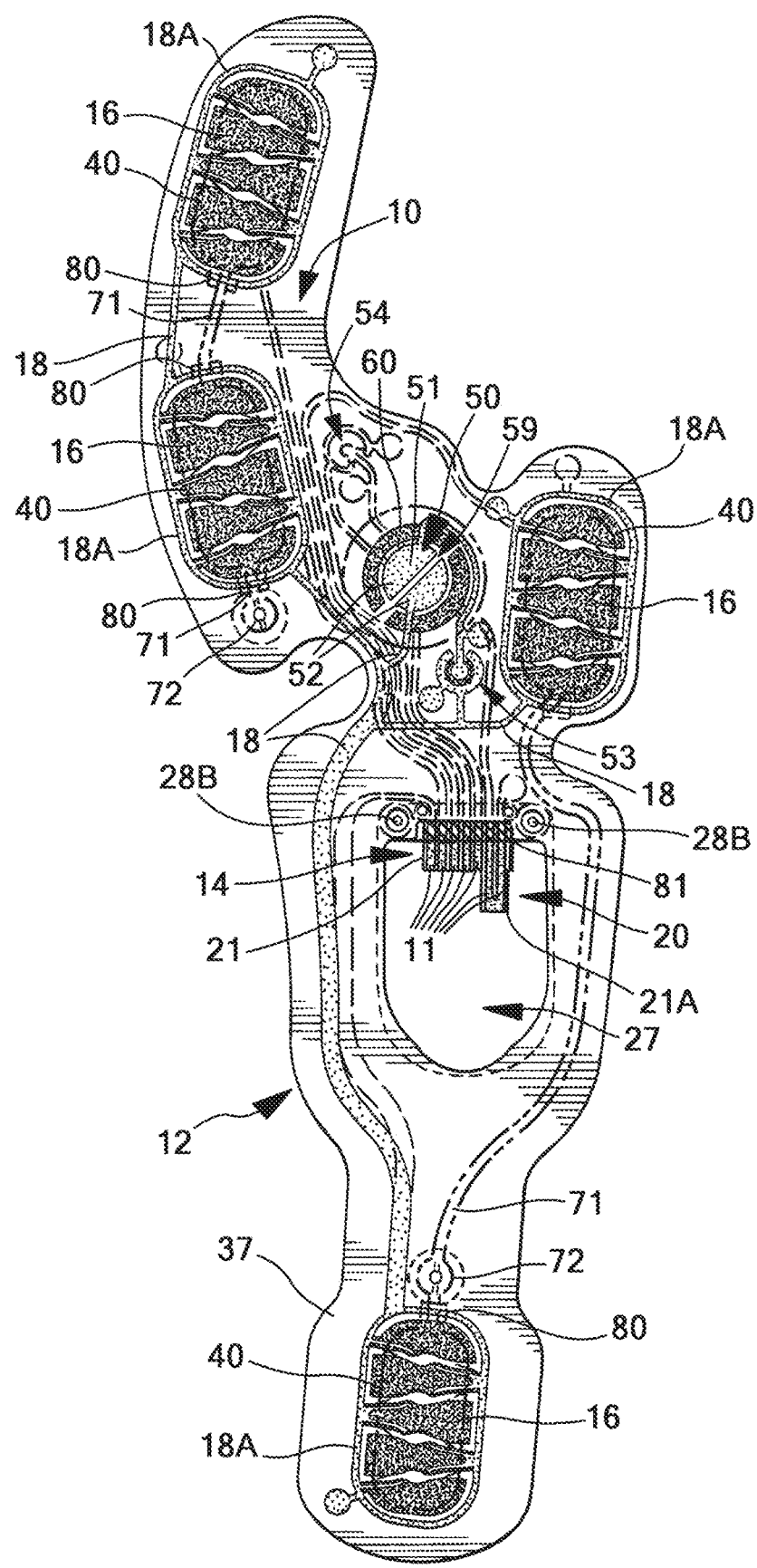
FIG. 6 is a top view of an insert of the sensor system of FIG. 3, adapted to be positioned within the sole structure of an article of footwear for a user's right foot.
Figure 7:
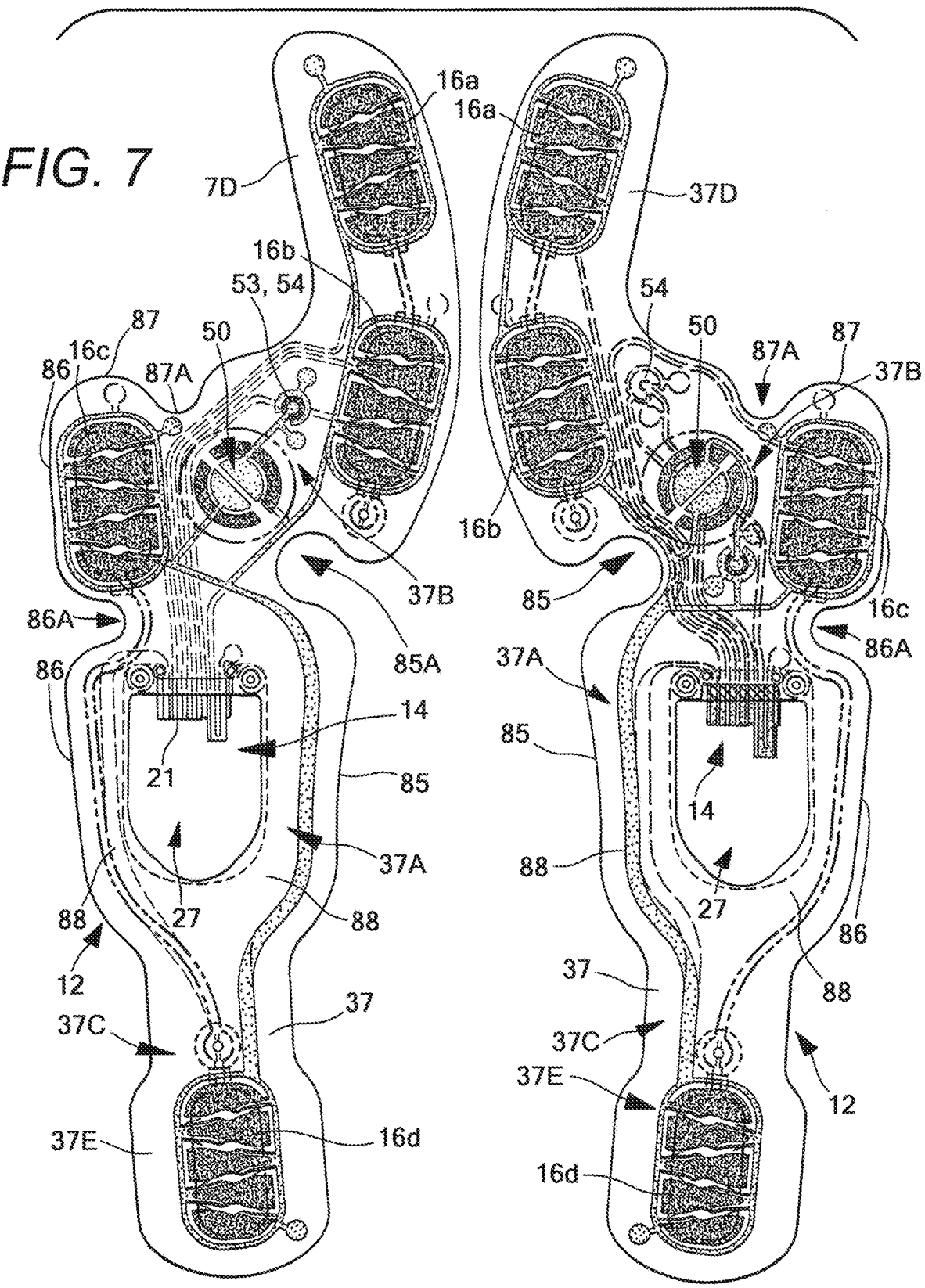
FIG. 7 is a top view of the insert of FIG. 6 and a similar sensor system adapted for use in the sole structure of an article of footwear for a user's left foot.

FIG. 5 shows a schematic diagram of an example electronic module 22 including data transmission/reception capabilities through a data transmission/reception system 107, which may be used in accordance with at least some examples of this invention. While the example structures of FIG. 5 illustrate the data transmission/reception system (TX-RX) 107 as integrated into the electronic module structure 22, those skilled in the art will appreciate that a separate component may be included as part of a footwear structure 100 or other structure for data transmission/reception purposes and/or that the data transmission/reception system 107 need not be entirely contained in a single housing or a single package in all examples of the invention. Rather, if desired, various components or elements of the data transmission/reception system 107 may be separate from one another, in different housings, on different boards, and/or separately engaged with the article of footwear 100 or other device in a variety of different manners without departing from this invention. Various examples of different potential mounting structures are described in more detail below.

In the example of FIG. 5, the electronic component 22 may include a data transmission/reception element 107 for transmitting data to and/or receiving data from one or more remote systems. In one embodiment, the transmission/reception element 107 is configured for communication through the port 14, such as by the contacted or contactless interfaces described above. In the embodiment shown in FIG. 5, the module 22 includes an interface 23 configured for connection to the port 14 and/or sensors 16. In the module 22 illustrated in FIG. 5, the interface 23 has contacts that are complementary with the terminals 11 of the interface 20 of the port 14, to connect with the port 14. In other embodiments, as described above, the port 14 and the module 22 may contain different types of interfaces 20, 23, which may be contacted or wireless. It is understood that in some embodiments, the module 22 may interface with the port 14 and/or sensors 16 through the TX-RX element 107. Accordingly, in one embodiment, the module 22 may be external to the footwear 100, and the port 14 may comprise a wireless transmitter interface for communication with the module 22. The electronic component 22 of this example further includes a processing system 202 (e.g., one or more microprocessors), a memory system 204, and a power supply 206 (e.g., a battery or other power source). In one embodiment, the power supply 206 may be configured for inductive charging, such as by including a coil or other inductive member. In this configuration, the module 22 may be charged by placing the article of footwear 100 on an inductive pad or other inductive charger, allowing charging without removal of the module 22 from the port 14. In another embodiment, the power supply 206 may additionally or alternately be configured for charging using energy-harvesting technology, and may include a device for energy harvesting, such as a charger that charges the power supply 206 through absorption of kinetic energy due to movement of the user.

Connection to the one or more sensors can be accomplished as shown in FIG. 5, but additional sensors (not shown) may be provided to sense or provide data or information relating to a wide variety of different types of parameters, such as physical or physiological data associated with use of the article of footwear 100 or the user, including pedometer type speed and/or distance information, other speed and/or distance data sensor information, temperature, altitude, barometric pressure, humidity, GPS data, accelerometer output or data, heart rate, pulse rate, blood pressure, body temperature, EKG data, EEG data, sweat detection, data regarding angular orientation and changes in angular orientation (such as a gyroscope-based sensor), etc., and this data may be stored in memory 204 and/or made available, for example, for transmission by the transmission/reception system 107 to some remote location or system. The additional sensor(s), if present, may also include an accelerometer (e.g., for sensing direction changes during steps, such as for pedometer type speed and/or distance information, for sensing jump height, etc.). In one embodiment, the module 22 may include an additional sensor 208, such as an accelerometer, and the data from the sensors 16 may be integrated with the data from the accelerometer 208, such as by the module 22 or the external device 110.

In one embodiment, the sensor system 12, the external device 110, or both may contain a GPS device or sensor 209, which may include a GPS antenna and other necessary hardware. Since the sensor system 12 is typically always with the user during use, a GPS device connected to the sensor system 12 may be used to sense the user's position when in use. In the embodiment of FIG. 5, the GPS device 209 is shown to be contained within the module 22, but it is understood that the GPS device 209 may be external to the module 22 and may be in communication with the module 22 in another embodiment. The external device 110 may additionally or alternatively include a GPS device 209, which may enable positional sensing when used in connection with a sensor system 12 as shown in FIG. 21, which contains no electronic module 22. It is understood that the memory 204, 304 and the processing system 202, 302 of the module 22 and/or the external device 110 may include and be configured for processing software for use with the GPS device 209. Operation of the GPS device 209 and its uses in connection with the system 400 and method 500 for analyzing athletic activity are described in greater detail below.

As additional examples, electronic modules, systems, and methods of the various types described above may be used for providing automatic impact attenuation control for articles of footwear. Such systems and methods may operate, for example, like those described in U.S. Pat. No. 6,430,843, U.S. Patent Application Publication No. 2003/0009913, and U.S. Patent Application Publication No. 2004/0177531, which describe systems and methods for actively and/or dynamically controlling the impact attenuation characteristics of articles of footwear (U.S. Pat. No. 6,430,843, U.S. Patent Application Publication No. 2003/0009913, and U.S. patent application Publication No. 2004/0177531 are each entirely incorporated herein by reference and made part hereof). When used for providing speed and/or distance type information, sensing units, algorithms, and/or systems of the types described in U.S. Pat. Nos. 5,724,265, 5,955,667, 6,018,705, 6,052,654, 6,876,947 and 6,882,955 may be used. These patents each are entirely incorporated herein by reference. Additional embodiments of sensors and sensor systems, as well as articles of footwear and sole structures and members utilizing the same, are described in U.S. patent application Ser. No. 12/483,824, published as U.S. Patent Application Publication No. 2010/0063778; U.S. patent application Ser. No. 12/483,828, published as U.S. Patent Application Publication No. 2010/0063779; and U.S. patent application Ser. Nos. 13/399,778 and 13/399,935, all of which applications are incorporated by reference herein in their entireties and made part hereof.

The electronic module 22 can also include an activation system (not shown). The activation system or portions thereof may be engaged with the module 22 or with the article of footwear 100 (or other device) together with or separate from other portions of the electronic module 22. The activation system may be used for selectively activating the electronic module 22 and/or at least some functions of the electronic module 22 (e.g., data transmission/reception functions, etc.). A wide variety of different activation systems may be used without departing from this invention. In any such embodiments, the sensor system 12 may contain a "sleep" mode, which can deactivate the system 12 after a set period of inactivity. In an alternate embodiment, the sensor system 12 may operate as a low-power device that does not activate or deactivate.

The module 22 may further be configured for communication with an external device 110, which may be an external computer or computer system, mobile device, gaming system, or other type of electronic device, as shown in FIGS. 6 and 10-12. The exemplary external device 110 shown in FIG. 5 includes a processor 302, a memory 304, a power supply 306, a display 308, a user input 310, and a data transmission/reception system 108. The transmission/reception system 108 is configured for communication with the module 22 via the transmission/reception system 107 of the module 22, through any type of known electronic communication, including the contacted and contactless communication methods described above and elsewhere herein. It is understood that the module 22 and/or the port 14 can be configured for communication with a plurality of external devices, including a wide variety of different types and configurations of electronic devices, and also including intermediate devices that function to pass information on to another external device and may or may not further process such data. Additionally, the transmission/reception system 107 of the module 22 may be configured for a plurality of different types of electronic communication. It is further understood that the shoe 100 may include a separate power source to operate the sensors 16 if necessary, such as a battery, piezoelectric, solar power supplies, or others. In the embodiment of FIGS. 3-8, the sensors 16 receive power through connection to the module 22.

As described below, such sensor assemblies can be customized for use with specific software for the electronic module 22 and/or the external device 110. A third party may provide such software along with a sole insert having a customized sensor assembly, as a package. The module 22 and/or the overall sensor system 12 may cooperate with one or more algorithms for analysis of the data obtained from the sensors 16, including algorithms stored on and/or executed by the module, the external device 110, or another component.

In operation, the sensors 16 gather data according to their function and design, and transmit the data to the port 14. The port 14 then allows the electronic module 22 to interface with the sensors 16 and collect the data for later use and/or processing. In one embodiment, the data is collected, stored, and transmitted in a universally readable format, so the data is able to be accessed and/or downloaded by a plurality of users, with a variety of different applications, for use in a variety of different purposes. In one example, the data is collected, stored, and transmitted in XML format. In one embodiment, the module 22 detects pressure changes in the sensors 16 utilizing the circuit 10 as shown in FIG. 9, by measuring the voltage drop at the measurement terminal 104b, which is reflective of the changes in resistance of the particular sensor 16 that is currently switched. FIG. 13 illustrates one example of a pressure—resistance curve for a sensor 16, with broken lines illustrating potential shifts of the curve due to factors such as bending of the insert 37. The module 22 may have an activation resistance $R_A$, which is the detected resistance necessary for the module 22 to register the pressure on the sensor. The corresponding pressure to produce such resistance is known as the activation pressure $P_A$. The activation resistance $R_A$ may be selected to correspond to a specific activation pressure $P_A$ at which it is desired for the module 22 to register data. In one embodiment, the activation pressure $P_A$ may be about 0.15 bar, about 0.2 bar, or about 0.25 bar, and the corresponding activation resistance $R_A$ may be about 100 kΩ. Additionally, in one embodiment, the highest sensitivity range may be from 150-1500 mbar. In one embodiment, the sensor system 12 constructed as shown in FIGS. 3-22B can detect pressures in the range of 0.1-7.0 bar (or about 0.1-7.0 atm), and in another embodiment, the sensor system 12 may detect pressures over this range with high sensitivity.

In different embodiments, the sensor system 12 may be configured to collect different types of data. In one embodiment (described above), the sensor(s) 16 can collect data regarding the number, sequence, and/or frequency of compressions. For example, the system 12 can record the number or frequency of steps, jumps, cuts, kicks, or other compressive forces incurred while wearing the footwear 100, as well as other parameters, such as contact time and flight time. Both quantitative sensors and binary on/off type sensors can gather this data. In another example, the system can record the sequence of compressive forces incurred by the footwear, which can be used for purposes such as determining foot pronation or supination, weight transfer, foot strike patterns, or other such applications. In another embodiment (also described above), the sensor(s) 16 are able to quantitatively measure the compressive forces on the adjacent portions of the shoe 100, and the data consequently can include quantitative compressive force and/or impact measurement. Relative differences in the forces on different portions of the shoe 100 can be utilized in determining weight distribution and "center of pressure" of the shoe 100. The weight distribution and/or center of pressure can be calculated independently for one or both shoes 100, or can be calculated over both shoes together, such as to find a center of pressure or center of weight distribution for a person's entire body. In further embodiments, the sensor(s) 16 may be able to measure rates of changes in compressive force, contact time, flight time or time between impacts (such as for jumping or running), and/or other temporally-dependent parameters. It is understood that, in any embodiment, the sensors 16 may require a certain threshold force or impact before registering the force/impact, as described above.

As described above, the data is provided through the universal port 14 to the module 22 in a universally readable format in one embodiment, so that the number of applications, users, and programs that can use the data is nearly unlimited. Thus, the port 14 and module 22 are configured and/or programmed as desired by a user, and the port 14 and module 22 receive input data from the sensor system 12, which data can be used in any manner desired for different applications. The module 22 may be able to recognize whether the data received is related to a left or right shoe, such as through the use of a unique identification chip. The module 22 may process the data differently according to the recognition of L/R shoe, and may also transmit the data to the external device 110 with an identification of whether the data is from a L/R shoe. The external device 110 may likewise process or otherwise handle the data differently based on the identification of L/R shoe as well. In one example, the connections of the sensors 16 to the terminals 11 and the interface 20 may be different between the left and right inserts 37, as shown in FIG. 12 and discussed above. The data from the left insert 37 may be interpreted differently from the data from the right insert 37 in accordance with this arrangement. The module 22 and/or the electronic device 110 may perform similar actions with respect to other identifying information contained on the unique identification chip 92. In many applications, the data is further processed by the module 22 and/or the external device 110 prior to use. In configurations where the external device 110 further processes the data, the module 22 may transmit the data to the external device 110. This transmitted data may be transmitted in the same universally-readable format, or may be transmitted in another format, and the module 22 may be configured to change the format of the data. Additionally, the module 22 can be configured and/or programmed to gather, utilize, and/or process data from the sensors 16 for one or more specific applications. In one embodiment, the module 22 is configured for gathering, utilizing, and/or processing data for use in a plurality of applications. Examples of such uses and applications are given below. As used herein, the term "application" refers generally to a particular use, and does not necessarily refer to use in a computer program application, as that term is used in the computer arts. Nevertheless, a particular application may be embodied wholly or partially in a computer program application.

Further, in one embodiment, the module 22 can be removed from the footwear 100 and replaced with a second module 22 configured for operating differently than the first module 22. For example, the replacement is accomplished by lifting the foot contacting member 133, disconnecting the first module 22 from the port 14 and removing the first module 22 from the housing 24, then inserting the second module 22 into the housing 24 and connecting the second module 22 to the port 14, and finally placing the foot contacting member 133 back into position. The second module 22 may be programmed and/or configured differently than the first module 22. In one embodiment, the first module 22 may be configured for use in one or more specific applications, and the second module 22 may be configured for use in one or more different applications. For example, the first module 22 may be configured for use in one or more gaming applications and the second module 22 may be configured for use in one or more athletic performance monitoring applications. Additionally, the modules 22 may be configured for use in different applications of the same type. For example, the first module 22 may be configured for use in one game or athletic performance monitoring application, and the second module 22 may be configured for use in a different game or athletic performance monitoring application. As another example, the modules 22 may be configured for different uses within the same game or performance monitoring application. In another embodiment, the first module 22 may be configured to gather one type of data, and the second module 22 may be configured to gather a different type of data. Examples of such types of data are described herein, including quantitative force and/or pressure measurement, relative force and/or pressure measurement (i.e. sensors 16 relative to each other), weight shifting/transfer, impact sequences (such as for foot strike patterns) rate of force and/or pressure change, etc. In a further embodiment, the first module 22 may be configured to utilize or process data from the sensors 16 in a different manner than the second module 22. For example, the modules 22 may be configured to only gather, store, and/or communicate data, or the modules 22 may be configured to further process the data in some manner, such as organizing the data, changing the form of the data, performing calculations using the data, etc. In yet another embodiment, the modules 22 may be configured to communicate differently, such as having different communication interfaces or being configured to communicate with different external devices 110. The modules 22 may function differently in other aspects as well, including both structural and functional aspects, such as using different power sources or including additional or different hardware components, such as additional sensors as described above (e.g. GPS, accelerometer, etc.).

One use contemplated for the data collected by the system 12 is in measuring weight transfer, which is important for many athletic activities, such as a golf swing, a baseball/softball swing, a hockey swing (ice hockey or field hockey), a tennis swing, throwing/pitching a ball, etc. The pressure data collected by the system 12 can give valuable feedback regarding balance and stability for use in improving technique in any applicable athletic field. It is understood that more or less expensive and complex sensor systems 12 may be designed, based on the intended use of the data collected thereby.

The data collected by the system 12 can be used in measurement of a variety of other athletic performance characteristics. The data can be used to measure the degree and/or speed of foot pronation/supination, foot strike patterns, balance, and other such parameters, which can be used to improve technique in running/jogging or other athletic activities. With regard to pronation/supination, analysis of the data can also be used as a predictor of pronation/supination. Speed and distance monitoring can be performed, which may include pedometer-based measurements, such as contact measurement or loft time measurement. Jump height can also be measured, such as by using contact or loft time measurement. Lateral cutting force can be measured, including differential forces applied to different parts of the shoe 100 during cutting. The sensors 16 can also be positioned to measure shearing forces, such as a foot slipping laterally within the shoe 100. As one example, additional sensors may be incorporated into the sides of the upper 120 of the shoe 100 to sense forces against the sides.

The data, or the measurements derived therefrom, may be useful for athletic training purposes, including improving speed, power, quickness, consistency, technique, etc., as described in greater detail below. The port 14, module 22, and/or external device 110 can be configured to give the user active, real-time feedback. For example, a coaching or training program may be configured to analyze athletic activity and provide coaching and/or other feedback based on such activity, as described in more detail below. In one example, the port 14 and/or module 22 can be placed in communication with a computer, mobile device, etc., in order to convey results in real time. In another example, one or more vibration elements may be included in the shoe 100, which can give a user feedback by vibrating a portion of the shoe to help control motion, such as the features disclosed in U.S. Pat. No. 6,978,684, which is incorporated herein by reference and made part hereof. Additionally, the data can be used to compare athletic movements, such as comparing a movement with a user's past movements to show consistency, improvement, or the lack thereof, or comparing a user's movement with the same movement of another, such as a professional golfer's swing. Further and more detailed examples are described below.

The system 12 can also be configured for "all day activity" tracking, to record the various activities a user engages in over the course of a day. The system 12 may include a special algorithm for this purpose, such as in the module 22, the external device 110, and/or the sensors 16. The system 12 may also be used for control applications, rather than data collection and processing applications, such as for use in controlling an external device 110, e.g., a computer, television, video game, etc., based on movements by the user detected by the sensors 16.

Figure 10:
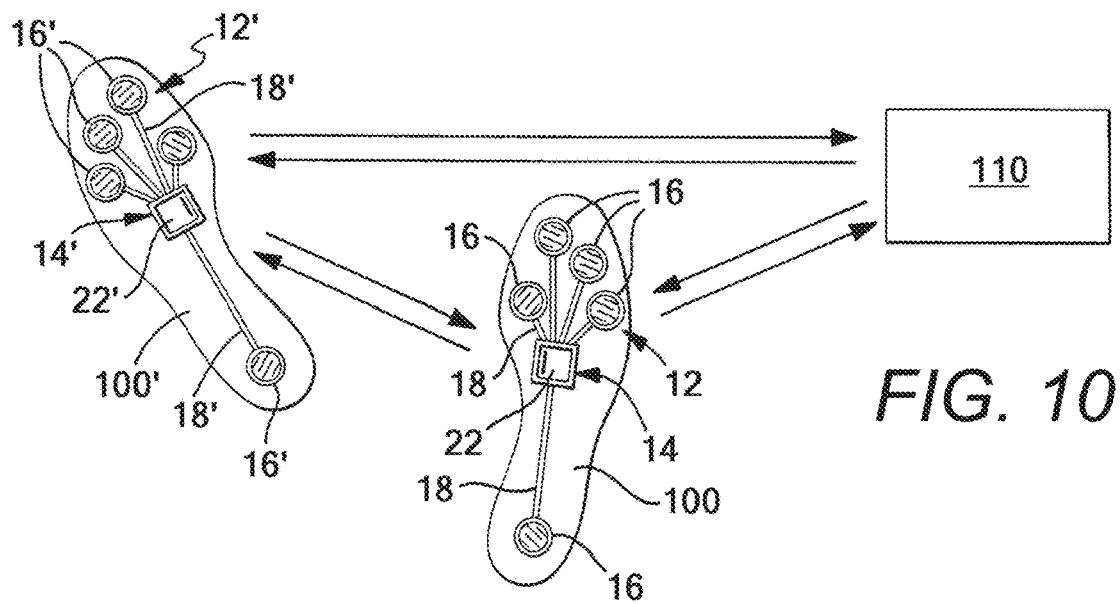
FIG. 10 is a schematic diagram of a pair of shoes, each containing a sensor system, in a mesh communication mode with an external device.
Figure 11:
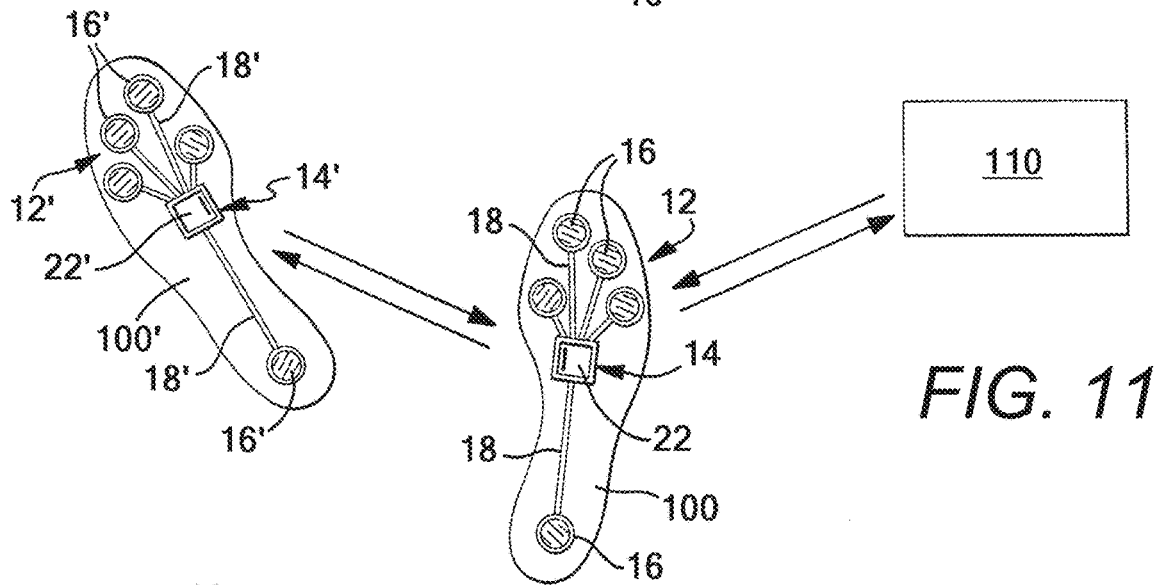
FIG. 11 is a schematic diagram of a pair of shoes, each containing a sensor system, in a "daisy chain" communication mode with an external device.
Figure 12:
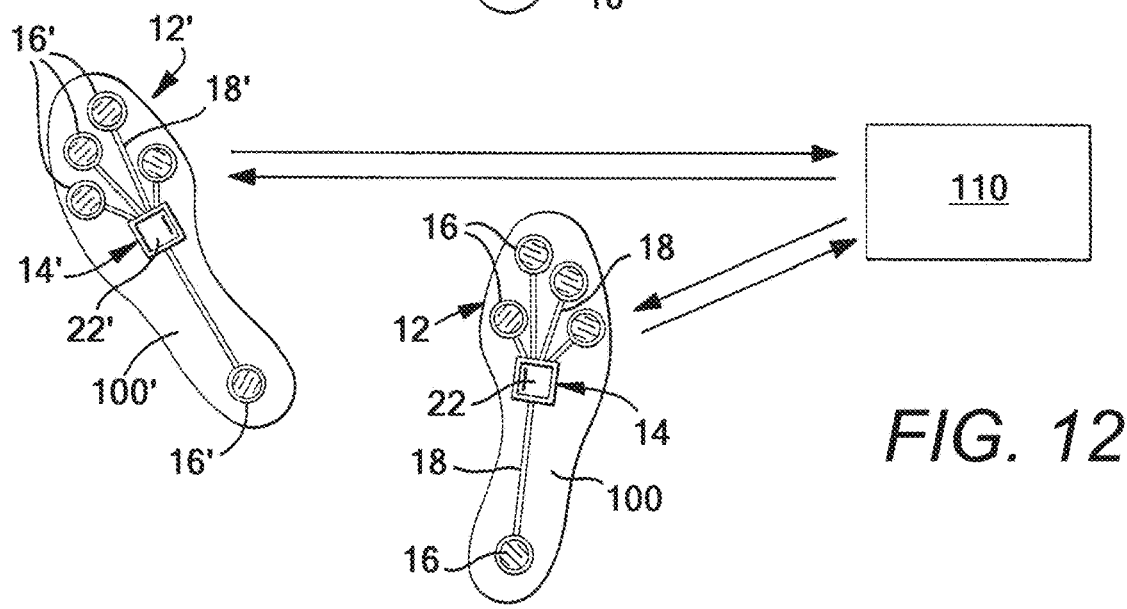
FIG. 12 is a schematic diagram of a pair of shoes, each containing a sensor system, in an independent communication mode with an external device.
Figure 13:
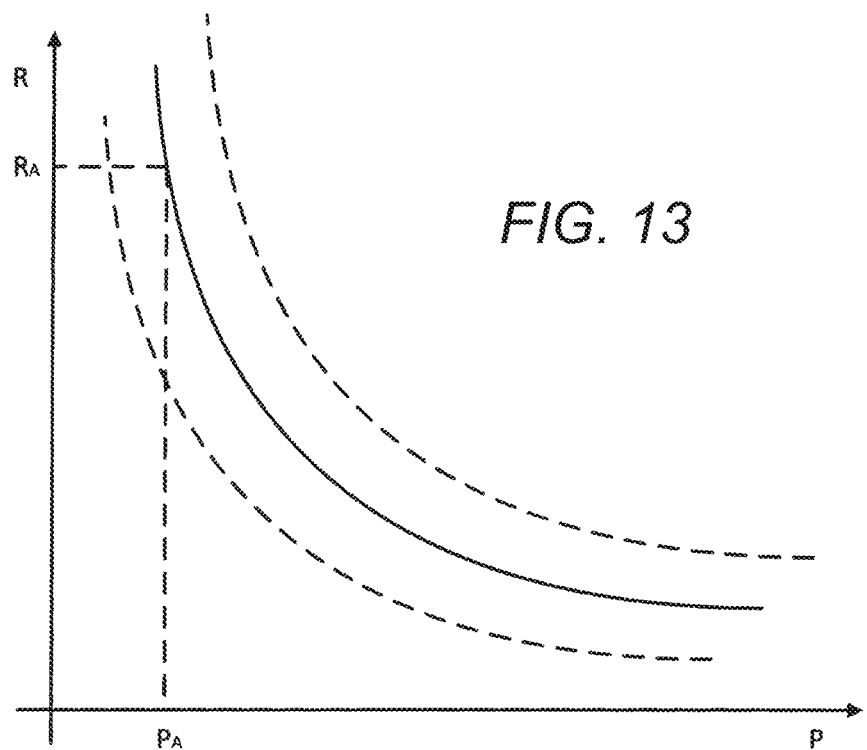
FIG. 13 is a plot showing pressure vs. resistance for one embodiment of a sensor according to aspects of the present invention.

A single article of footwear 100 containing the sensor system 12 as described herein can be used alone or in combination with a second article of footwear 100' having its own sensor system 12', such as a pair of shoes 100, 100' as illustrated in FIGS. 10-12. The sensor system 12' of the second shoe 100' generally contains one or more sensors 16' connected by sensor leads 18' to a port 14' in communication with an electronic module 22'. The second sensor system 12' of the second shoe 100' shown in FIGS. 10-12 has the same configuration as the sensor system 12 of the first shoe 100. However, in another embodiment, the shoes 100, 100' may have sensor systems 12, 12' having different configurations. The two shoes 100, 100' are both configured for communication with the external device 110, and in the embodiment illustrated, each of the shoes 100, 100' has an electronic module 22, 22' configured for communication with the external device 110. In another embodiment, both shoes 100, 100' may have ports 14, 14' configured for communication with the same electronic module 22. In this embodiment, at least one shoe 100, 100' may be configured for wireless communication with the module 22. FIGS. 10-12 illustrate various modes for communication between the modules 22, 22'.

FIG. 10 illustrates a "mesh" communication mode, where the modules 22, 22' are configured for communicating with each other, and are also configured for independent communication with the external device 110. FIG. 11 illustrates a "daisy chain" communication mode, where one module 22' communicates with the external device 110 through the other module 22. In other words, the second module 22' is configured to communicate signals (which may include data) to the first module 22, and the first module 22 is configured to communicate signals from both modules 22, 22' to the external device 110. Likewise, the external device communicates with the second module 22' through the first module 22, by sending signals to the first module 22, which communicates the signals to the second module 22'. In one embodiment, the modules 22, 22' can also communicate with each other for purposes other than transmitting signals to and from the external device 110. FIG. 12 illustrates an "independent" communication mode, where each module 22, 22' is configured for independent communication with the external device 110, and the modules 22, 22' are not configured for communication with each other. In other embodiments, the sensor systems 12, 12' may be configured for communication with each other and/or with the external device 110 in another manner.

Figure 22:
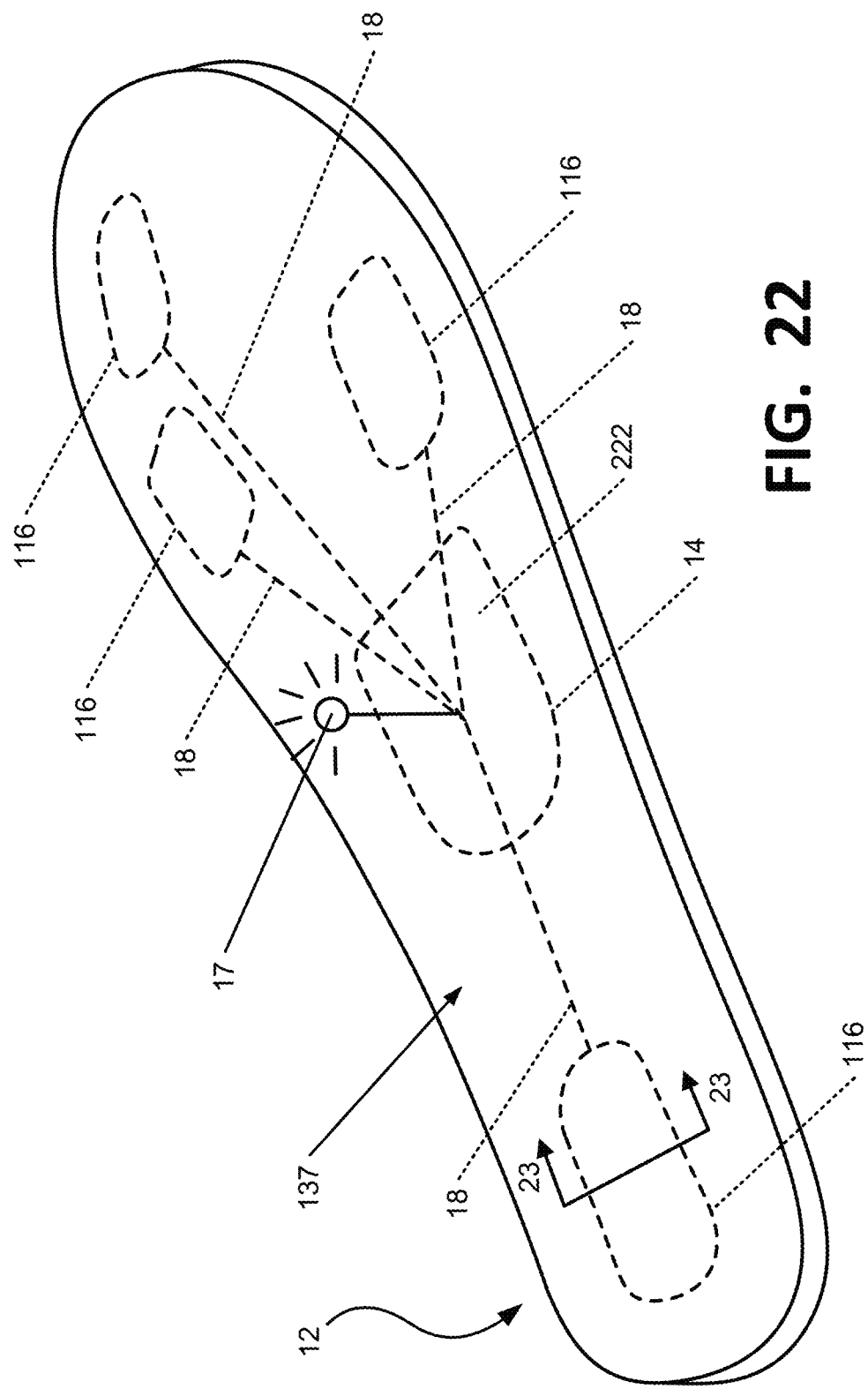
FIG. 22 is a perspective view of a sockliner for an article of footwear including another embodiment of a sensor system.

FIGS. 22-23B illustrate additional embodiments of a sensor system 12 for use with an article of footwear 100 as described above. In one embodiment, as seen in FIG. 22, a footwear sensor system 12 may be incorporated into an insole member 137 that includes four sensors 116 connected to a port 14 by leads 18. The insole member 137 may be a foot contacting member, such as a sockliner, or may be an insole that is positioned underneath a foot contacting member. In another embodiment, the sensor system 12 as shown in FIG. 22 can be incorporated into a different type of sole member. In the embodiment of FIG. 22, the port 14 is connected to antenna 17 for transmitting signals from the sensors 16 to an external electronic device (not shown) as described herein. The port 14 may be connected to an electronic module 22 as described above, and the antenna 17 may be a component of the module. In another embodiment, no electronic module 22 may be included, and the antenna 17 may be a component of the port 14 and configured for direct wireless communication with an external device. It is understood that in any embodiment, the antenna 17 may be accompanied by sufficient hardware and other components to permit transmission of data to the external device. The sensors 116 in the embodiment of FIG. 22 are positioned similarly to the sensors of the insert 37 as shown in FIGS. 3-4 and 6-8.

The sensors 116 in the embodiment illustrated in FIG. 22 may be configured differently from the sensors 16 of the embodiment in FIGS. 3-4 and 6-8 as identified above. For example, in the embodiments illustrated in FIGS. 23A and 23B, the sensors 116 may include contacts 40, 42 that are simple carbon contacts within a cavity 41 in a sealed flexible membrane. The sensors 116 using contacts 40, 42 as in FIGS. 23A and 23B may be configured to dynamically sense changes in force similarly to the sensors 16 of FIGS. 3-4 and 6-8 described above, or may function as binary on/off sensors in another embodiment. In the embodiment of FIG. 23A, the body of the insole member 137 may form the sealed flexible membrane that encloses the sensors 116, with the leads 18 running from the contacts 40, 42 through the insole member 137 to the port 14. In the embodiment of FIG. 23B, the insole member 137 may include a first flexible member 137A that encloses the cavities 41 containing the sensors 116 therein, and a second flexible member 137B connected to the first flexible member 137A. The leads 18 are shown as extending through the first flexible member 137A from the contacts 40, 42 to the port 14, however the leads 18 may extend through at least a portion of the second flexible member 137B in another embodiment. In the embodiment of FIG. 23B, the first and second flexible members 137A, 137B may be made from different materials with different properties. For example, the first flexible member 137A may be made from a flexible, durable, and/or waterproof material, such as thermoplastic polyurethane (TPU), silicone, or other polymer material. The second flexible member 137B may be made from a cushioning material, such as a foam material commonly used in insoles and sockliners.

Embodiments of the system and method for analyzing athletic activity may also be used with a different article of apparel and/or another apparatus for sensing motion. For example, a sensor system for an article of footwear may include sensors such as a 3-axis accelerometer, a 3-axis gyroscope sensor, and/or a compass, which may sense biomechanical movement of the user's foot without the use of pressure/force sensors. It is understood that all of these sensors may be incorporated into a single electronic module in one embodiment, such as the module 22 described above. Additionally, sensor systems for other articles of apparel may utilize a similar module (i.e. having accelerometer, gyroscope, and/or compass sensors) for detecting a different type of biomechanical movement.

Figure 17:
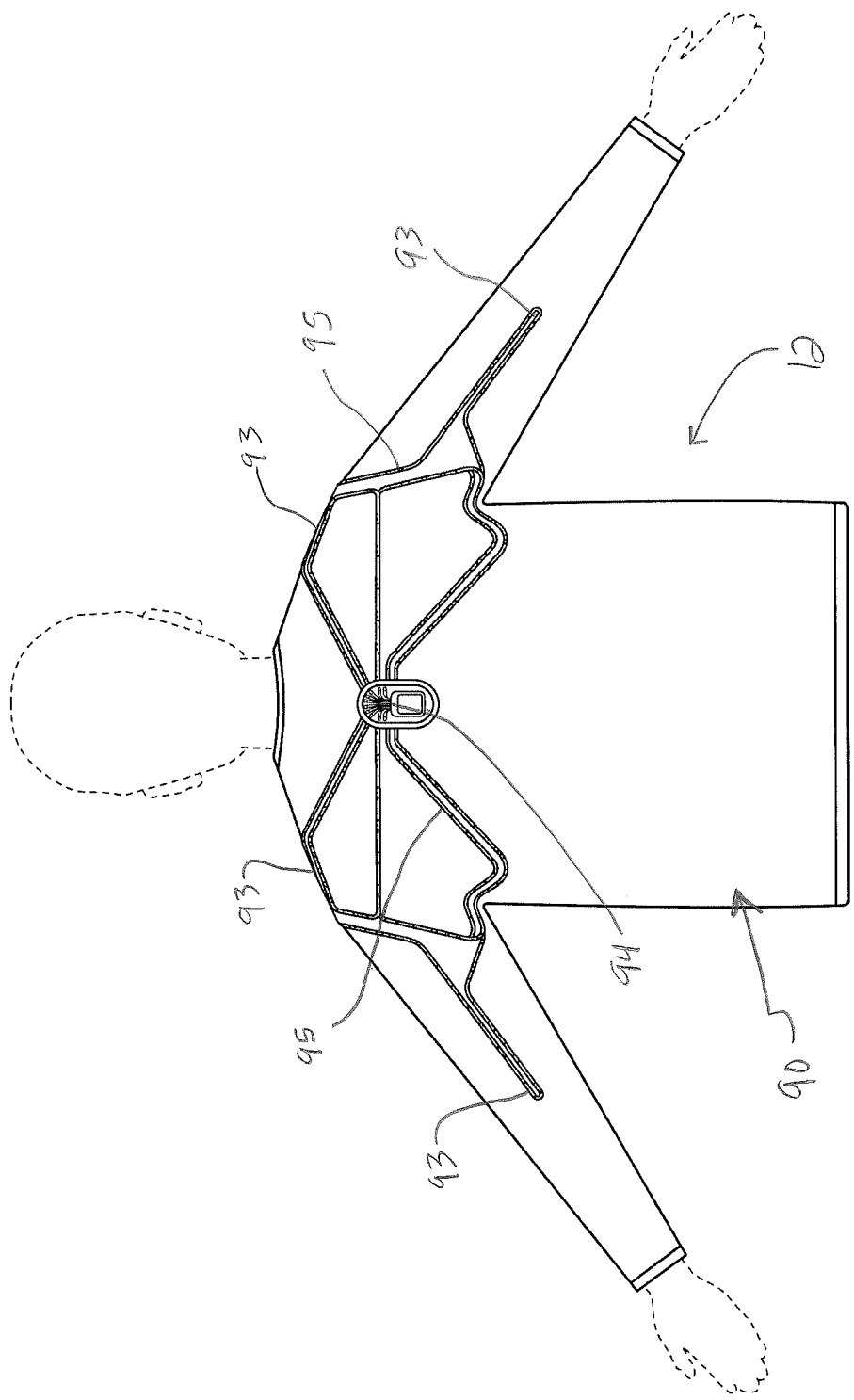
FIG. 17 is a front view of an article of apparel in the form of a shirt, incorporating one embodiment of a sensor system that is configured for use in connection with aspects of the present invention.
Figure 18:
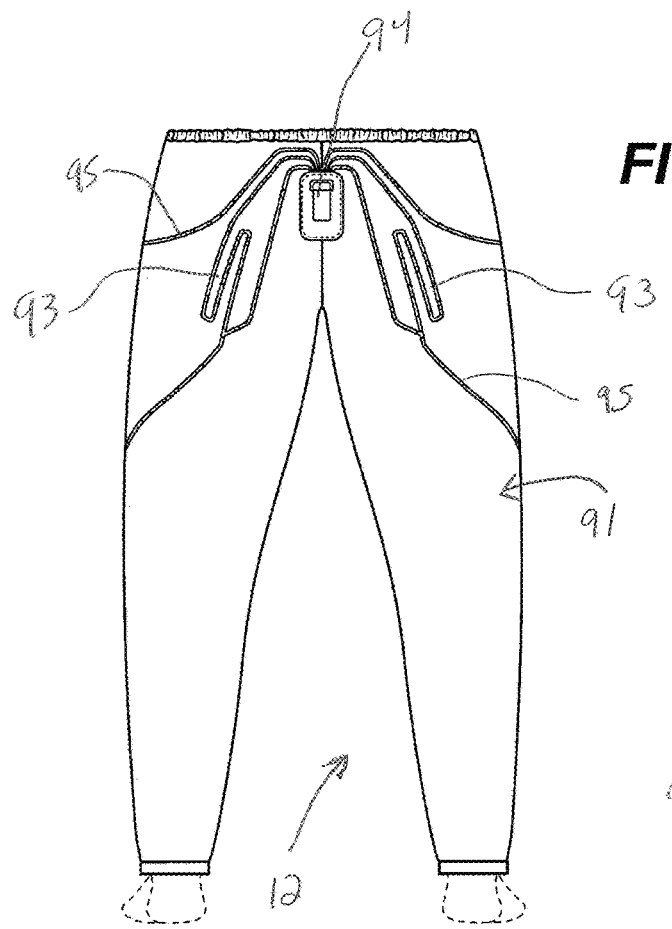
FIG. 18 is a front view of an article of apparel in the form of a legwear, incorporating one embodiment of a sensor system that is configured for use in connection with aspects of the present invention.
Figure 19:
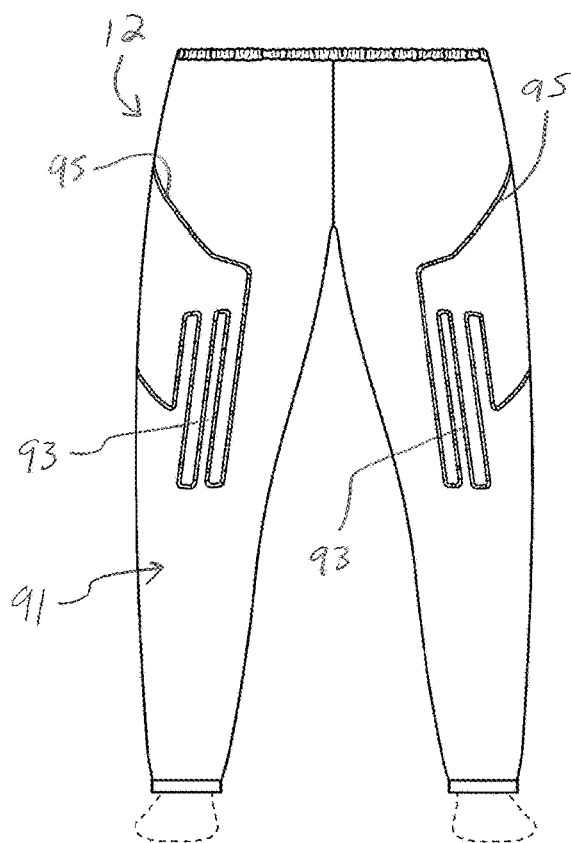
FIG. 19 is a rear view of the legwear of FIG. 18.

As another example, a shirt 90 or a legwear article 91 may be provided with a sensor system 12 for sensing force, movement, and/or other biomechanical parameter, as shown in FIGS. 17-19. The shirt 90 and legwear 91 in these embodiments include sensors 93 at joint areas that are in communication with a port 94 via a plurality of leads 95. A module 22, which may be provided according to other embodiments described herein, may be connected to the port 94 to collect data from the sensors 93 reflecting a biomechanical parameter. In one embodiment, the sensors 93 and leads 95 may be formed of a flexible polymer material with a conductive particulate material dispersed therein. The leads 95 may have a high density of the conductive material to minimize variations in conductivity, and the sensors 93 may have a lower density of the conductive material, so that compression and/or other deformation of the sensors 93 may change the conductivity/resistivity of the sensors. This change in conductivity/resistivity may be used to indicate force and/or movement at the sensors 93, similar to the footwear sensor system 12 described above. The module 22 may collect such data and communicate it to an external device 110, as similarly described above. It is understood that the module 22 may be configured specifically for use in collecting data from the sensors 93. In these embodiments, the system 400 may be used to provide coaching and/or other feedback to a user to assist the user in developing a specific biomechanical movement pattern, such as for use in an athletic activity. Examples of such biomechanical movement patterns include a throwing motion, a basketball shooting motion, a jumping form for hurdling or high-jump competition, a swinging motion (e.g. golf, baseball, hockey, tennis), a dancing motion, etc. It is also understood that sensor systems 12 as described above with respect to the footwear 10, shirt 90, and legwear 91 may be used in connection with other articles of apparel or other apparatuses connected to other parts of the body. It is also understood that any such sensor systems may include sensors 16, 93 of the either or both of the types described above, in addition to or in combination with further types of sensors. In further embodiments, the system 400 and method 500 may be used in connection with other sensor systems or apparatuses for sensing motion, including sensor systems incorporated into other articles of apparel.

Example embodiments of a system 400 for analyzing athletic activity are shown in FIGS. 20 and 21, and include at least sensor system 12 configured to sense a biomechanical parameter of a user while the user is in biomechanical motion, as well as at least one electronic device 110 in communication with the sensor system 12 so that the electronic device 110 can receive data gathered by the sensor system 12. The electronic device 110 is configured for analyzing the data to determine whether a deviation from a desired biomechanical movement pattern exists in the biomechanical movement of the user, and may generate an indication to the user when deviation from the desired biomechanical movement pattern is determined to exist. Deviation may be determined by using a biomechanical movement template, in one embodiment, as described in greater detail below. Such templates may be stored in the memory 304 of the electronic device 110. In this embodiment, the electronic device 110 can compare the data received from the sensor system 12 to a biomechanical movement template corresponding to the desired biomechanical movement pattern to determine any deviation from the template. Deviation from the template may indicate deviation from the biomechanical movement pattern. It is understood that the determination of "deviation" may include threshold variations, where the data is not considered to deviate from the template unless the threshold is exceeded.

Movement templates may be obtained in a variety of ways. As one example, a template may be included in software applications stored in the memory 304 of the electronic device 110 and/or obtained from other tangible storage media. As another example, a template may be accessed by communication with another electronic device 110 (including from the electronic module 22), such as a download over the internet or other network. As a further example, a template may be created by the user, by either selecting a desired movement pattern or recording an actual movement pattern of the user or another person. It is understood that any such templates may be stored in the memory 304.

Examples of biomechanical movement templates that may be used in connection with embodiments of the system 400 and method 500 include various footstrike and other running templates, such as templates for footstrike pattern, footstrike load or force, gait speed, stride length, footstrike contact time, speed, distance, footstrike cadence, pronation/supination, stride force, upper body movement, lean, asymmetry, posture, and others. Data gathered by a sensor system 12 incorporated within an article of footwear 100, such as shown in FIGS. 3-4 and 6-8 or in FIGS. 22-23B, may be compared with one or more of these templates. Additional examples of biomechanical movement templates that may be used in connection with embodiments of the system 400 and method 500 include templates for: running form, throwing form (which may be tailored to a specific activity such as baseball, football, softball, cricket, etc.), basketball shooting form, swing form (which may be tailored to a specific activity such as baseball, golf, tennis, hockey, etc.), kicking form (e.g. for soccer or football), ice skating or roller skating form, jumping form, climbing form, weightlifting or other stationary exercise form, posture, and many other templates corresponding to many other biomechanical movement patterns. A sensor system 12 as shown in FIGS. 17-19 and/or another type of sensor system may additionally or alternately be used in connection with at least some of these templates. Templates may be created based on a number of different subjects, including a preferred or "proper" biomechanical movement pattern (such as with input of coaches, trainers, sports medicine professionals, etc.), a past biomechanical movement pattern of the user, a biomechanical movement pattern of a famous athlete or other famous person, etc.

In one embodiment, a plurality of templates may be available for a single activity and/or for different activities. For example, multiple different types of templates may be available for use for a single activity, such as a footstrike pattern template, a footstrike load template, and other templates for use in a running activity. Multiple templates may be used by the device 110 simultaneously for analyzing multiple different biomechanical movement patterns in a single activity, in one embodiment. As another example, multiple different templates of the same type may be available for use, such as heel-strike, midfoot-strike, and forefoot-strike footstrike pattern templates. Further, the template(s) used in connection with an activity may be manually selected by the user or another person, automatically selected by the processor 302, or a combination of such techniques. For example, a user or another person may manually select a specific footstrike pattern template or a specific throwing form template to coach the user to a specific footstrike pattern or throwing motion. As another example, the user may select a specific activity, and the device 110 may automatically select a template based on the desired activity, such as selecting a different footstrike pattern template for sprinting vs. distance running vs. football playing. It is understood that the automatic selection may incorporate input from the user, such as past performance data, answers to posed questions, etc. As a further example, a manually or automatically selected template may be further revised (either manually or automatically) based on characteristics of the user, such as height, weight, age, BMI, past performance, etc. Other methods for selection of templates may be used as well.

In one embodiment, biomechanical movement templates may vary for different users. Different users may utilize different templates, and the content of similar templates may vary depending on the characteristics (e.g. height, weight, age, BMI, fitness, etc.) of an individual user. A device 110 utilizing the templates may provide for user identification in one embodiment, such as through a user name, passcode, biometric ID, etc., and may store templates customized for each identified user. In another embodiment, a device 110 utilizing the templates may also provide for automatic selection of templates based on user characteristics, without specifically identifying the user.

Figure 24:
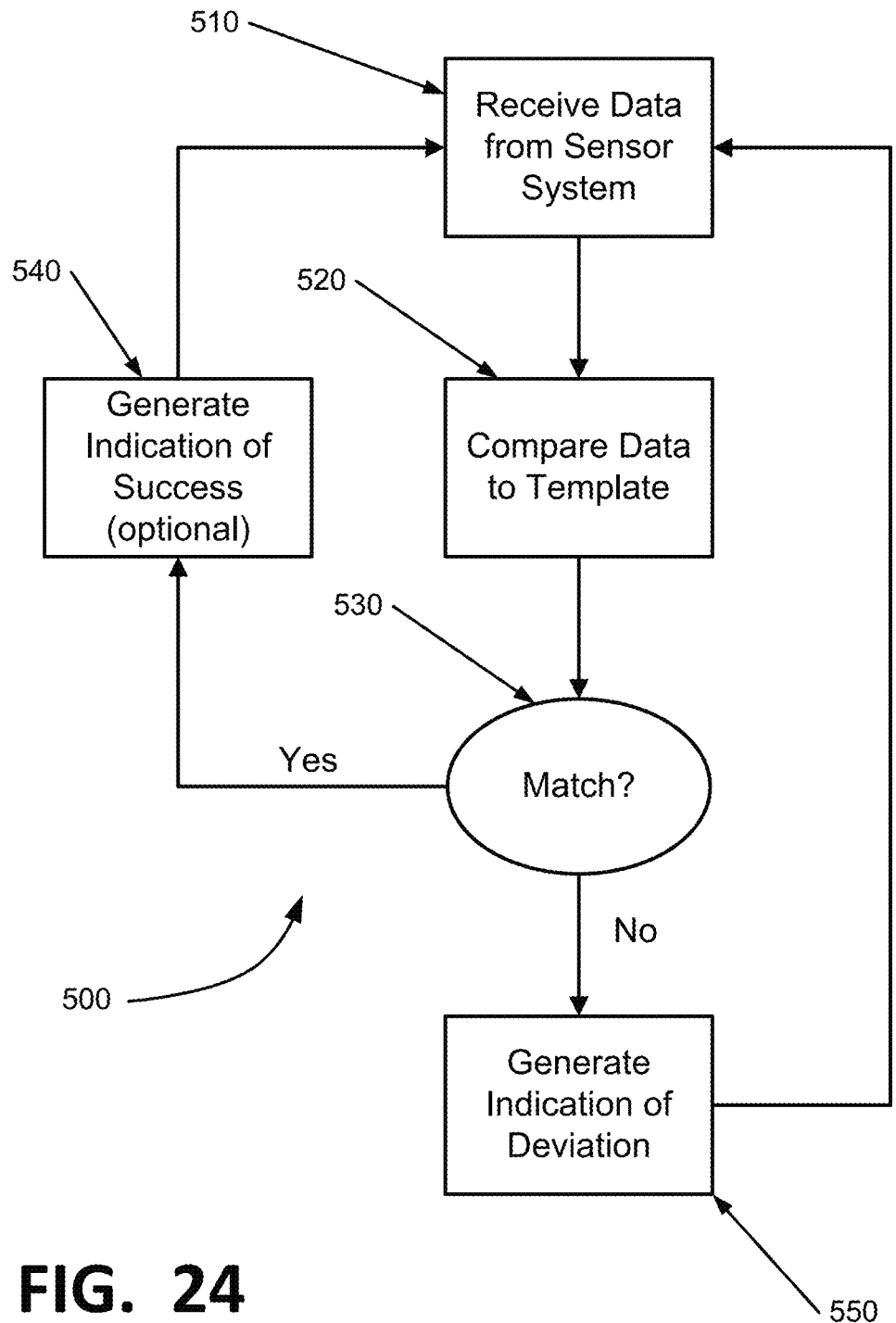
FIG. 24 is a flow diagram illustrating one embodiment of a method for analysis of an athletic activity utilizing a template for biomechanical movement.

FIG. 24 illustrates one example embodiment of a method 500 for analyzing athletic activity that may be used with a system 400 such as shown in FIGS. 20-21 or another type of system 400 for analyzing athletic activity as described herein. It is understood that the embodiment of the method 500 in FIG. 24 is illustrated with respect to the actions of an electronic device 110 (or devices) that are in communication with a sensor system 12 as described above, and that other actions may be performed by other components, such as the module 22 of the sensor system. For example, prior to the device 110 receiving data from the sensor system 12, in one embodiment the module 22 gathers data sensed by the sensors 16 and transmits the data to the device 110. The module 22 may optionally perform some processing of the data prior to transmission. Additionally, actions performed by the device 110 and/or the module 22 may involve the processors 202, 302, memories 204, 304, and/or other components of such devices.

At step 510 in the method 500 as illustrated in FIG. 24, the device 110 receives data from the sensor system 12, which may be transmitted by the module 22 or in another manner. In one embodiment, the device 110 receives data from the sensor system 12 in real time, in a substantially continuous manner, which may be accomplished by periodic transmission of individual data units or packets of data in various embodiments. In other embodiments, the device 110 may receive collected past data incrementally or in a single transmission. In a further embodiment, the device 110 may receive data from a plurality of different sensor systems.

The device 110 then analyzes the data to determine whether a deviation from a desired biomechanical movement pattern exists in the biomechanical motion of the user. In the embodiment of FIG. 24, the device 110 determines whether a deviation exists by comparing the data to one or more templates that have been selected, at step 520, and determining whether a match exists between the data and the template, at step 530. Many different types of criteria may be used in determining whether a match or deviation exists, in various embodiments. Additionally, as described above, various predetermined thresholds may be used in determining deviation, whereby deviation is not determined to exist unless the degree of deviation exceeds a particular threshold. FIGS. 25-28 illustrate graphical depictions of comparisons between measured data and one or more templates, and these depictions are discussed in greater detail below.

After determining whether a deviation exists, the method 500 either ends, or the device 110 continues analyzing additional data received from the sensor system 12, at step 510. If no deviation is detected, the device 110 may optionally generate an indication of success to the user in one embodiment, at step 540. Such indications of success may take one or more different forms, including any forms described herein with respect to indications of deviation. If a deviation is detected, then the device 110 generates an indication of the deviation to the user, at 550. Such an indication may be in one or more different forms, including visual, tactile, audible, and other indication. For example, a visual indication may be provided on a display of the device, where the indication may be displayed as text, graphics, color (e.g. green for success or red for deviation), or other visual display. A visual indication may also be provided by a blinking light or other component. As another example, a tactile indication may be provided by a vibration motor or other vibration device associated with the device 110. Different vibration patterns, intensities, frequencies, etc. may be used to indicate differing results (success vs. failure). As a further example, an audible indication may be provided by a speaker or other audio device associated with the device 110. An audible indication may take the form of spoken words, beeps, sirens, bells, and other sounds that may be understood to indicate success or failure. Further different types of indications may be generated, and it is understood that the type(s) of indication provided may depend on the capabilities of the device. Combinations of indications can also be utilized. The indication may additionally or alternately be generated by transmitting a signal to another device to cause the other device to produce an indication as described above. Additionally, the indications of success and/or failure may be indicated to the user in real time, or may be indicated at a later time, such as after the activity is completed.

In one embodiment, the user may be provided the option to select one or more different types of indications to be generated, and may select different "good" and "bad" indicators. In another embodiment, the device 110 may provide the ability for the user to select a "tone" of the indication. For example, the device 110 may provide the ability for a user to select a "coach" mode where indications of success or failure are more authoritative and demanding, a "buddy" mode where such indications are more supportive and encouraging, a "competitor" mode where such indications are more competitive in nature, a mode where a fanciful or comical character provides such indications in an entertaining or amusing manner, and the like. Such indication modes may be accompanied by an avatar displayed by the device 110 to appear to be speaking to the user. The user may further be provided the ability to select and/or design avatars utilized by the device 110, including visual appearance, sound, personality, etc.

The device 110 may provide more information in the indication, in addition to information on whether the user's movement deviated from the template. An indication of deviation as described above may also include an indication of the degree of deviation in one embodiment. For example, on a device 110 with a visual display 308, a degree of deviation may be indicated by a numerical value, a graphical depiction (e.g. FIGS. 25-28), a display of different colors, shades, intensities, and other such visual indications or combinations of the same to indicate greater or lesser deviation. As another example, on a device 110 with an audio output, sounds may be emitted that vary in pitch, volume, rhythm, etc., and other such audible indications or combinations of the same, to indicate greater or lesser deviation. As a further example, on a device 110 with tactile output (e.g. a vibration motor), different tactile sensations may be generated to indicate greater or lesser deviation, such as vibrations of different intensities, rhythms, etc., and other such tactile indications or combinations of the same. The device 110 may be further provided with additional performance monitoring applications to allow the user to monitor his/her performance metrics dynamically during an activity and/or retroactively after the completion of an activity.

A device 110 as described herein may include one or more applications or other software to provide coaching information to a user, which may utilize one or more different types of templates as described herein. Templates may be included within the software and/or may be obtained from outside sources, such as by customized creation, download from external devices and/or storage media, etc. Such software may be configured specifically for a single activity, biomechanical movement pattern, or type of sensor system, or may be used in connection with multiple activities, multiple biomechanical movement patterns, and/or multiple different types of sensor systems. In one embodiment, the software may be able to incorporate multiple templates for a single activity, utilizing data input from one or multiple types of sensor systems. Additionally, such software may incorporate user data, such as height, weight, gender, BMI, actual recorded movement data, etc., and data of these types may be manually entered, downloaded from a separate storage media, collected from measurements by a sensor system 12, and/or obtained through other means. Further, such software may provide for various degrees of user control and interaction. For example, a user may be able to select a specific activity and a specific type or types of coaching input for the software to provide. As another example, a user or another person (e.g. a coach, trainer, therapist, medical professional, etc.) may be able to specifically design or create a template or modify an existing template.

A device 110 provided with such software may display real-time results of the activity, such as real-time biometric movement data, real-time indications of compliance and/or deviation from a desired template, real-time information from other users (e.g. other participants in a competition or activity group, social networking contacts, etc.), and other types of real-time activity. It is understood that real-time results may be more effectively presented in connection with a compact mobile device 110, which the user may carry/wear during the activity. A device 110 provided with such software may additionally or alternately provide collected past information, such as by providing an activity summary with data and/or analysis of the activity. For example, the software may generate a post-activity summary, which may include performance data, success in complying with a desired template, comparison to other users or to the user's past performance, etc., which may be presented in various forms.

In one embodiment, the device 110 and/or associated software may provide gradual coaching feedback to incrementally guide a user to a desired biomechanical movement pattern. Gradual or incremental coaching may be useful or even necessary in some circumstances, as rapid changes in biomechanical movement patterns can increase risk of injury. One way of accomplishing gradual or incremental coaching by the device 110 altering the biomechanical movement template to return to a more familiar or normal template for the user after a designated amount of usage, such as a designated amount of time, repetitions, travel distance, etc. For example, a predominately heel-striking runner may wish to gradually change his/her footstrike pattern to a predominately midfoot or forefoot strike pattern, e.g., over the course of 3-6 months. In one embodiment, gradual conversion can be accomplished by utilizing the desired footstrike template for only small portions of a run initially, and then returning to the normal (e.g. heel-strike) template and/or ceasing template usage after the designated portion is completed. The template usage can be gradually increased with successive runs. As one example, the desired footstrike template may be used for about 10% of the length of each run initially, and the usage of the desired template may increase by 5% each week until 100% usage is reached. It is understood that such gradual or incremental coaching may be utilized to assist conversion from any footstrike pattern to any other footstrike pattern, or between different biomechanical movement patterns of other types.

Figure 27:
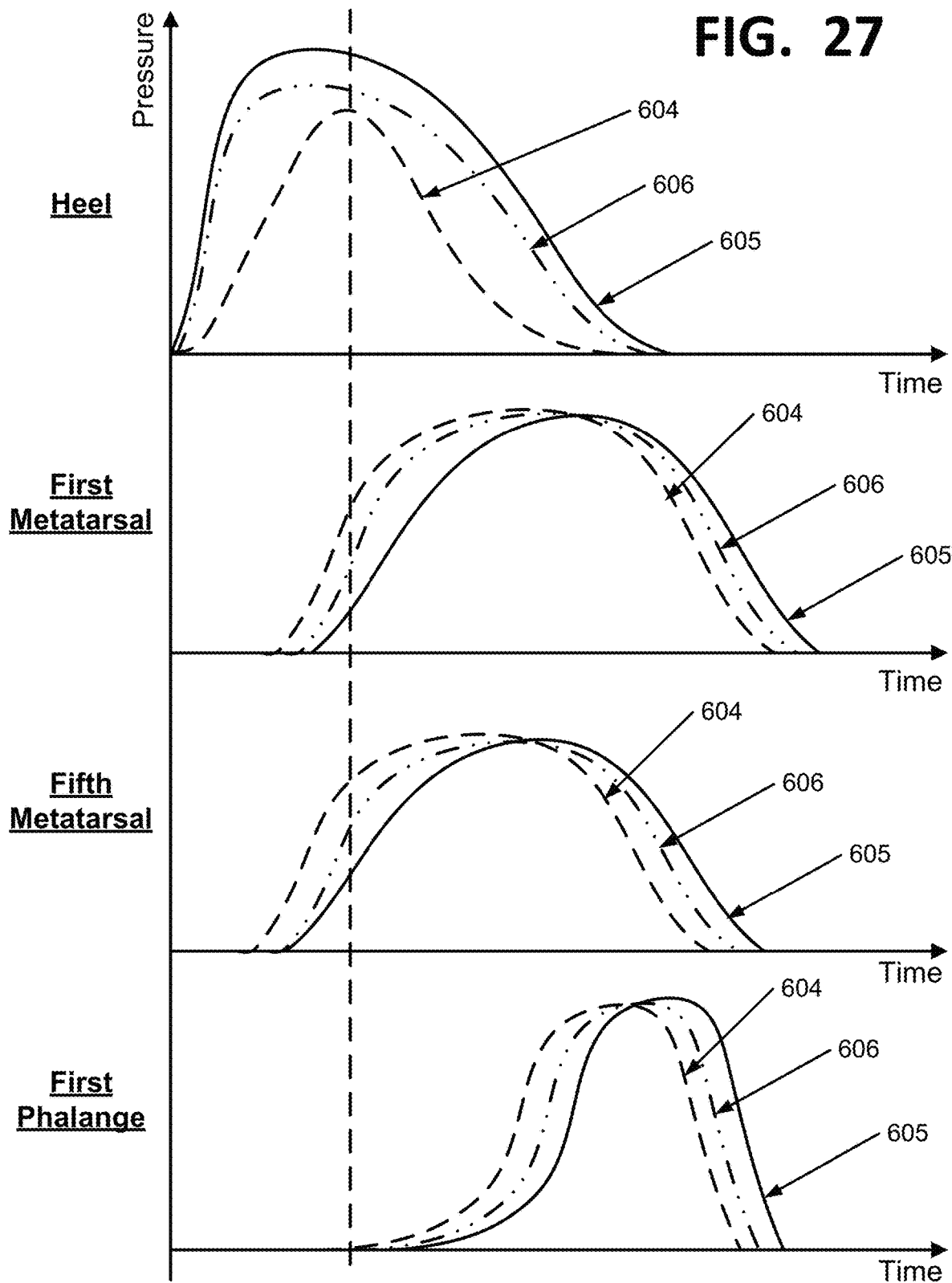
FIG. 27 is a graph showing pressure measured over time for a footstrike using four sensors located in different locations on an article of footwear, with even-length broken lines illustrating the footstrike template of FIG. 25 and uneven-length broken lines illustrating one embodiment of an intermediate footstrike template.

In another embodiment, one or more intermediate templates may be used, which may guide a user to a movement pattern that is part-way between the user's present movement pattern and the ultimate desired movement pattern. As one example, a predominately heel-strike runner trying to convert to a midfoot or forefoot strike may utilize a footstrike template that encourages less of a heel-strike than the runner's current footstrike, but not as strong of a midfoot or forefoot strike as the ultimate desired movement pattern. FIG. 27 illustrates an intermediate template 606 located between a runner's actual movement data 605 and the ultimate desired footstrike template 604, as described below. Multiple intermediate templates may be utilized in some embodiments to more gradually achieve conversion from one biomechanical movement pattern to another. Intermediate templates may also be subject to gradual use as described above.

It is understood that similar gradual use of templates and/or use of intermediate templates may be applied to coaching for other biomechanical movement patterns, and that in other applications, a more or less gradual approach may be appropriate. Additionally, the device 110 and associated software may include algorithms to automate aspects of such gradual or incremental coaching. For example, in one embodiment, the device 110 may automatically engage in gradual template usage and/or intermediate template usage, or may have a user selection feature for such automatic utilization. In another embodiment, the device 110 may provide for specific user selection, such as selection of specific intermediate templates or selection of the rate at which gradual template usage may progress. In a further embodiment, the device 110 may provide for specific user design of templates, including intermediate templates, and for specific user design of training programs.

Figure 25:
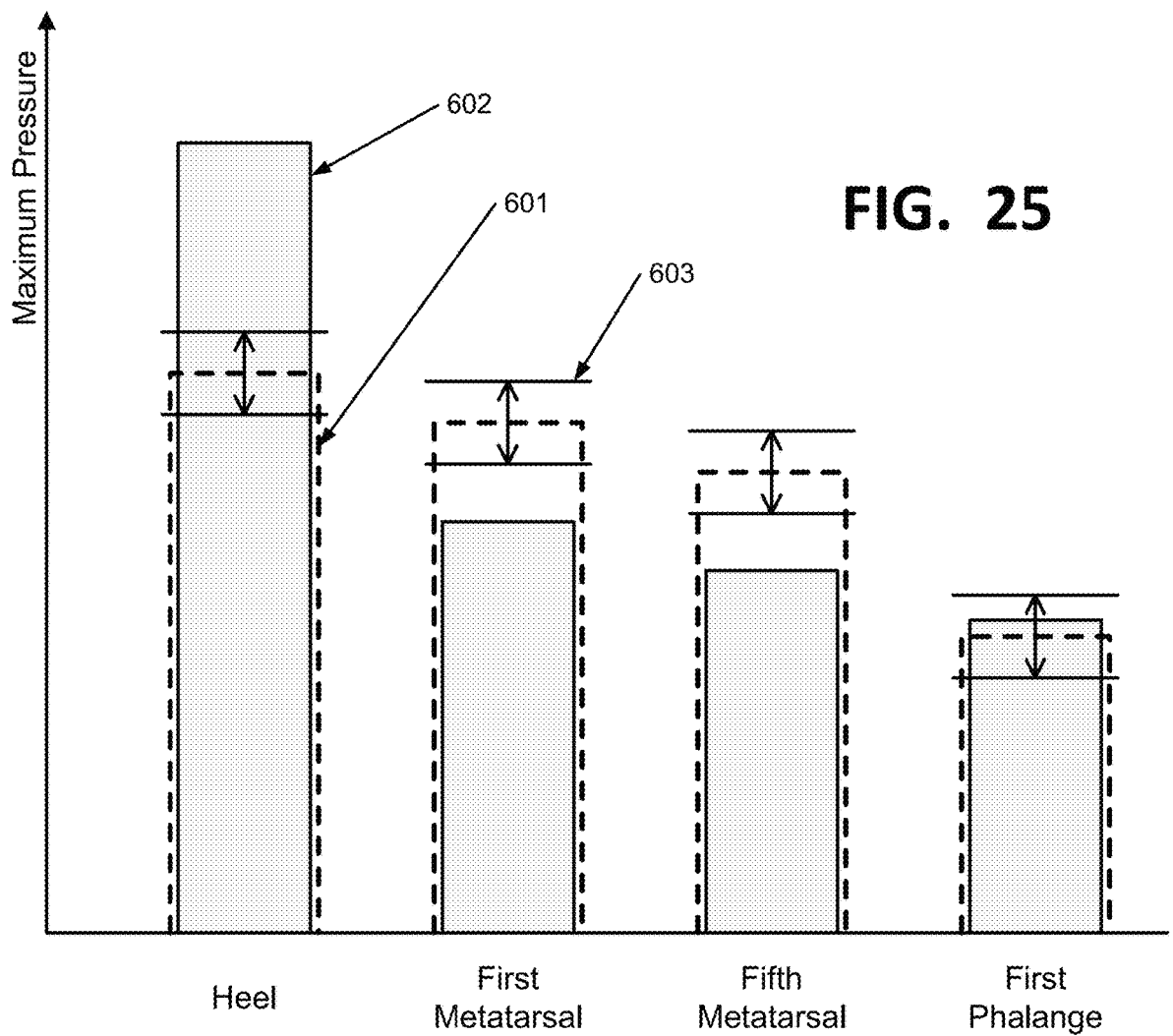
FIG. 25 is a bar graph showing maximum pressure measured for a footstrike using four sensors located in different locations on an article of footwear, with broken lines illustrating one embodiment of a footstrike template.

FIGS. 25-28 illustrate graphical depictions of various footstrike pattern templates that may be used according to one embodiment, as well as graphical depictions of comparisons of actual data to such templates. It is understood that FIGS. 25-28 illustrate conceptual graphical depictions of processing that may occur by the device 110 in analyzing athletic activity. In one embodiment, the device 110 may generate graphical depictions reflecting current/real-time or past analysis that may appear similar to FIGS. 25-28, such as by GUI display, printing, or other means. FIG. 25 illustrates one example of a footstrike template 601 (in broken lines) based on maximum pressure or force measured at locations of the sensors 16 in the sensor systems 12 in FIGS. 3-4 and 6-8 and FIGS. 22-23B. Deviation from the template 601 can occur if excessive or insufficient pressure or force is exerted on one or more of the sensors 16. Hypothetical data 602 collected from an athletic activity is shown as solid bars in FIG. 25, and threshold tolerances 603 are also illustrated. As seen in FIG. 25, the pressure measured at the heel exceeds the desired value in the template 601 and is outside the threshold tolerance 603, while the pressure measured at the first and fifth metatarsals are less than the desired values and are also outside the threshold tolerances 603. Additionally, in this example, the pressure measured at the first phalange is slightly greater than the desired value of the template 601, but is within the threshold tolerance 603. Thus, in this example, the data measured at the heel, first metatarsal, and fifth metatarsal would be considered to deviate from the template, and the data measured at the first phalange would be in compliance. This may be read as a footstrike that deviates from the template and constitutes a footstrike that is too heavy at the heel, depending on the rules governing the definition of deviation. In various embodiments, deviation may be considered to occur based on the number of sensors that deviate from or comply with the template, the total degree of deviation from or compliance with the template, or other factors, or a combination of such factors. Furthermore, in one embodiment, the device 110 may display a bar graph similar to FIG. 25 (using display 308) for each footstrike, with the template (i.e. "ideal" footstrike) shown with dynamically moving "actual data" bars so that a runner can monitor each footstrike and adjust as desired. In another embodiment, the template 601 may utilize relative footstrike forces measured at each sensor 16 (e.g. relative to the other sensors 16), rather than an absolute force measurement, which may compensate for inaccurate recordation of user weight.

Figure 26:
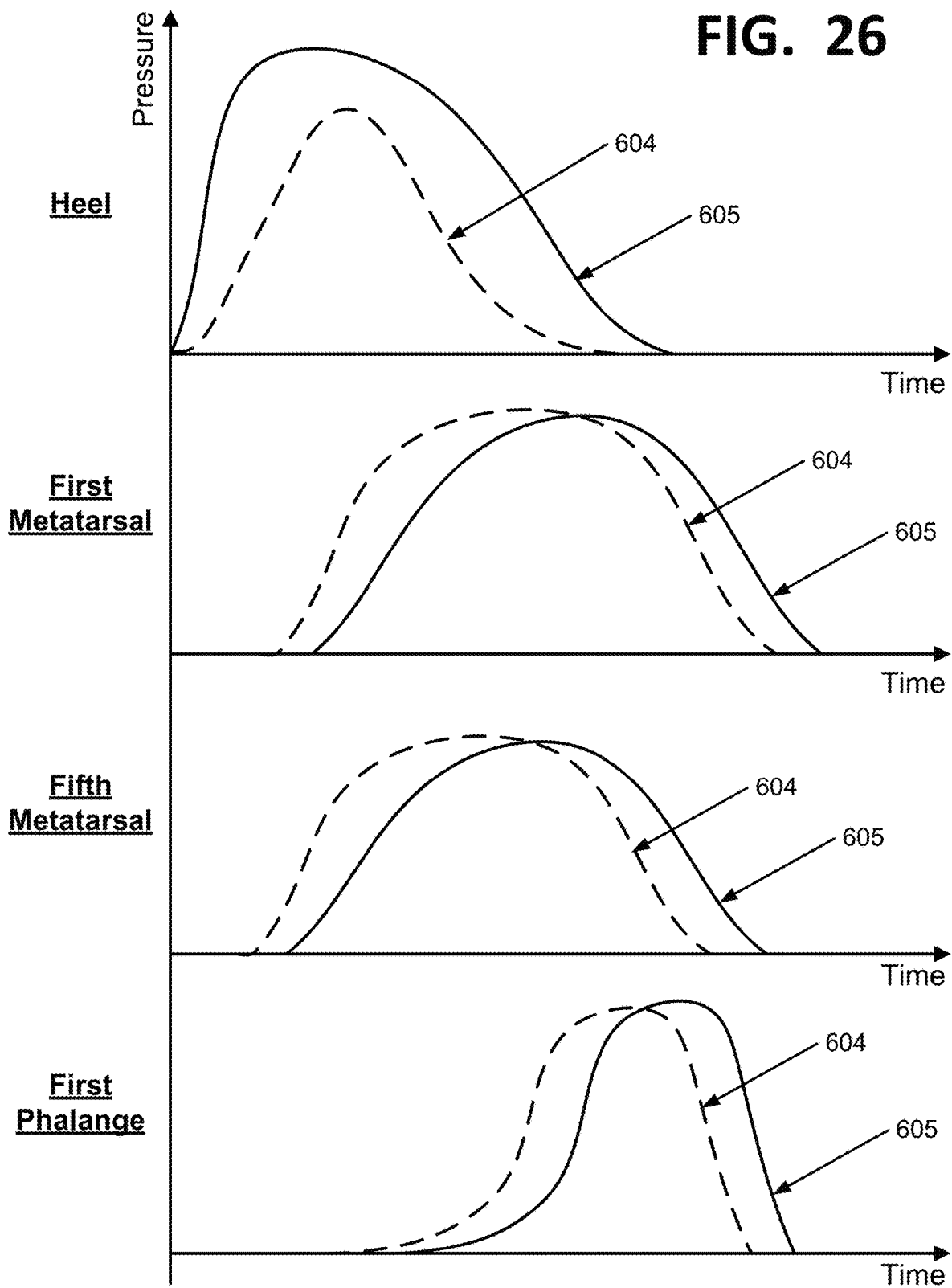
FIG. 26 is a graph showing pressure measured over time for a footstrike using four sensors located in different locations on an article of footwear, with broken lines illustrating another embodiment of a footstrike template.

FIGS. 26-27 illustrate additional examples of footstrike templates 604 (broken lines), based on both measured pressure and timing/sequence of impacts, measured at locations of the sensors 16 in the sensor systems 12 in FIGS. 3-4 and 6-8 and FIGS. 22-23B. Deviation from the template can occur if excessive or insufficient pressure or force is exerted on one or more of the sensors 16 and/or if the sequence of impacts and/or contact time at each of the sensors 16 differs from the desired sequence or timing. Hypothetical data 605 collected from an athletic activity is shown as solid lines in FIGS. 26-27. It is understood that threshold tolerances for pressure and/or timing may be used in these embodiments, but are not illustrated. As seen in FIG. 26, the pressure measured at the heel exceeds the desired value in the template and occurs at approximately the same timing, but with a larger contact interval. In this same example, the pressure measured at the first and fifth metatarsals is slightly smaller than the desired value in the template 604 and has approximately the same contact interval, but occurs at a later timing than the template 604. Further, in this example, the pressure measured at the first phalange is approximately the same as the desired value in the template 604 and has approximately the same contact interval, but occurs at a later timing than the template 604. Depending on the rules governing the definition of deviation, this footstrike may be considered to be too heel-heavy and may constitute a deviation from the template 604. FIG. 27 illustrates the same data 605 and template 604 as FIG. 26, and also illustrates an intermediate template 606 (dot-dash lines) that can be used in gradually coaching a user's performance toward the ultimate goal template 604, as described above.

Figure 28:
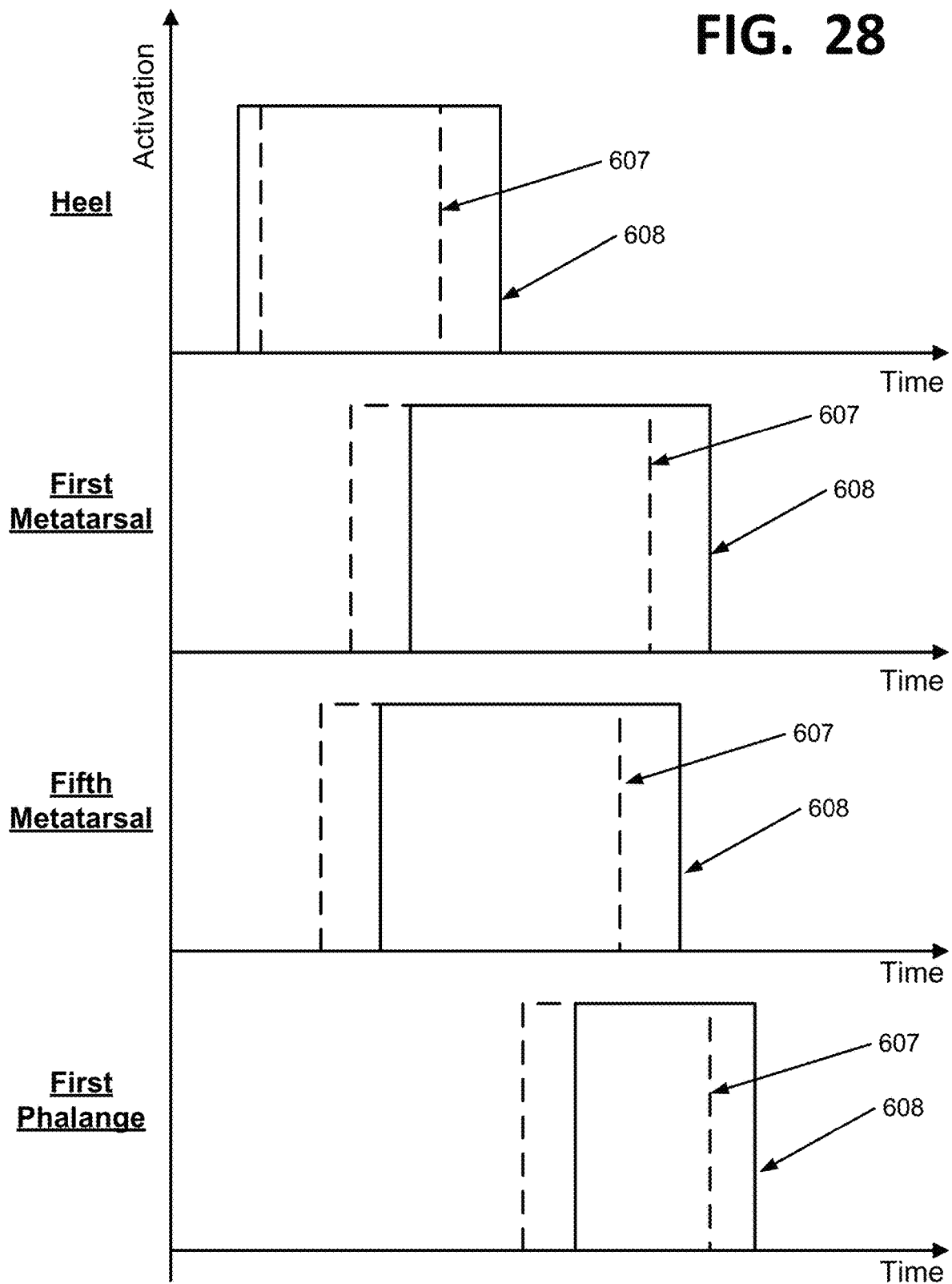
FIG. 28 is a graph showing activation of a binary-type sensor over time for a footstrike using four sensors located in different locations on an article of footwear, with broken lines illustrating another embodiment of a footstrike template.

FIG. 28 illustrates a further example of a footstrike template 607 (broken lines), based on timing/sequence of impacts, measured at locations of the sensors 16 in the sensor systems 12 in FIGS. 3-4 and 6-8 and FIGS. 22-23B. In this embodiment, the data from the sensors 16 is not dynamic in nature, and consists only of binary "active" and "inactive" data. In other words, the sensors 16 in this embodiment only detect force and do not quantitatively measure force, and when a certain threshold pressure has been applied to the sensor 16, the system 12 will read that the sensor is "active." This functioning may be based on the configuration of the module 22 and/or the capabilities of the sensors 16, in various embodiments. Deviation from the template can occur if the sequence of impacts and/or the contact time at each of the sensors 16 differs from the desired sequence or timing. It is understood that threshold tolerances for timing may be used in these embodiments, but are not illustrated. Hypothetical data 608 collected from an athletic activity is shown as solid lines in FIG. 28. As seen in FIG. 28, the contact time measured at the heel is greater than that of the template, and the activation of the other three sensors 16 is later than specified by the template. Depending on the rules governing the definition of deviation, this footstrike may be considered to be too heel-focused and may constitute a deviation from the template 607.

Figure 29:
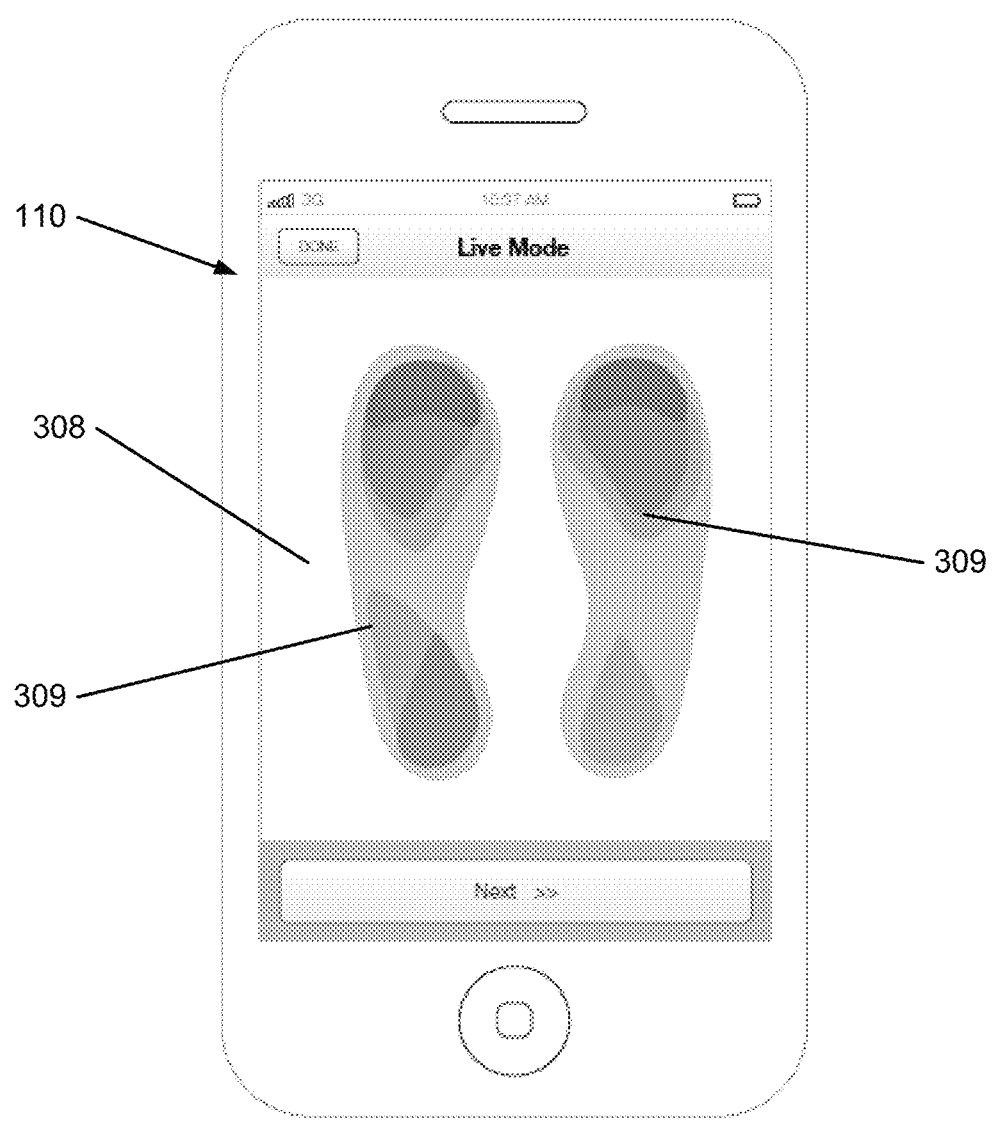
FIG. 29 is a front view of an electronic device with a graphical display showing force or impact of a footstrike.

FIG. 29 illustrates another embodiment of a potential graphical display that may be generated by the device 110 to indicate deviation (or lack thereof) based on real-time analysis of data. In FIG. 29, the device 110 may have a display 308 that depicts one or both of the user's feet using foot graphics 309. In this embodiment, different colors or intensities can be used to depict localized force or impact of each footstrike. Additionally, different colors or intensities can be used to depict whether localized force or impact is higher or lower than dictated by the template. In this way, the foot graphics 309 may provide an indication to the user indicating deviation or compliance with the template. It is understood that the "higher" or "lower" impact values may be absolute values in one embodiment, which may depend on the weight of the user, or may be relative values in another embodiment, e.g. the relative force on the heel vs. the midfoot. Different types of graphical displays may be used for different types of sensor systems, such as graphical displays of actual biometric motions for throwing, running, jumping, etc., vs template movement patterns.

In one embodiment, the module 22 and/or the electronic device 110 may include a GPS module 209 that is configured to detect the position of the user, as described above. Additionally, in one embodiment, the device 110 may include a mapping application or other such software that may work in conjunction with the data from the GPS module 209. Such software may also work in connection with environmental information, terrain information, and other information related to the user's position. "Environmental information," as used herein, includes information about the environment around the user's position, such as architectural or historical landmarks, businesses, parks, monuments, museums, recreational areas and activities, and other points of interest. "Terrain information," as used herein, includes information about the terrain at the user's position, such as elevation, grade, ground conditions (e.g. rocks, dirt, grass, thick or tall weeds, running or standing water, pavement, swampland, wet or snow-covered ground, indoors, etc.), and other information about the terrain. In one embodiment, environmental information and terrain information may be obtained by communication with an external server or other device, and may involve the device 110 transmitting the user's position to an external server and receiving information from the external server based on the position information. In other embodiments, at least some environmental and/or terrain information may additionally or alternately be included within the software or may be obtained from computer-readable storage media connected to the device 110. In a further embodiment, the device 110 may be configured to provide information of upcoming environmental features or terrain changes, based on the user's path.

In one embodiment, the device 110 may include software that generates customized travel routes based on position information received from the GPS module 209, in combination with environmental information and/or terrain information. Information about the user's position can be utilized to provide a running path for the user that passes by or through areas that may be of interest to the user. Input from the user may also be utilized, such as input regarding environmental and/or terrain preferences, as well as a specific distance, pace, run time, or other athletic input. For example, in one embodiment, the device 110 may be used to generate a five kilometer running or biking path that passes by notable architectural landmarks. Such landmarks may be specifically identified by the user and/or may be identified automatically by the device 110. Automatic identification may be performed using an input of the user's general preference for architectural landmarks, or such landmarks may be identified based on other information. Multiple such preferences may be combined into a single run. In another embodiment, the device 110 may be used to generate a five-kilometer path that passes over certain terrain, such as inclines or declines, certain types of ground, etc. Again, multiple such preferences may be combined into a single run. In a further embodiment, the method may be utilized to generate a path that incorporates both desired environmental characteristics and desired terrain characteristics. The device 110 may also be configured to modify existing travel routes based on the same types of information.

In one embodiment, the device 110 may include software that modifies or alters biomechanical movement template usage based on environmental information and/or terrain information. For example, a runner may wish to utilize one footstrike pattern, stride length, lean, etc., for one terrain and a different footstrike pattern, stride length, lean, etc., for another terrain. Such environmental or terrain information may be received from user input in one embodiment, or may be obtained from another source automatically, based on position information received from the GPS module 209, in combination with environmental information and/or terrain information. Other input from the user may also be utilized, such as input regarding template preferences for specific types of terrain, as well as a specific distance, pace, run time, or other athletic input. Pre-existing rules may be set to govern which terrains are associated with which templates, and such rules may be set by the user and/or automatically assigned. In one embodiment, a user may manually indicate terrain information to the device 110 (e.g. by selection from a list), and the device 110 can automatically switch to a different template based on such terrain information, if necessary. In another embodiment, terrain information may be automatically obtained, based on position information, such as by communication with an external device as described above. The device may modify the biomechanical movement template based on the terrain information, as described below, which may include changing the template and/or switching to a different template.

Figure 30:
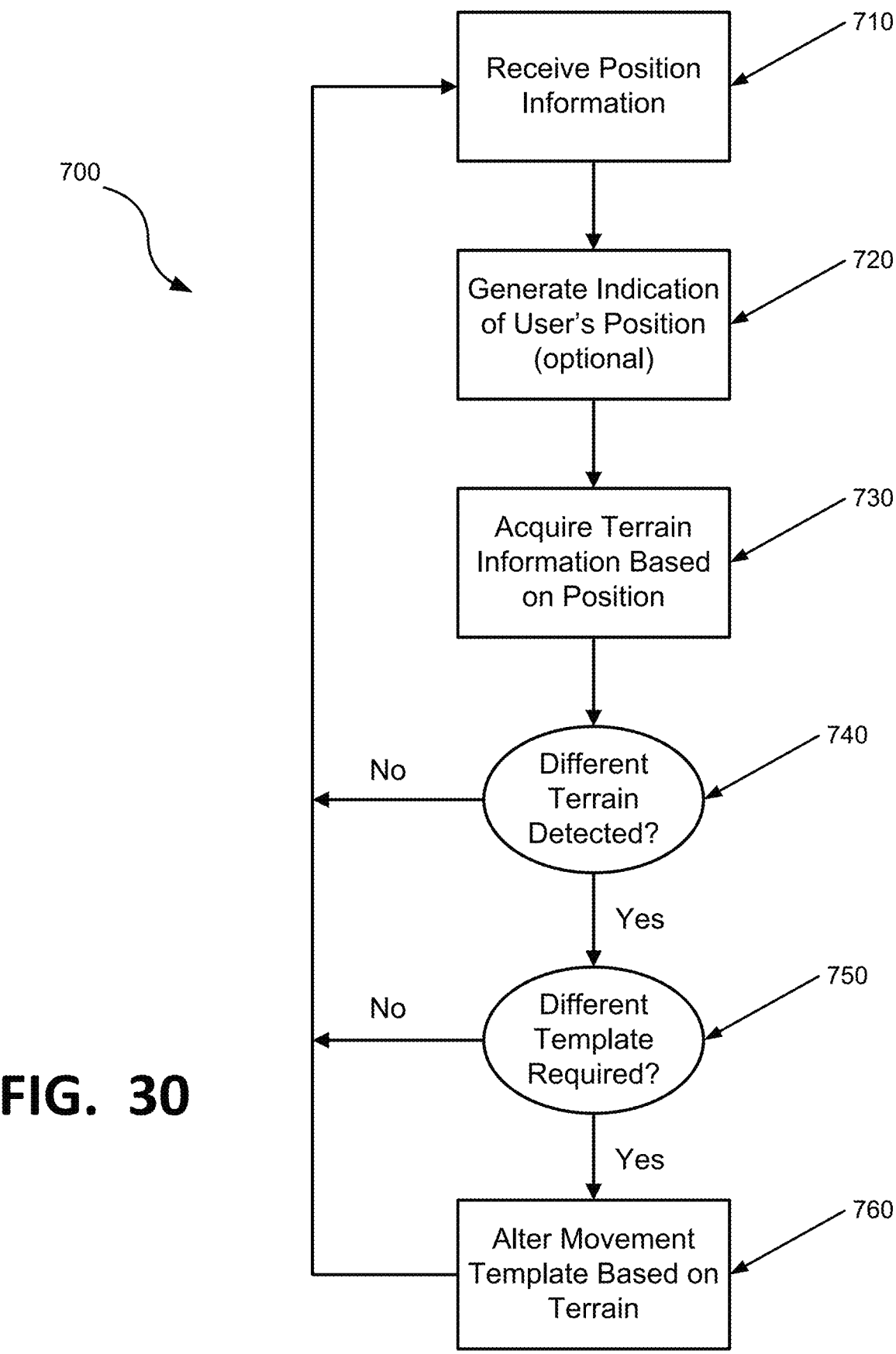
FIG. 30 is a flow diagram illustrating one embodiment of a method for altering a template for biomechanical movement that is usable in connection with analysis of an athletic activity.

FIG. 30 illustrates one embodiment of a method 700 for providing a template for use as described above, which incorporates terrain information acquired based on the user's position detected by the GPS module 209. It is understood that the device 110 and/or certain components within the device 110 (e.g. processor 302 and/or memory 304) may be used in performing this method 700. The device 110 receives position information for the user from the GPS 209, at step 710. The device 110 may then generate an indication of the user's position in one embodiment, such as on a map graphic on the display 308, at step 720. The user's position need not be indicated, and may be optional in another embodiment. The device 110 then acquires terrain information based on the user's position, at step 730. As described above, the terrain information may be acquired from information stored in the memory 304 or other storage media connected to the device 110, from an external server or other device 110, or a combination of such means. The device 110 may continuously update terrain information as the position information changes, and if no change in terrain is detected, at step 740, then the process repeats by receiving more position information (at 710) and proceeding as described above. If a different terrain is detected, at step 740, then the device 110 determines whether a different biomechanical movement template is required, at step 750. If a different template is not required, then the process repeats by receiving more position information (at 710) and proceeding as described above. If a different template is required, then the device 110 alters the template based on the different terrain, at step 760. In one embodiment, the altering is performed automatically by the device 110 based on pre-existing rules. In such a configuration, the fact that the template has been altered may be indicated to the user in one embodiment, and the indication may be done visually, audibly, and/or tactilely. In another embodiment, the device 110 may alter the template by prompting the user to manually select a different template, and may optionally provide a limited list of templates that may be considered suitable based on pre-existing rules. In one embodiment, the device 110 can conduct the method 700 for multiple different movement templates simultaneously, including multiple templates based on input from a single sensor system 12 and/or from multiple sensor systems 12. It is understood that the method 700 may be used in connection with a pre-plotted route. For example, the method 700 may be used for a marathon route, and can assist the user by identifying necessary changes in biomechanical movement based on changing terrain, as well as notifying the user of upcoming terrain changes and associated movement changes. The device 110 may also be configured to dynamically update the route if the data from the GPS module 209 indicates that the user is not following the route.

In one embodiment, the device 110 may include software to coach a user when transitioning to a new footwear type. For example, this system may be used when transitioning from traditional footwear to minimal footwear for the avoidance of injuries. In particular, minimal footwear structures are configured to cooperatively articulate, flex, stretch, or otherwise move to provide an individual with a sensation of natural, barefoot running. The sole structure of minimal footwear is generally thinner throughout its length with less cushioning than traditional footwear and little or no heel-to-toe drop (the change in elevation of footwear from at least a portion of the heel to at least a portion of a non-heel region, e.g., any portion of the foot that is distal to the heel, such as the arch, metatarsus, forefoot, toe region, and combinations thereof). For example, traditional running footwear has a heel-toe ramp resulting from a vertical heel-to-toe drop of 12 mm or more. Minimal footwear, on the other hand, has a substantially zero heel-to-toe drop. Partial minimal footwear, a configuration between a traditional and a minimal structure, has a 4-12 mm heel-to-toe drop. The configuration of most minimal footwear structures results in a different distribution of stress throughout the feet and the body, e.g., when running. For example, experienced minimal footwear runners tend to strike the ground in the midfoot or forefoot regions and have substantially no vertical impact transient on ground impact. Traditional footwear wearers, on the other hand, tend to have a more posterior strike pattern (a heel-first footstrike), a higher vertical impact transient, as well as greater dorsiflexion of the foot and less knee flexion at foot strike.

Wearers transitioning to minimal footwear running shoes often do not sufficiently alter their biomechanics to properly adapt to the minimal footwear conditions and are consequentially more likely to suffer injuries when switching to the minimal footwear type. Thus, a transitional coaching program may be desired to acclimate a wearer to a different footwear type (e.g., minimal, partial minimal) in order to properly transition to the biomechanics associated with the new footwear while minimizing chances of injuries. For example, a program for transitioning a user from traditional footwear to minimal footwear may include coaching towards a plantar-flexed ankle at footstrike, shorter ground contact, reduced knee flexion, and/or reduced heel pressure at footstrike. Accordingly, systems and methods of the present disclosure may be used for a footwear transitional program to transition a user from a first footwear type to a second footwear type (e.g., from traditional footwear to minimal footwear, from partial minimal footwear to minimal footwear, and the like).

In certain embodiments, the plurality of sensors 16 are located in different locations on the article of footwear. A footstrike pattern of a user can be detected based on a sequence of the forces sensed by the sensors and/or a level of the forces sensed by the sensors 16 transmitting force data to an electronic device 110 through sensor leads 18 or through wireless transmission. The electronic device 110 compares the data to a desired footstrike pattern corresponding to the footwear type. The sensors may also be configured to measure a pressure distribution under the wearer's foot so as be able to obtain pressure distribution data and compare such data to a foot pressure template corresponding to the footwear type. Specific areas of the foot, e.g., the midfoot, may receive increased stress during an athletic activity such as running due to a different movement of the foot with minimal footwear. Accordingly, these specific areas can be targeted more closely than others via placement of the sensors. Leg biomechanics also change when transitioning types of footwear. Thus, a leg sensor system, such as legwear 91 of FIGS. 18-19 may also be provided in order to sense force exerted on a leg of a user. The sensed force on the leg can then be compared to a desired biomechanical leg movement pattern to determine whether a deviation from the biomechanical movement template exists.

In one embodiment, the footwear transitional program includes one or more desired footstrike templates which correspond to the footwear type to which the user is transitioning. In use, the electronic device compares data received from the sensor system to a footstrike template corresponding to a desired footstrike pattern. The electronic device determines whether a deviation from the desired footstrike template exists in order to train a wearer towards a preferred footstrike corresponding to the particular footwear type. For example, a deviation may be determined to exist if the degree of deviation exceeds a predetermined threshold.

During a particular activity, a user may periodically receive indications and/or alerts, e.g., by the electronic device transmitting a signal to a second electronic device, such as an external device held by the user during the activity. The indications notify a user when deviations are determined and the alerts notify a user if a number of deviations exceeds a predetermined deviation threshold. The indications and alerts may be visual, audible, and/or tactile depending on the electronic device capabilities and/or a user selection. For example, in some embodiments, the indications and alerts may provide specific coaching guidelines to a user during an athletic activity, such as "Strike the ground closer to the forefoot" or "Maintain shorter ground contact." In some other embodiments, the indications and alerts may be less specific, and may include, for example, a number of beeps and/or visual flashes or differing intensity or repetition depending on the type or severity of the indication/alert. Alternatively, or in addition to receiving indications throughout an activity, the total count of deviations may be provided at the end of the activity. A user may also opt to have the system record data throughout the course of a particular athletic activity, e.g., during a run.

In addition to analyzing and comparing footstrike data to desired patterns, the system can recommend a relative usage amount for a subsequent footwear wearing period. Upon completion of the athletic activity session, the system may provide feedback to the user based on data recorded during the activity and a desired footstrike pattern of the footwear. For example, the feedback may include an activity report for a subsequent athletic activity session, e.g., a suggested distance and speed for a next run. For instance, if a high amount or number of deviations were recorded during the athletic activity session, the subsequent activity report may recommend an activity of lesser distance and/or lower speed than the prior activity. Conversely, if few or no deviations were recorded during an athletic activity session, the subsequent activity report may be of greater distance and/or higher speed than the prior activity. The feedback may also include a stretching activity following the athletic activity session based on sensed deviations from the desired footstrike pattern of the footwear. The suggested stretching exercises may include calf stretching and strengthening in addition to stretching and strengthening the foot. The system may also prompt a user for input relating to a perceived discomfort during an athletic activity which may include a level of discomfort and/or specifying a general area of discomfort (the arch, the heel, the calf, and the like). Accordingly, the perceived discomfort input may affect the feedback reported to the user. Over the duration of the footwear transitional program, the device is configured to record a plurality of athletic activities for a particular user. The transitional program may be a preset duration, e.g., a number of athletic activities, or a total time and/or distance of recorded data as provided by positional data from the GPS module. In some embodiments, the duration of the transitional footwear program may change throughout the program, e.g., based on a number or frequency of recorded deviations until, for instance, a deviation count threshold is reached.

The footwear transitional program may include a single desired footstrike pattern or a plurality of footstrike patterns which change throughout the footwear transitional program. For example, for a minimal footwear transition program, an initial desired footstrike pattern may allow for some amount of a heel-first footstrike without determining a deviation, at a beginning of the program. Similarly, a final desired footstrike pattern may be a midfoot or forefoot footstrike and the device will determine a deviation to exist if any portion of the heel is sensed to strike the ground during initial impact of the foot. Generally, the final desired footstrike pattern will substantially correspond to a most preferred footstrike pattern for the footwear type. The footstrike patterns may vary during the footwear transitional program based on a designated amount of usage, e.g., a total record time and/or distance or a number of athletic activities. This iterative arrangement may aid in slowly transitioning the user from the first footwear type to the second footwear type while minimizing injuries due to the transition.

The footwear transitional program may also be customizable by a user type. For example, a user may select a customizable footwear transition program based on at least one of age, weight, gender, excursion distance, and speed. Accordingly, various aspects of the transitional footwear program may change based on customization. Depending on the various customization factors, the transitional program may have a duration of a few weeks to several months to adjust and coach a user to a new footwear type in order to prevent or minimize any such transition-related injuries. In another example, the number of iterations of footstrike patterns in the footwear transitional program may be also vary based on the particular user. In some embodiments, a user may select a footwear transition program from a plurality of footwear transition program templates, e.g., corresponding to a particular footwear type and/or a type of user. Accordingly, each footwear transitional program may have a plurality of footstrike templates, potentially of a differing total number of templates and/or differing in the desired footstrike patterns included in each program. Additionally or alternatively, the footwear transition program may be automatically selected by the system based on data collected from previous athletic activity sessions (e.g., historical running data, walking data, and the like). Accordingly, the system may use historical data stored for the user, in conjunction with an identified new type of footwear, to determine a footwear transition program for the user.

In some embodiments, the system may establish an end to the transition program once foot strike patterns exhibit a proper transition to the footwear type. For example, as a user acclimates to a minimal footwear, the user should eventually develop a footstrike pattern wherein the mid-foot region strikes first rather than the heel. Once this footstrike pattern is detected (e.g., via sensor data, number of deviations, etc.) the system may determine that the user has successfully transitioned to the new footwear type and the program may end. In some examples, the end of the transition program may be transmitted to the user (e.g., via an audio or visual congratulatory message, or the like).

The transitional footwear program need not be limited to running. For example, minimal shoes have been found to be beneficial to elderly persons, and therefore the above transition program can be incorporated effectively at a slower pace than running.

As described above, in one embodiment, one or more templates may be created by the user by recording an actual movement pattern of the user. In one embodiment, a user may identify an "ideal" movement pattern or series of movement patterns and create one or more templates for future activity, as well as incorporating other information from the recorded movement pattern for such future activity. For example, a user may perform what is considered to be an "ideal" run, including at least one ideal biometric movement pattern, such as an ideal footstrike pattern, stride length, footstrike force, etc., and may set such ideal biometric movement pattern(s) as one or more templates (e.g. by using the device 110). Other information about the ideal run may be recorded as well, such as the distance, speed, route, estimated calories burned, etc., and this information may be used to create an "ideal run" template for the user to follow to re-create the run. Similar techniques may be used for other activities.

In another embodiment, the device 110 and associate software may provide the ability for a user to review performance metrics from a previous activity and identify areas of success and/or areas that need improvement. This feature may be incorporated into the creation of the "ideal" activity described above, and may provide the ability for the user to modify certain aspects of the template(s) for the "ideal" activity. Additionally, the recordation of past performance metrics can enable the user to track performance, improvement, trends, progress, etc., over time, and the device 110 may provide such past data for access and review. Types of information tracked by the device 110 may include degree of success with compliance to various templates as well as additional information including, without limitation, speed, distance, steps or repetitions, energy used, jump height/distance, stride length, and any other information mentioned elsewhere herein. Recorded data from an activity may be uploaded from the recording device 110 to another device 110, such as through "sync" procedures used in the art. One or more devices 110 can thereby record accumulated performance metric data for a number of different activities over time, and further processing and refining can be performed to present such data in a form that is easy for the user to review. In one embodiment, recorded data and/or analyzed data may be uploaded to a remote server/website for access through a webpage, and may additionally be shared with an online "community," where users can compare progress and activity with other users. The online community may have filtering capabilities as well, for example, to permit the user to compare information with others having similar physical build, activity level, age, etc. The online community may also have "challenge" capabilities to allow one user to challenge another user in achieving an accomplishment, such as more consistently conforming to a biomechanical movement template. Data and other information obtained from the user may also be used in a social networking context as described below, and it is understood that the social networking may be integrated with or otherwise associated with the online community. Further, devices 110 used in connection with such performance metrics can form a detailed user profile that includes performance data, as well as relevant personal and other information, in one embodiment. Such a user profile may also be used for an online community as described above and/or for social networking, as described below. As more data is collected, the device(s) 110 can offer more closely customized data presentations, analysis, and suggestions or indications for improvement.

In one embodiment, the device 110 and associated software may provide one or more data entry screens for the user to enter personal data that can be used to build the user profile. For example, the user may be prompted to enter physical data that may influence system performance and template selection, such as age, gender, height, weight, etc. As another example, the user may be prompted to enter identifying information, such as name, birthdate, login information (e.g. username and password), etc. As a further example, the user may be prompted to enter preference information, such as interests, terrain and/or environmental preferences as described above, color and layout preferences, and general software functionality preferences, including feedback preferences such as the form(s) of the indications of success/failure, what data is collected, analyzed, and/or displayed, and other functionality preferences. As yet another example, the user may be prompted to enter data regarding a planned future activity that will utilize the device 110 and system 400, such as the length and intensity of the activity, specific goals of the activity, desired functionality of the device 110 for the activity, and other such information.

The device 110 and associated software may also be configured to accept incorporation of new hardware and peripherals (e.g. new sensor systems 12, augmented reality devices, etc.), and the device 110 may be configured to accept data input from, and communicate with, various different types of hardware. As new hardware is added (e.g. new sensor systems 12), the user profile may be updated accordingly.

In another embodiment, the device 110 and associated software may provide guidance to the user to assist in compliance to a biomechanical movement template. For example, for a template for running cadence or pace, the device 110 may provide a song or beat with a rhythm or tempo that corresponds to the desired cadence or pace. Other examples are recognizable to those skilled in the art.

In another embodiment, the device 110 and associated software may provide safety features that are activated when the device 110 senses an accident (e.g. a fall) based on data received from the sensor system 12. For example, the device 110 may detect a fall or other major discontinuity in data, and may prompt the user to confirm whether a safety or health issue exists. If the user indicates that an issue exists, or if no response is received in a set time period, the device 110 may contact emergency responders, such as by phone call, SMS, email, or other means. Depending on the capability of various sensors, the device 110 may also be able to relay information such as respiration, heart rate, temperature, etc.

In another embodiment, the device 110 and associated software may be used in connection with social networking applications. For example, performance metric data may be compared with data from other social networking contacts. As another example, collected performance metric data may be translated into "points" or "credits" for social networking games, where the user is able to modify or further play such games using such points or credits. This can provide an additional source of encouragement to the user for reaching performance and exercise goals.

As will be appreciated by one of skill in the art upon reading the present disclosure, various aspects described herein may be embodied as a method, a data processing system, or a computer program product. Accordingly, those aspects may take the form of an entirely hardware embodiment, an entirely software embodiment or an embodiment combining software and hardware aspects. Furthermore, such aspects may take the form of a computer program product stored by one or more tangible computer-readable storage media or storage devices having computer-readable program code, or instructions, embodied in or on the storage media. Any suitable tangible computer readable storage media may be utilized, including hard disks, CD-ROMs, optical storage devices, magnetic storage devices, and/or any combination thereof. In addition, various intangible signals representing data or events as described herein may be transferred between a source and a destination in the form of electromagnetic waves traveling through signal-conducting media such as metal wires, optical fibers, and/or wireless transmission media (e.g., air and/or space).

As described above, aspects of the present invention may be described in the general context of computer-executable instructions, such as program modules, being executed by a computer and/or a processor thereof. Generally, program modules include routines, programs, objects, components, data structures, etc. that perform particular tasks or implement particular abstract data types. Such a program module may be contained in a tangible, non-transitory computer-readable medium, as described above. Aspects of the present invention may also be practiced in distributed computing environments where tasks are performed by remote processing devices that are linked through a communications network. Program modules may be located in a memory, such as the memory 204 of the module 22 or memory 304 of the external device 110, or an external medium, such as game media 307, which may include both local and remote computer storage media including memory storage devices. It is understood that the module 22, the external device 110, and/or external media may include complementary program modules for use together, such as in a particular application. It is also understood that a single processor 202, 302 and single memory 204, 304 are shown and described in the module 22 and the external device 110 for sake of simplicity, and that the processor 202, 302 and memory 204, 304 may include a plurality of processors and/or memories respectively, and may comprise a system of processors and/or memories.

The various embodiments of the athletic activity analysis system described herein provide benefits and advantages over existing technology. For example, sensor systems, devices, and methods as described herein can provide detailed automated coaching to guide a user toward changing biometric movement patterns in a safe, healthy, and efficient manner. Embodiments described herein can also provide enhanced ability for the user to monitor his/her performance, both dynamically in real-time, as well as retrospectively. Embodiments described herein can also provide guidance and assistance for a user to improve performance during an activity. Embodiments described herein can further provide assistance to runners, bikers, triathletes, etc., in designing travel routes for workouts, as well as negotiating unfamiliar travel routes. Other advantages are recognizable to those skilled in the art.

Several alternative embodiments and examples have been described and illustrated herein. A person of ordinary skill in the art would appreciate the features of the individual embodiments, and the possible combinations and variations of the components. A person of ordinary skill in the art would further appreciate that any of the embodiments could be provided in any combination with the other embodiments disclosed herein. It is understood that the invention may be embodied in other specific forms without departing from the spirit or central characteristics thereof. The present examples and embodiments, therefore, are to be considered in all respects as illustrative and not restrictive, and the invention is not to be limited to the details given herein. The terms "first," "second," "top," "bottom," etc., as used herein, are intended for illustrative purposes only and do not limit the embodiments in any way. Additionally, the term "plurality," as used herein, indicates any number greater than one, either disjunctively or conjunctively, as necessary, up to an infinite number. Further, "Providing" an article or apparatus, as used herein, refers broadly to making the article available or accessible for future actions to be performed on the article, and does not connote that the party providing the article has manufactured, produced, or supplied the article or that the party providing the article has ownership or control of the article. Accordingly, while specific embodiments have been illustrated and described, numerous modifications come to mind without significantly departing from the spirit of the invention and the scope of protection is only limited by the scope of the accompanying Claims.

What is claimed is:

1. A system for transitioning from a first footwear type to a second footwear type different from the first footwear type, comprising:
   a sensor system configured to sense biomechanical movement of a foot of a user, the sensor system comprising:
      a plurality of sensors engaged with an article of footwear of the second footwear type and configured to sense biomechanical movement of a foot of the user; and
      an electronic module configured to collect data based on input from the plurality of sensors; and
   an electronic device in communication with the electronic module, wherein the electronic device includes a processor and a non-transitory computer-readable storage medium storing computer-executable instructions that, when executed, cause a processor to perform a method comprising:
      recording a plurality of athletic activities performed by the user as part of a footwear transitional program, wherein each of the plurality of athletic activities includes data from the electronic module;
      comparing data from each of the plurality of athletic activities to a corresponding footstrike template of a footwear transitional program for transitioning from the first footwear type to the second footwear type, wherein the footwear transitional program includes a plurality of footstrike templates having incremental changes between consecutive footstrike templates and associated with transitioning to a preferred footstrike of the second footwear type, wherein the preferred footstrike of the second footwear type differs from a preferred footstrike of the first footwear type, and wherein the plurality of footstrike templates includes a final footstrike template corresponding to a most preferred footstrike pattern of the second footwear type, and at least one intermediate footstrike template corresponding to a footstrike pattern between the preferred footstrike of the first footwear type and the preferred footstrike of the second footwear; and
      generating a footstrike analysis report on a display of the electronic device, wherein the footstrike analysis report includes footstrike analysis of the user based on comparing data from each of the plurality of athletic activities to a footstrike template at a corresponding point in the footwear transitional program.

2. The system of claim 1, wherein the footstrike analysis report includes a coaching feedback to the user based on the plurality of athletic activities performed by the user as part of a footwear transitional program.

3. The system of claim 2, wherein the coaching feedback includes a suggested activity report for a subsequent athletic activity.

4. The system of claim 2, wherein the electronic device is further configured to:
   modify a duration of the footwear transitional program based on comparing data from each of the plurality of athletic activities to a corresponding footstrike template.

5. The system of claim 1, wherein the footwear transitional program is customizable by a user type.

6. The system of claim 5, wherein a user selects a customizable footwear transition program based on at least one of age, weight, gender, excursion distance, and speed.

7. The system of claim 1, wherein the footwear transitional program includes a plurality of desired footstrike patterns varying throughout the footwear transitional program, and a plurality of coaching recommendations associated with coaching instructions for the user to transition to each of the desired footstrike patterns.

8. The system of claim 1, wherein the electronic device is further configured to determine whether a deviation from the corresponding footstrike template, and generate an indication to the user when a deviation from the corresponding footstrike template is determined to exist.

9. The system of claim 8, wherein the electronic device is further configured to generate an alert to the user when a number of deviations exceeds a predetermined deviation count threshold.

10. The system of claim 1, wherein the second footwear type is a minimal footwear and the preferred footstrike is a midfoot or forefoot strike pattern.

11. The system of claim 1, wherein comparing data from each of the plurality of athletic activities to a corresponding footstrike template comprises:
   detecting a footstrike pattern based on analysis of data from the electronic module; and
   comparing the footstrike pattern to the corresponding footstrike template.

12. The system of claim 11, wherein the plurality of sensors are located in different locations on the article of footwear, and wherein the footstrike pattern is detected based on at least one of a sequence of forces sensed by the sensors and a level of forces sensed by the sensors.

13. The system of claim 12, wherein the plurality of sensors are configured to measure a pressure distribution under the foot and the electronic device is further configured to compare pressure distribution data to a foot pressure template.

14. A system for transitioning from a first footwear type to a second footwear type, comprising:
   a sensor system configured to sense biomechanical movement of a foot of a user, the sensor system comprising an electronic module configured to wirelessly transmit data generated by the sensor system; and
   an electronic device in communication with the electronic module, wherein the electronic device includes a processor and a non-transitory computer-readable storage medium storing computer-executable instructions that, when executed, cause a processor to perform a method comprising:

selecting a footwear transition program, each footwear transition program comprising a plurality of desired footstrike patterns corresponding to a preferred footstrike of the second footwear type;

recording a plurality of athletic activities performed by the user as part of a footwear transitional program, wherein each of the plurality of athletic activities includes data from the electronic module; receiving the data from the electronic module;

comparing data from each of the plurality of athletic activities to a corresponding footstrike template of a footwear transitional program for transitioning from the first footwear type to the second footwear type, wherein the footwear transitional program includes a plurality of footstrike templates having incremental changes between consecutive footstrike templates and associated with transitioning to a preferred footstrike of the second footwear type, wherein the preferred footstrike of the second footwear type differs from a preferred footstrike of the first footwear type, and wherein the plurality of footstrike templates includes a final footstrike template corresponding to a most preferred footstrike pattern of the second footwear type, and at least one intermediate footstrike template corresponding to a footstrike pattern between the preferred footstrike of the first footwear type and the preferred footstrike of the second footwear; and generating a footstrike analysis report on a display of the electronic device, wherein the footstrike analysis report includes footstrike analysis of the user based on comparing data from each of the plurality of athletic activities to a footstrike template at a corresponding point in the footwear transitional program.

15. The system of claim 14, wherein the preferred footstrike of the second footwear type includes a midfoot-strike template or a forefoot-strike template, and the plurality of footstrike templates includes patterns that transition from a heel-strike pattern to a midfoot-strike pattern or a forefoot-strike pattern.

16. The system of claim 14, wherein the electronic device is further configured to determine whether a deviation from the corresponding footstrike template, and generate an indication to the user when a deviation from the corresponding footstrike template is determined to exist.

17. The system of claim 14, wherein the plurality of footstrike templates vary based on collected user information.

18. The system of claim 14, wherein the corresponding footstrike template of the footwear transitional program varies after a predetermined amount of usage.

19. The system of claim 14, wherein the footstrike analysis report includes coaching feedback to the user based on the plurality of athletic activities performed by the user as part of a footwear transitional program.

20. The system of claim 14, further comprising computer readable instructions that, when executed, cause the processor to modify a duration of the footwear transitional program based on comparing data from each of the plurality of athletic activities to a corresponding footstrike template.

* * * * *

UNITED STATES PATENT AND TRADEMARK OFFICE
CERTIFICATE OF CORRECTION

| | |
|---|---|
| PATENT NO. | : 11,918,854 B2 |
| APPLICATION NO. | : 17/142784 |
| DATED | : March 5, 2024 |
| INVENTOR(S) | : Giedwoyn et al. |

It is certified that error appears in the above-identified patent and that said Letters Patent is hereby corrected as shown below:

On the Title Page

Column 2, item (56) Other Publications, Line 2:
Delete "runnmg" and insert --running-- therefor In the Claims Column 51, Claim 14, Line 8:
After "module;", insert --¶--

Signed and Sealed this
Twenty-fifth Day of June, 2024

Katherine Kelly Vidal
*Director of the United States Patent and Trademark Office*